United States Patent
Han et al.

(10) Patent No.: US 9,926,299 B2
(45) Date of Patent: Mar. 27, 2018

(54) INHIBITORS OF BRUTON'S TYROSINE KINASE

(71) Applicant: Centaurus BioPharma Co., Ltd., Beijing (CN)

(72) Inventors: Yongxin Han, Beijing (CN); Rong Yu, Beijing (CN); Zanping Wang, Beijing (CN); Zhi Liang, Beijing (CN); Quan Hu, Beijing (CN); Li Zhu, Beijing (CN); Yuandong Hu, Beijing (CN); Yinghui Sun, Beijing (CN); Na Zhao, Beijing (CN); Yong Peng, Beijing (CN); Xiaofeng Zhai, Beijing (CN); Hong Luo, Beijing (CN); Dengming Xiao, Beijing (CN)

(73) Assignee: Centaurus BioPharma Co., Ltd., Beijing (CN)

(*) Notice: Subject to any disclaimer, the term of this patent is extended or adjusted under 35 U.S.C. 154(b) by 53 days.

(21) Appl. No.: 14/648,265

(22) PCT Filed: Nov. 29, 2013

(86) PCT No.: PCT/CN2013/088177
§ 371 (c)(1),
(2) Date: May 29, 2015

(87) PCT Pub. No.: WO2014/082598
PCT Pub. Date: Jun. 5, 2014

(65) Prior Publication Data
US 2015/0299171 A1  Oct. 22, 2015

Related U.S. Application Data

(60) Provisional application No. 61/771,518, filed on Mar. 1, 2013.

(30) Foreign Application Priority Data

Nov. 30, 2012  (CN) .......................... 2012 1 0505930

(51) Int. Cl.
| | | |
|---|---|---|
| *C07D 403/04* | (2006.01) | |
| *C07D 401/04* | (2006.01) | |
| *C07D 231/38* | (2006.01) | |
| *A61K 31/415* | (2006.01) | |
| *A61K 31/454* | (2006.01) | |
| *A61K 31/496* | (2006.01) | |

(Continued)

(52) U.S. Cl.
CPC ......... *C07D 403/04* (2013.01); *C07D 231/38* (2013.01); *C07D 401/04* (2013.01)

(58) Field of Classification Search
CPC combination set(s) only.
See application file for complete search history.

(56) References Cited

U.S. PATENT DOCUMENTS

| | | |
|---|---|---|
| 7,514,444 B2 | 4/2009 | Honigberg et al. |
| 2010/0035841 A1 | 2/2010 | Jankowski et al. |
| 2012/0157443 A1 | 6/2012 | Bui et al. |

(Continued)

FOREIGN PATENT DOCUMENTS

| | | |
|---|---|---|
| CN | 101421269 A | 4/2009 |
| CN | 101460466 A | 6/2009 |

(Continued)

OTHER PUBLICATIONS

Extended European Search Report for corresponding European Application No. 13858966.8 dated May 10, 2016.

(Continued)

*Primary Examiner* — Amanda L Aguirre
(74) *Attorney, Agent, or Firm* — Renner, Otto, Boisselle & Sklar, LLP

(57) ABSTRACT

The invention provides novel poly-substituted 5-membered heterocyclic compounds represented by Formula (IV), or a pharmaceutically acceptable salt, solvate, metabolite, polymorph, ester, tautomer or prodrug thereof, and a composition comprising these compounds. The compounds provided can be used as selective irreversible bruton's tyrosine kinase (Btk) inhibitors and are further useful to treat inflammatory, auto immune diseases associated with aberrant B-cell proliferation such as RA (rheumatoid arthritis) and cancers. This invention also provides the preparation of a medicament using of Formula (IV), and methods of preventing or treating diseases associated with excessive Btk activity in mammals, especially humans.

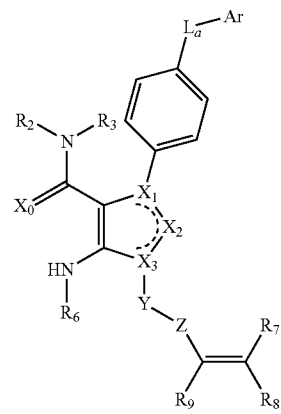

Formula (IV)

9 Claims, No Drawings

(51) Int. Cl.
*A61K 31/4155* (2006.01)
*A61K 31/5377* (2006.01)

(56) References Cited

U.S. PATENT DOCUMENTS

| | | | |
|---|---|---|---|
| 2012/0178753 | A1 | 7/2012 | Honigberg et al. |
| 2013/0090479 | A1 | 4/2013 | Jimenez et al. |
| 2014/0045813 | A1* | 2/2014 | Bentzien ............ C07D 231/14 514/210.18 |
| 2014/0079690 | A1 | 3/2014 | Buggy et al. |
| 2014/0336206 | A1 | 11/2014 | Honigberg et al. |
| 2015/0291554 | A1* | 10/2015 | Springer ............ C07D 401/04 514/326 |

FOREIGN PATENT DOCUMENTS

| | | |
|---|---|---|
| CN | 101610676 A | 12/2009 |
| CN | 101674834 A | 3/2010 |
| CN | 101805341 A | 8/2010 |
| CN | 102159214 A | 8/2011 |
| JP | 2015-524480 A | 8/2015 |
| WO | 2008/039218 A2 | 4/2008 |
| WO | 2009/011880 A2 | 1/2009 |
| WO | 2010-009342 A2 | 1/2010 |
| WO | 2010/055304 A2 | 5/2010 |
| WO | 2011/046964 A2 | 4/2011 |
| WO | 2011/153514 A2 | 12/2011 |
| WO | 2014/025976 A1 | 2/2014 |
| WO | 2014/068527 A1 | 5/2014 |

OTHER PUBLICATIONS

International Search Report for corresponding International Application No. PCT/CN2013/088177 dated Mar. 6, 2014.
Office Action for corresponding Chinese Application No. 201210505930.3 dated Apr. 13, 2015.
Office Action received in corresponding Japanese Application No. 2015-544342 dated Sep. 25, 2017.

* cited by examiner

INHIBITORS OF BRUTON'S TYROSINE KINASE

This application is a national phase of International Application No. PCT/CN2013/088177 filed Nov. 29, 2013 and published in the English language, which claims priority to Application No. CN 201210505930.3 filed Nov. 30, 2012 and to Application No. U.S. 61/771,518 filed Mar. 1, 2013.

FIELD OF THE INVENTION

This invention pertains to compounds that inhibit irreversible bruton's tyrosine kinases, compositions containing the compounds and methods of treating diseases using the compounds.

BACKGROUND OF THE INVENTION

Protein kinases, the largest family of human enzymes, encompass well over 500 proteins. Specifically, tyrosine kinases phosphorylate proteins on the phenolic moiety of tyrosine residues. The tyrosine kinase family includes members that control cell growth, migration, and differentiation. Abnormal kinase activity has been implicated in a variety of human diseases including cancers, autoimmune and inflammatory diseases.

Btk is a member of the Tec family of tyrosine kinases, and has been shown to be a critical regulator of early B-cell development and mature B-cell activation and survival (Khan et al. *Immunity* 1995 3:283; Ellmeier et al. *J. Exp. Med.* 2000 192:1611). B-cell signaling through the B-cell receptor (BCR) leads to a wide range of biological outputs, which in turn depend on the developmental stage of the B-cell. The magnitude and duration of BCR signals must be precisely regulated. Aberrant BCR-mediated signaling can cause deregulated B-cell activation and/or the formation of pathogenic auto-antibodies leading to multiple autoimmune and/or inflammatory diseases.

Evidence for a role for Btk in autoimmune and inflammatory diseases has also been provided by Btk-deficient mouse models. In preclinical murine models of systemic lupus erythematosus (SLE), Btk-deficient mice show marked amelioration of disease progression. In addition, Btk-deficient mice are resistant to collagen-induced arthritis (Jansson and Holmdahl *Clin. Exp. Immunol.* 1993 94:459). A selective Btk inhibitor has been demonstrated dose-dependent efficacy in a mouse arthritis model (Pan et al., *Chem. Med Chem.* 2007 2:58-61).

Btk is also expressed by cells other than B-cells that may be involved in disease processes. For example, Btk is expressed by mast cells and Btk-deficient bone marrow derived mast cells demonstrate impaired antigen induced degranulation (Iwaki et al. *J. Biol. Chem.* 2005 280:40261). This shows Btk could be useful to treat pathological mast cell responses such as allergy and asthma. Also monocytes from XLA patients, in which Btk activity is absent, show decreased TNFα production following stimulation (Horwood et al. *J Exp Med* 197:1603, 2003). Therefore, TNFα mediated inflammation could be inhibited by small molecule inhibitors of Btk. Also, Btk has been reported to play a role in apoptosis (Islam and Smith *Immunol Rev* 178:49, 2000) and thus Btk inhibitors would be useful for the treatment of certain B-cell lymphomas and leukemias (Feldhahn et al. *J Exp Med* 201:1837, 2005).

On Jun. 16, 2012, Biopharmaceutical Company Pharmacyclics announced 2 new phase Ib/II clinical experimental results (PCYC-1102 and PCYC-1108) by using Btk inhibitor Ibrutinib (PCI-32765) for the treatment of chronic lymphocytic leukemia/small lymphocytic lymphoma (CLL/SLL). The experimental results indicated that 61 patients with relapsed/refractory and 31 untreated patients with CLL are highly active and well tolerated, in addition, during the test, none of the patients was discontinuous because of adverse events.

Obviously, the excellent clinical results of Ibrutinib show that highly selective small molecule Btk inhibitors will be the hot star in the field of global drug development.

SUMMARY OF THE INVENTION

This invention provides compounds of Formula (I), Formula (II), Formula (III) or Formula (IV), pharmaceutically acceptable salts, solvates, esters, acids or prodrugs thereof, compositions containing the compounds, and methods of treating diseases related to BTK using the compounds. In certain embodiments, isomers and chemically protected forms of compounds having a structure represented by any of Formula (I), Formula (II), Formula (III) or Formula (IV), are also provided.

In one aspect, the invention provides a compound of Formula (I),

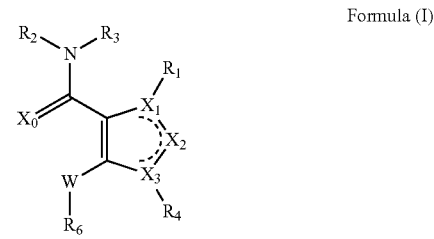

Formula (I)

or a therapeutically acceptable salt, solvate, metabolite, polymorph, ester, tautomer, or prodrug thereof, wherein:

$X_0$ is selected from the group consisting of O, $CH_2$, NH and S;

$X_1$ and $X_3$ are independently selected from the group consisting of C and N;

$X_2$ is selected from the group consisting of $CR_5$, N, and $NR_5$;

$R_1$ is selected from the group consisting of H, $L_2$-(optionally substituted alkyl), $L_2$-(optionally substituted cycloalkyl), $L_2$-(optionally substituted alkenyl), $L_2$-(optionally substituted cycloalkenyl), $L_2$-(optionally substituted heterocycle), $L_2$-(optionally substituted aryl), and $L_2$-(optionally substituted heteroaryl), wherein $L_2$ is selected from the group consisting of a bond, O, S, —S(=O)—, —S(=O)$_2$—, —C(=O)—, -(optionally substituted $C_{1-6}$alkyl)-, and -(optionally substituted $C_{2-6}$alkenyl)-;

$R_2$ and $R_3$ are independently selected from the group consisting of H and optionally substituted lower alkyl; or $R_2$ and $R_3$, together with the nitrogen atom to which they are attached, form a 3-, 4-, 5-, 6-, 7-, or 8-membered heterocyclic ring;

$R_4$ is $L_3$-X-$L_4$-G, wherein, $L_3$ is selected from the group consisting of a bond, optionally substituted alkylene, optionally substituted cycloalkylene, optionally substituted alkenylene, and optionally substituted alkynylene;

X is selected from the group consisting of a bond, O, —C(=O)—, S, —S(=O)—, —S(=O)$_2$—, —$NR_{10}$—, —NHC(O)—, —$NR_{10}$C(O)—, —C(O)$NR_{10}$—, —NHS $-(=O)_2-$, $-S(=O)_2NR_{10}-$, $-NR_{10}S(=O)_2-$, $-NHC(O)O-$, $-OC(O)NR_{10}-$, $-NR_{10}C(O)O-$, $-CH=NO-$, $-ON=CH-$, $-NR_{11}C(O)NR_{11}-$, heteroarylene, arylene, $-NR_{11}C(=NR_{12})NR_{11}-$, $-NR_{11}C(=NR_{12})-$, $-C(=NR_{12})NR_{11}-$, $-OC(=NR_{12})-$, and $-C(=NR_{12})O-$; wherein, $R_{10}$ and $R_{11}$ are independently selected from the group consisting of H, optionally substituted lower alkyl and optionally substituted lower cycloalkyl; or $R_{10}$ and $R_{11}$ may join to form a 5-, 6-, 7- or 8-membered heterocyclic ring;

$R_{12}$ is independently selected from the group consisting of H, $-S(=O)_2R_9$, $-S(=O)_2NH_2$, $-C(O)R_9$, $-CN$, $-NO_2$, heteroaryl, and heteroalkyl; or two $R_{12}$ groups may join to form a 5-, 6-, 7- or 8-membered heterocyclic ring;

$L_4$ is selected from the group consisting of a bond, optionally substituted alkylene, optionally substituted cycloalkylene, optionally substituted heterocycloalkylene-, optionally substituted alkenylene, optionally substituted alkynylene, optionally substituted arylene, and optionally substituted heteroarylene; or $L_3$, X and $L_4$ join to form a nitrogen containing heterocyclic ring;

G is selected from the group consisting of H,

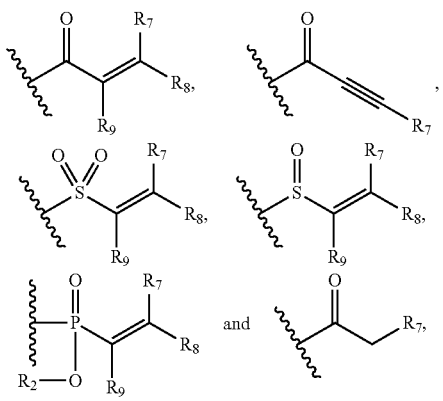

wherein, $R_7$, $R_8$ and $R_9$ are independently selected from the group consisting of H, halogen, optionally substituted lower alkyl, optionally substituted lower heteroalkyl, optionally substituted lower cycloalkyl, and optionally substituted lower heterocycloalkyl;

$R_5$ is selected from the group consisting of H, halogen, -$L_6$-(optionally substituted $C_{1-3}$alkyl), -$L_6$-(optionally substituted $C_{2-4}$alkenyl), -$L_6$-(optionally substituted aryl) and -$L_6$-(optionally substituted heteroaryl), wherein $L_6$ is selected from the group consisting of a bond, O, S, $-S(=O)-$, $-S(=O)_2-$, NH, $-C(=O)-$, $-NHC(O)O-$, $-OC(O)NH-$, $-NHC(O)-$, and $-C(O)NH-$; or $R_5$ is the same as $R_4$.

W is selected from the group consisting of a bond, $-O-$, $-NH-$, $-S-$, $-(CH_2)_m-$, $-(CH_2)_mC_{2-6}$heterocycloalkyl-, $-(CH_2)_nC_{2-6}$heterocycloalkyl-$(CH_2)_n-NR_{13}-$, $-NR_{13}-(CH_2)_n-C_{3-6}$cycloalkyl-$(CH_2)_n-NR_{13}-$, $-(CH_2)_mNR_{13}-$, $-NR_{13}-(CH_2)_m-$, $-(CH_2)_n-NR_{13}-(CH_2)_m-NR_{13}-$, $-NR_{13}-C_{2-6}$alkenyl-, $-NR_{13}-C_{2-6}$alkynyl-, $-NR_{13}$-phenyl-, $-NR_{13}$-phenyl-$NR_{13}-$, $-NR_{13}-(CH_2)_n$-heteroaryl-, $-NR_{13}-(CH_2)_n-C_{2-6}$heterocycloalkyl-, and $-NR_{13}$-heteroaryl-$NR_{13}-$; wherein the said alkenyl, alkynyl, cycloalkyl, heterocycloalkyl, phenyl, heteroaryl, and $(CH_2)$ groups are optionally substituted with one or more substituents selected from $-OH$, halogen, $-OCH_3$ and $C_{1-4}$alkyl;

$R_6$ is selected from the group consisting of H, halogen, $-NH_2$, $-C_{1-8}$alkyl, $-C_{2-8}$alkenyl, $-C_{2-8}$alkynyl, $-(CH_2)_nC_{3-7}$cycloalkyl, $-(CH_2)_nC_{2-9}$heterocycloalkyl, $-(CH_2)_n$-phenyl, $-(CH_2)_n$-naphthyl, $-(CH_2)_n$-heteroaryl, $-(CH_2)_nCO_2H$, $-(CH_2)_n-(CHOH)_n-H$, $-SR_{13}$, $-OR_{13}$, $-COR_{13}$, $-CH_2-N(R_{13})_2$, $-(CH_2)_n-N(R_{13})_2$, $-(CH_2)_n-N(R_{13})CO_2C_{1-8}$alkyl, $-C(O)(CH_2)_n$-aryl, $-C(O)C_{1-8}$alkyl, $-C(O)C_{3-7}$cycloalkyl, $-C(O)C_{2-9}$heterocycloalkyl, $-C(O)(CH_2)_n$-heteroaryl, $-C(O)CF_3$, $-C(O)(CH_2)_n-N(R_{13})_2$, $-C(O)N(R_{13})CO_{1-8}$alkyl, $-CO_2(CH_2)_nC_{3-7}$cycloalkyl, $-C(O)N(R_{13})(CH_2)_nC_{3-7}$cycloalkyl, $-C(O)N(R_{13})(CH_2)_nC_{2-7}$heterocycloalkyl, $-CO_2(CH_2)_n$-heteroaryl, $-CO_2(CH_2)_n$-phenyl, $-C(O)N(R_{13})(CH_2)_n$-phenyl, $-CO_2(CH_2)_n$-naphthyl, $-C(O)N(R_{13})(CH_2)_n$-naphthyl, $-C(O)N(R_{13})(CH_2)_n$-heteroaryl, $-CO_2C_{1-8}$alkyl, $-SO_2C_{1-8}$alkyl, $-C(S)N(R_{13})(CH_2)_n$-phenyl, $-CO_2(CH_2)_nC_{2-9}$heterocycloalkyl, $-SO_2C_{3-7}$cycloalkyl, $-SO_2C_{2-9}$ heterocycloalkyl, $-SO_2$-phenyl, $-SO_2$-naphthyl, $-SO_2$-heteroaryl, $-S(O)N(R_{13})$-phenyl, $-S-C_{1-8}$alkyl, $-S-C_{3-7}$ cycloalkyl, $-S-C_{2-9}$heterocycloalkyl, $-S$-phenyl, $-S$-naphthyl and $-S$-heteroaryl; wherein the said alkyl, alkenyl, alkynyl, cycloalkyl, heterocycloalkyl, aryl, phenyl, naphthyl, heteroaryl, and (CH2) groups are optionally substituted with one or more substituents independently selected from $R_{14}$;

R6 and L4 may join to form a 3- to 12-membered ring;

R13 is selected from the group consisting of H, $-C1-8$alkyl, $-C2-8$alkenyl, $-C2-8$alkynyl, $-(CH2)n$-phenyl, $-C2-8$alkenyl-phenyl and $-(CH2)nCO2H$; wherein the said alkyl, alkenyl, alkynyl, phenyl and $(CH_2)$ groups are optionally substituted with one or more substituents independently selected from the group consisting of $-OC_{1-4}$alkyl and $-C_{1-4}$alkyl;

$R_{14}$ is selected from the group consisting of H, oxo, $=NH$, $-CN$, $-CF_3$, $-OCF_3$, $-C_{1-6}$ alkyl, $-C_{2-6}$alkenyl, $-C_{2-6}$alkynyl, $-(CH_2)_nC_{3-6}$cycloalkyl, $-(CH_2)_nC_{2-9}$heterocycloalkyl, $-(CH_2)_nOR_{13}$, $-(CH_2)_nCO_2R_{13}$, $-(CH_2)_nCO_2(CH_2)_n$-phenyl, $-(CH_2)_n$-phenyl, $-(CH_2)_n$-O-phenyl, $-(CH_2)_n$-naphthyl, $-(CH_2)_n$-heteroaryl, $-N(R_{13})_2$, $-NR_{13}C(O)R_{13}$, $-NR_{13}CO_2R_{13}$, $-C(O)$phenyl, $-C(O)$heteroaryl, $-SR_{13}$, $-SO_2C_{1-6}$alkyl and $-SO_2N(R_{13})_2$; wherein the said alkyl, alkenyl, alkynyl, phenyl, heteroaryl, heterocycloalkyl, naphthyl, cycloalkyl and $(CH_2)$ groups are optionally substituted with one or more substituents independently selected from the group consisting of $-OH$, halogen, $-OCH_3$ and $C_{1-4}$alkyl;

n is 0, 1, 2, 3, 4, 5, 6, 7, or 8;

m is 1, 2, 3, 4, 5, 6, 7, or 8.

Another embodiment of this invention provides a compound of Formula (II)

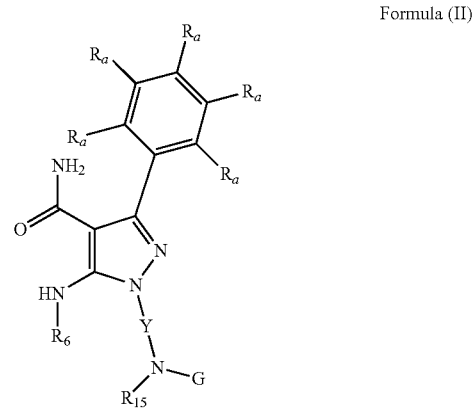

Formula (II)

or a therapeutically acceptable salt, solvate, metabolite, polymorph, ester, tautomer, or prodrug thereof, wherein:

Y is selected from the group consisting of a bond, optionally substituted alkylene and 4- to 6-membered cycloalkyl ring;

$R_a$ is independently selected from the group consisting of H, halogen, —$CF_3$, —CN, —$NO_2$, —OH, —$NH_2$, -$L_a$-(optionally substituted alkyl), -$L_a$-(optionally substituted alkenyl), -$L_a$-(optionally substituted aryl), -$L_a$-(optionally substituted heteroaryl), wherein $L_a$ is selected from the group consisting of a bond, O, S, S(=O), S(=O)$_2$, NH, C(=O), $CH_2$, NHC(O)O, NHC(O) and C(O)NH;

G is selected from the group consisting of H,

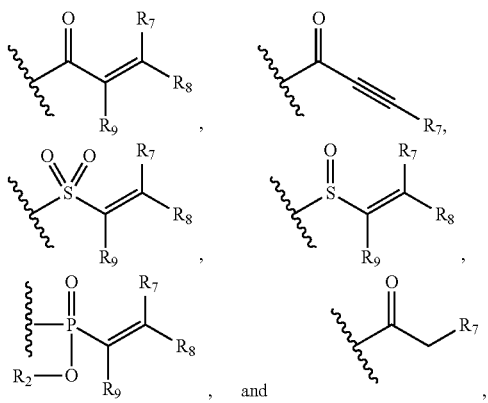

and wherein $R_7$, $R_8$ and $R_9$ are independently selected from the group consisting of H, halogen, optionally substituted lower alkyl, optionally substituted lower heteroalkyl, optionally substituted lower cycloalkyl, and optionally substituted lower heterocycloalkyl;

$R_{15}$ is selected from the group consisting of H and lower alkyl;

Y and $R_{15}$ may join to form a 4-, 5-, or 6-membered heterocyclic ring;

$R_6$ is selected from the group consisting of H, halogen, amino, —$C_{1-8}$alkyl, —$C_{2-8}$ alkenyl, —$C_{2-8}$alkynyl, —$(CH_2)_nC_{3-7}$ cycloalkyl, —$(CH_2)_nC_{2-9}$ heterocycloalkyl, —$(CH_2)_n$-phenyl, —$(CH_2)_n$-naphthyl, —$(CH_2)_n$-heteroaryl, —$(CH_2)_nCO_2H$, —$(CH_2)_n$—$(CHOH)_n$—H, —$COR_{13}$, —$(CH_2)_n$—$N(R_{13})_2$, —$(CH_2)_n$—$N(R_{13})CO_2C_{1-8}$alkyl, —C(O)($CH_2)_n$-aryl, —C(O)$C_{1-8}$alkyl, —C(O)$C_{3-7}$cycloalkyl, —C(O)$C_{2-9}$heterocycloalkyl, —C(O)($CH_2$)-heteroaryl, —C(O)$CF_3$, —C(O)($CH_2$)—$N(R_{13})_2$, —C(O)N($R_{13}$)$C_{1-8}$alkyl, —$CO_2$ $(CH_2)_nC_{3-7}$ cycloalkyl, —C(O)N($R_{13}$)($CH_2$)$_n$$C_{3-7}$ cycloalkyl, —C(O)N($R_{13}$)($CH_2$)$_n$$C_{2-7}$heterocycloalkyl, —$CO_2$ ($CH_2$)$_n$-heteroaryl, —$CO_2$ ($CH_2$)$_n$-phenyl, —C(O)N($R_{13}$)($CH_2$)$_n$-phenyl, —$CO_2$ ($CH_2$)-naphthyl, —C(O)N($R_{13}$)($CH_2$)$_n$-naphthyl, —C(O)N($R_{13}$)($CH_2$)$_n$-heteroaryl, —$CO_2C_{1-8}$alkyl, —$SO_2C_{1-8}$ alkyl, —C(S)N($R_{13}$)($CH_2$)$_n$-phenyl, —$CO_2$($CH_2$)$_n$$C_{2-9}$heterocycloalkyl, —$SO_2C_{3-7}$cycloalkyl, —$SO_2C_{2-9}$ heterocycloalkyl, —$SO_2$phenyl, —$SO_2$naphthyl, —$SO_2$heteroaryl, and —S(O)N($R_{13}$)phenyl; wherein the said alkyl, alkenyl, alkynyl, cycloalkyl, heterocycloalkyl, aryl, phenyl, naphthyl, heteroaryl, and ($CH_2$) groups are optionally substituted with one or more substituents independently selected from $R_{14}$;

$R_6$ and $R_{15}$ may join to form a 3- to 12-membered ring;

$R_{13}$ is selected from the group consisting of H, —$C_{1-8}$alkyl, —$C_{2-8}$alkenyl, —$C_{2-8}$alkynyl, —($CH_2$)-phenyl, —$C_{2-8}$alkenyl-phenyl and —($CH_2$)$_nCO_2H$; wherein the said alkyl, alkenyl, alkynyl, phenyl, and ($CH_2$) groups are optionally substituted with one ore more substituents independently selected from —$OC_{1-4}$alkyl and —$C_{1-4}$alkyl;

$R_{14}$ is selected from the group consisting of H, oxo, =NH, —CN, —$CF_3$, —$OCF_3$, —$C_{1-6}$ alkyl, —$C_{2-6}$alkenyl, —$C_{2-6}$alkynyl, —$(CH_2)_nC_{3-6}$ cycloalkyl, —$(CH_2)_nC_{2-9}$heterocycloalkyl, —$(CH_2)_nOR_{13}$, —$(CH_2)_nCO_2R_{13}$, —$(CH_2)_nCO_2(CH_2)_n$-phenyl, —$(CH_2)_n$-phenyl, —$(CH_2)$—O-phenyl, —$(CH_2)_n$-naphthyl, —$(CH_2)_n$-heteroaryl, —$N(R_{13})_2$, —$NR_3C(O)R_{13}$, —$NR_{13}CO_2R_{13}$, —C(O)phenyl, —C(O)heteroaryl, —$SR_{13}$, —$SO_2C_{1-6}$alkyl and —$SO_2N(R_{13})_2$; wherein the said alkyl, alkenyl, alkynyl, phenyl, heteroaryl, heterocycloalkyl, naphthyl, cycloalkyl and ($CH_2$) groups are optionally substituted with one or more substituents independently selected from the group consisting of —OH, halogen, —$OCH_3$ and $C_{1-4}$alkyl;

n is 0, 1, 2, 3, 4, 5, 6, 7, or 8;

m is 1, 2, 3, 4, 5, 6, 7, or 8.

In some embodiments, the compounds of the invention are those represented by formula (II), wherein G is selected from the group consisting of

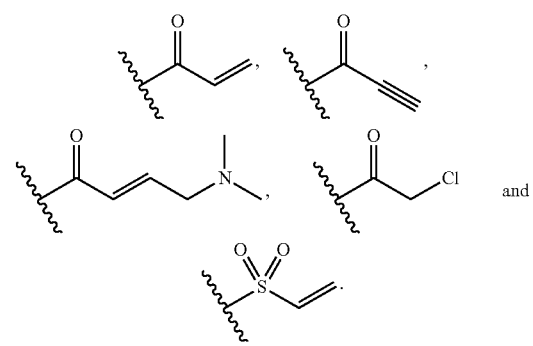

In some embodiments, the compounds of the invention are those represented by formula (II), wherein

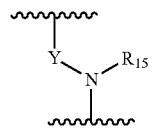

is selected from the group consisting of

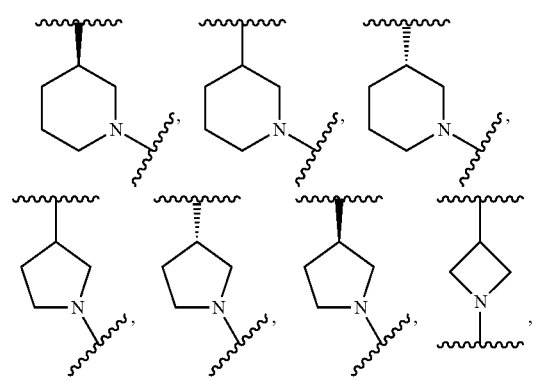

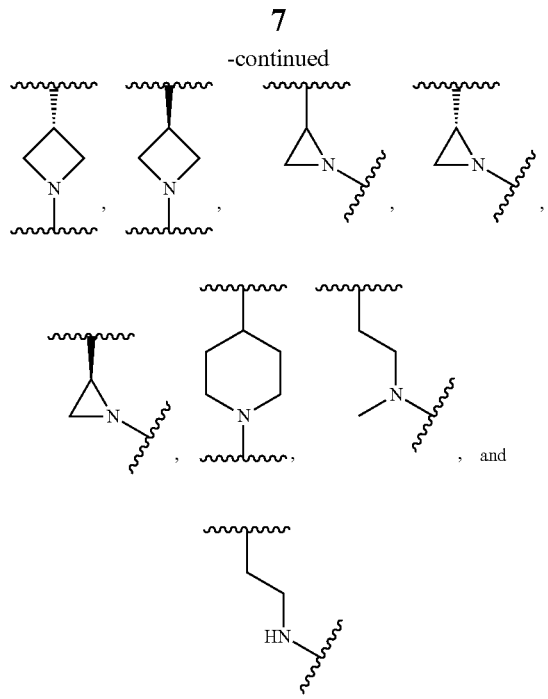

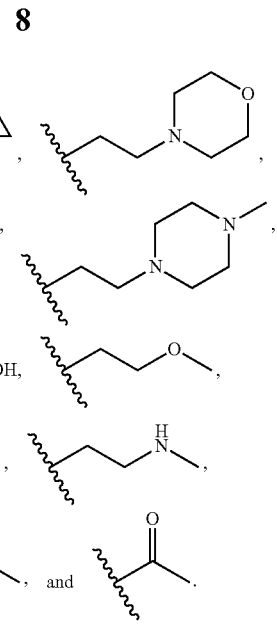

In some embodiments, the compounds of the invention are those represented by formula (II), wherein

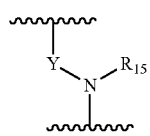

is selected from the group consisting of

Another embodiment of this invention provides a compound of Formula (III),

Formula (III)

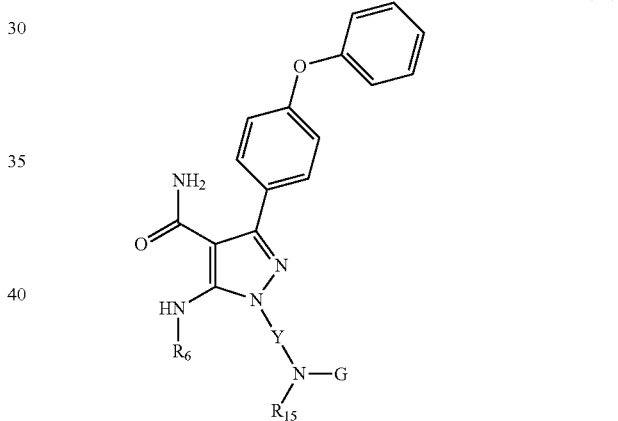

or a therapeutically acceptable salt, solvate, metabolite, polymorph, ester, tautomer, or prodrug thereof, wherein:

Y is selected from the group consisting of a bond, optionally substituted alkyl and a 4-, 5-, or 6-membered cycloalkyl ring;

$R_{15}$ is selected from the group consisting of H and lower alkyl; or

Y and $R_{15}$ may join to form a 4-, 5-, or 6-membered heterocyclic ring;

G is selected from the group consisting of H,

In some embodiments, the compounds of the invention are those represented by formula (II), wherein $R_6$ is selected from the group consisting of H, Me, Et, -continued

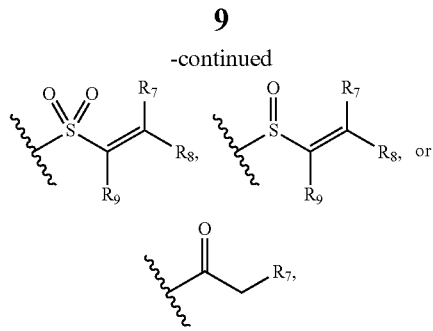

wherein R₇, R₈ and R₉ are independently selected from the group consisting of H, halogen, optionally substituted lower alkyl, and optionally substituted lower heteroalkyl;

R₆ is selected from the group consisting of H, —C₁₋₈alkyl, —(CH₂)ₙC₃₋₇cycloalkyl, —(CH₂)ₙC₂₋₉heterocycloalkyl, —(CH₂)ₙ—OH, —(CH₂)ₙ—(CHOH)ₙ—H, —(CH₂)ₙ—O—(CH₂)ₙCH₃, —(CH₂)ₙ—S—(CH₂)ₙCH₃, —(CH₂)ₙ—NH₂, —(CH₂)ₙ—NH(C₁₋₈ alkyl), —(CH₂)ₙ—N(C₁₋₈ alkyl)₂, and —C(O)C₁₋₈ alkyl;

n is 0, 1, 2, 3, or 4.

In some embodiments, the compounds of the invention are those represented by formula (III), wherein

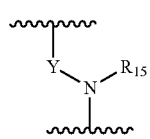

is selected from the group consisting of

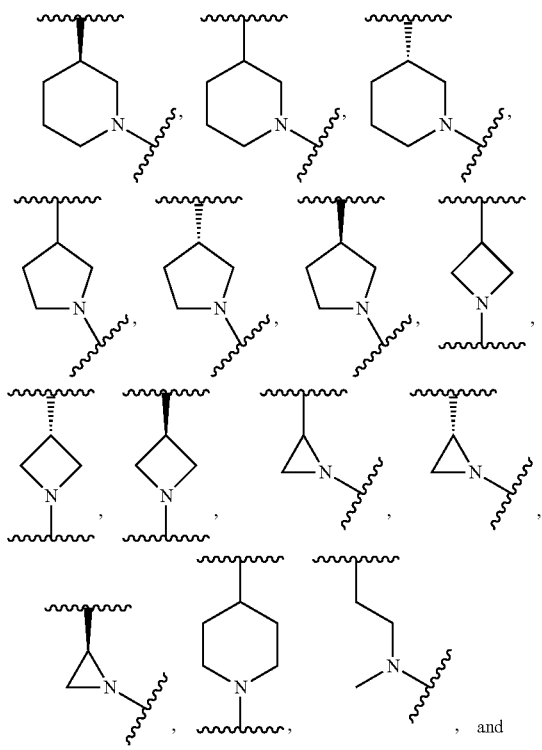
, and

-continued

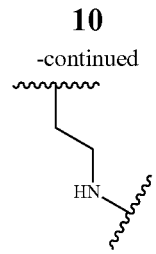

In some embodiments, the compounds of the invention are those represented by formula (III), wherein

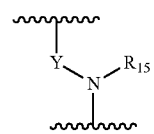

is selected from the group consisting of

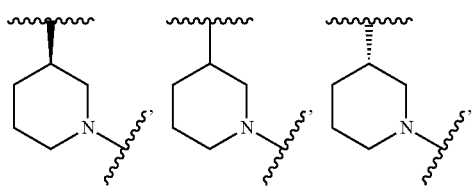

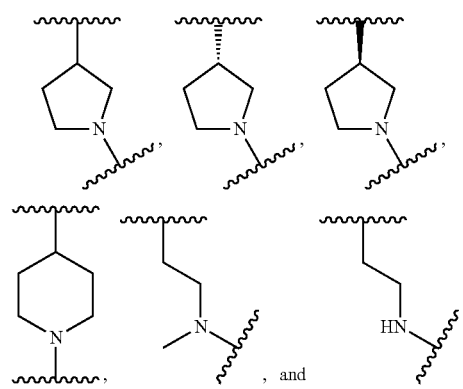
, and

In some embodiments, the compounds of the invention are those represented by formula (III), wherein G is selected from the group consisting of

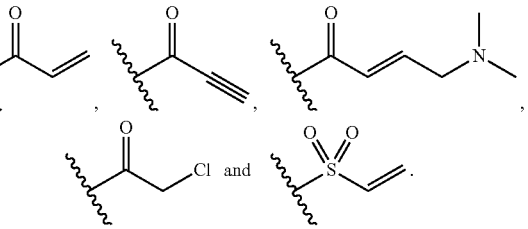

In some embodiments, the compounds of the invention are those represented by formula (III), wherein R₆ is selected from the group consisting of H, Me, Et,

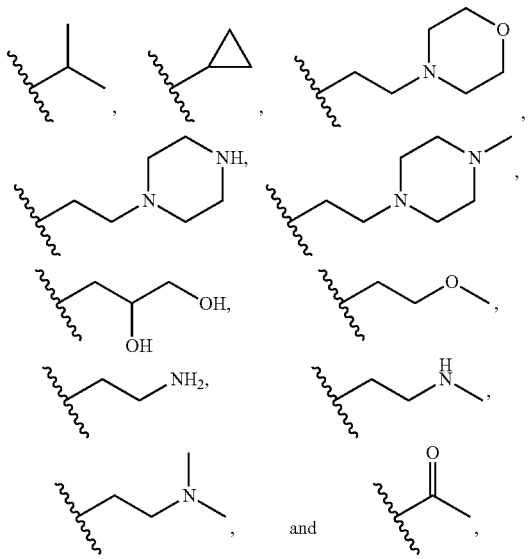

Another embodiment of this invention provides a compound of Formula (IV),

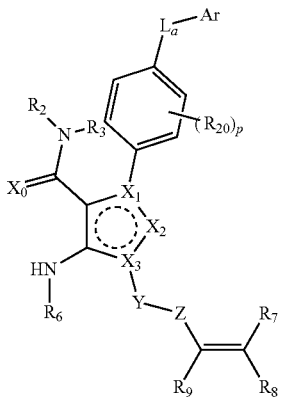

Formula (IV)

or a therapeutically acceptable salt, solvate, metabolite, polymorph, ester, tautomer, or prodrug thereof, wherein:

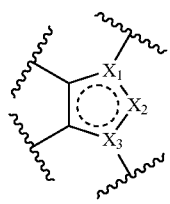

is an aromatic ring;

$L_a$ is selected from the group consisting of a bond, O, S, NH, S(=O), S(=O)$_2$, C(=O), CH$_2$, NHC(O)O, NHC(O) and C(O)NH;

$X_0$ is selected from the group consisting of CH$_2$, O, NH and S;

$X_1$ and $X_3$ are independently selected from the group consisting of C and N;

$X_2$ is selected from the group consisting of CR$_5$, N, and NR$_5$;

$R_5$ is selected from the group consisting of H, halogen, -L$_6$-(C$_{1-3}$alkyl), -L$_6$-(C$_{2-4}$alkenyl), -L$_6$-(aryl), -L$_6$-(heteroaryl) and

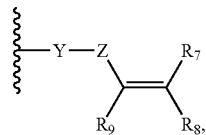

wherein L$_6$ is selected from the group consisting of a bond, O, S, —S(=O)—, —S(=O)$_2$—, NH, C(=O), —NHC(O)O—, —OC(O)NH—, —NHC(O)—, and —C(O)NH—, and said alkyl, alkenyl, aryl, and heteroaryl are optionally substituted with one or more substituents independently selected from the group consisting of lower alkyl, lower cycloalkyl, lower heteroalkyl, and lower heterocycloalkyl;

$R_{20}$ is independently selected from the group consisting of H, and lower alkyl, wherein the lower alkyl is optionally substituted with one or more substituents independently selected from the group consisting of lower heteroalkyl, lower cycloalkyl, and lower heterocycloalkyl;

$R_2$ and $R_3$ are independently selected from the group consisting of H, and lower alkyl, wherein the lower alkyl is optionally substituted with one or more substituents independently selected from the group consisting of lower heteroalkyl, lower cycloalkyl, and lower heterocycloalkyl; or $R_2$ and $R_3$ may join to form a 3- to 8-membered heterocyclic ring;

Ar is selected from the group consisting of aryl and heteroaryl, wherein the aryl and heteroaryl are optionally substituted with one or more substituents independently selected from the group consisting of H, NO$_2$, OH, NH$_2$, OMe, CF$_3$, halogen, lower alkyl, lower heteroalkyl, lower cycloalkyl, and lower heterocycloalkyl;

Y is selected from the group consisting of a bond, alkylene, heteroalkylene, cycloalkylene, heterocycloalkylene, arylene, and heteroarylene;

Z is selected from the group consisting of C(=O), OC(=O), NHC(=O), C(=S), S(=O)$_r$, OS(=O)$_r$, and NHS(=O)$_r$, wherein r is 1 or 2;

$R_6$ is selected from the group consisting of H, halogen, —NH$_2$, —C$_{1-8}$alkyl, —C$_{2-8}$ alkenyl, —C$_{2-8}$alkynyl, —(CH$_2$)$_n$C$_{3-7}$ cycloalkyl, —(CH$_2$)$_n$C$_{2-9}$ heterocycloalkyl, —(CH$_2$)$_n$-phenyl, —(CH$_2$)$_n$-naphthyl, —(CH$_2$)$_n$-heteroaryl, —(CH$_2$)$_n$CO$_2$H, —(CH$_2$)n-(CHOH)n-H, —SR$_{13}$, —OR$_{13}$, —COR$_{13}$, =CH—N(R$_{13}$)$_2$, —(CH$_2$)$_n$—N(R$_{13}$)$_2$, —(CH$_2$)$_n$—N(R$_{13}$)CO$_2$C$_{1-8}$alkyl, —C(O)(CH$_2$)$_n$-aryl, —C(O)C$_{1-8}$alkyl, —C(O)C$_{3-7}$cycloalkyl, —C(O)C$_{2-9}$heterocycloalkyl, —C(O)(CH$_2$)$_n$-heteroaryl, —C(O)CF$_3$, —C(O)(CH$_2$)$_n$—N(R$_{13}$)$_2$, —C(O)N(R$_{13}$)C$_{1-8}$alkyl, —CO$_2$(CH$_2$)$_n$C$_{3-7}$cycloalkyl, —C(O)N(R$_{13}$)(CH$_2$)$_n$C$_{3-7}$cycloalkyl, —C(O)N(R$_{13}$)(CH$_2$)$_n$C$_{2-7}$heterocycloalkyl, —CO$_2$ (CH$_2$)$_n$-heteroaryl, —CO$_2$ (CH$_2$)$_n$-phenyl, —C(O)N(R$_{13}$)(CH$_2$)$_n$-phenyl, —CO$_2$(CH$_2$)$_n$-naphthyl, —C(O)N(R$_{13}$)(CH$_2$)$_n$-naphthyl, —C(O)N(R$_{13}$)(CH$_2$)$_n$-heteroaryl, —CO$_2$C$_{1-8}$alkyl, —SO$_2$C$_{1-8}$ alkyl, —C(S)N(R$_{13}$)(CH$_2$)$_n$-phenyl, —CO$_2$(CH$_2$)$_n$C$_{2-9}$heterocycloalkyl, —SO$_2$C$_{3-7}$cycloalkyl, —SO$_2$C$_{2-9}$ heterocycloalkyl, —SO$_2$phenyl, —SO$_2$naphthyl, —SO$_2$heteroaryl, —S(O)N(R$_{13}$)phenyl, —S—C$_{1-8}$ alkyl, —S—C$_{3-7}$ cycloalkyl, —S—C$_{2-9}$heterocycloalkyl, —S-phenyl, —S-naphthyl and —S-heteroaryl; wherein the said alkyl, alkenyl, alkynyl, cycloalkyl, heterocycloalkyl, aryl, phenyl, naphthyl, heteroaryl, and (CH$_2$)

groups are optionally substituted with one or more substituents independently selected from $R_{14}$;

$R_6$ and Y may join to form a 3- to 12-membered ring;

$R_7$ is selected from the group consisting of H, $C_{1-4}$alkyl, $C_{1-4}$heteroalkyl, $C_{1-6}$alkoxyalkyl, $C_{1-8}$alkylaminoalkyl, $C_{3-6}$cycloalkyl, aryl, $C_{2-8}$ heterocycloalkyl, heteroaryl, $C_{1-4}$ alkyl(aryl), $C_{1-4}$ alkyl(heteroaryl), $C_{1-4}$ alkyl($C_{3-8}$ cycloalkyl), and $C_{1-4}$ alkyl($C_{2-8}$ heterocycloalkyl), wherein said alkyl, heteroalkyl, alkoxyalkyl, cycloalkyl, aryl, heterocycloalkyl, and heteroaryl are optionally substituted with one or more substituents independently selected from the group consisting of H, OH, $NH_2$, OMe, $CF_3$, halogen, lower alkyl, lower heteroalkyl, lower cycloalkyl, and lower heterocycloalkyl;

$R_8$ and $R_9$ are independently selected from the group consisting of H, $C_{1-4}$alkyl, $C_{1-4}$heteroalkyl, $C_{3-6}$cycloalkyl, and $C_{2-6}$heterocycloalkyl, wherein said alkyl, heteroalkyl, cycloalkyl, and heterocycloalkyl are optionally substituted with one or more substituents independently selected from the group consisting of H, OH, $NH_2$, OMe, $CF_3$, halogen, lower alkyl, lower heteroalkyl, lower cycloalkyl, and lower heterocycloalkyl; or $R_8$ and $R_9$ may join to form a bond;

$R_{13}$ is selected from the group consisting of H, —$C_{1-8}$alkyl, —$C_{2-8}$alkenyl, —$C_{2-8}$alkynyl, —$(CH_2)$-phenyl, —$C_{2-8}$alkenyl-phenyl and —$(CH_2)_nCO_2H$; wherein the said alkyl, alkenyl, alkynyl, phenyl, and $(CH_2)$ groups are optionally substituted with one or more substituents independently selected from —$OC_{1-4}$alkyl and —$C_{1-4}$alkyl;

$R_{14}$ is selected from the group consisting of H, oxo, =NH, —CN, —$CF_3$, —$OCF_3$, —$C_{1-6}$ alkyl, —$C_{2-6}$alkenyl, —$C_{2-6}$alkynyl, —$(CH_2)_nC_{3-6}$ cycloalkyl, —$(CH_2)_nC_{2-9}$heterocycloalkyl, —$(CH_2)_nOR_{13}$, —$(CH_2)_nCO_2R_{13}$, —$(CH_2)_nCO_2(CH_2)_n$-phenyl, —$(CH_2)_n$-phenyl, —$(CH_2)$—O-phenyl, —$(CH_2)_n$-naphthyl, —$(CH_2)_n$-heteroaryl, —$N(R_{13})_2$, —$NR_{13}C(O)R_{13}$, —$NR_{13}CO_2R_{13}$, —C(O)phenyl, —C(O)heteroaryl, —$SR_{13}$, —$SO_2C_{1-6}$alkyl and —$SO_2N(R_{13})_2$; wherein the said alkyl, alkenyl, alkynyl, phenyl, heteroaryl, heterocycloalkyl, naphthyl, cycloalkyl and $(CH_2)$ groups are optionally substituted with one or more substituents independently selected from the group consisting of —OH, halogen, —$OCH_3$ and $C_{1-4}$alkyl;

n is 0, 1, 2, 3, 4, 5, 6, 7, or 8;

p is 0, 1, 2, 3, or 4.

In some embodiments, the compounds of the invention are those represented by formula (IV), wherein $R_8$ and $R_9$ are independently selected from the group consisting of H, $C_{1-4}$alkyl, and $C_{1-4}$heteroalkyl, wherein the said alkyl and heteroalkyl are optionally substituted with one or more substituents independently selected from the group consisting of OH, $NH_2$, $CF_3$, halogen, lower alkyl, and lower heteroalkyl; or $R_8$ and $R_9$ may join to form a bond.

In some embodiments, the compounds of the invention are those represented by formula (IV), wherein $R_8$ and $R_9$ are independently selected from the group consisting of H, $C_{1-4}$alkyl, and $C_{1-4}$heteroalkyl; or $R_8$ and $R_9$ may join to form a bond.

In some embodiments, the compounds of the invention are those represented by formula (IV), wherein $R_8$ and $R_9$ are both H; or $R_8$ and $R_9$ may join to form a bond.

In some embodiments, the compounds of the invention are those represented by formula (IV), wherein $R_7$ is selected from the group consisting of H, $C_{1-4}$alkyl, $C_{1-4}$heteroalkyl, and $C_{1-8}$alkylaminoalkyl, wherein the said alkyl and heteroalkyl are optionally substituted with one or more substituents independently selected from the group consisting of OH, $NH_2$, $CF_3$, halogen, lower alkyl, and lower heteroalkyl.

In some embodiments, the compounds of the invention are those represented by formula (IV), wherein $R_7$ is selected from the group consisting of H, $C_{1-4}$alkyl, $C_{1-4}$heteroalkyl, and $C_{1-8}$ alkylaminoalkyl.

In some embodiments, the compounds of the invention are those represented by formula (IV), wherein $R_7$ is H.

In some embodiments, the compounds of the invention are those represented by formula (IV), wherein Z is selected from the group consisting of C(=O), S(=O)$_2$, and S(=O).

In some embodiments, the compounds of the invention are those represented by formula (IV), wherein Z is selected from the group consisting of C(=O) and S(=O)$_2$.

In some embodiments, the compounds of the invention are those represented by formula (IV), wherein Y is selected from the group consisting of $C_{1-8}$alkyl, $C_{2-9}$heteroalkyl, aryl, heteroaryl, 4- to 7-membered cycloalkyl, and 4- to 7-membered heterocycloalkyl, wherein the said alkyl, heteroalkyl, aryl, heteroaryl, cycloalkyl, and heterocycloalkyl are optionally substituted with one or more substituents independently selected from the group consisting of OH, $NH_2$, $CF_3$, halogen, lower alkyl, and lower heteroalkyl.

In some embodiments, the compounds of the invention are those represented by formula (IV), wherein Y is selected from the group consisting of $C_{1-8}$alkyl, $C_{2-9}$heteroalkyl, aryl, heteroaryl, 4- to 7-membered cycloalkyl, and 4- to 7-membered heterocycloalkyl.

In some embodiments, the compounds of the invention are those represented by formula (IV), wherein Y is selected from the group consisting of $C_{1-8}$alkyl, 4- to 7-membered cycloalkyl and 4- to 7-membered heterocycloalkyl.

In some embodiments, the compounds of the invention are those represented by formula (IV), wherein Y is selected from the group consisting of

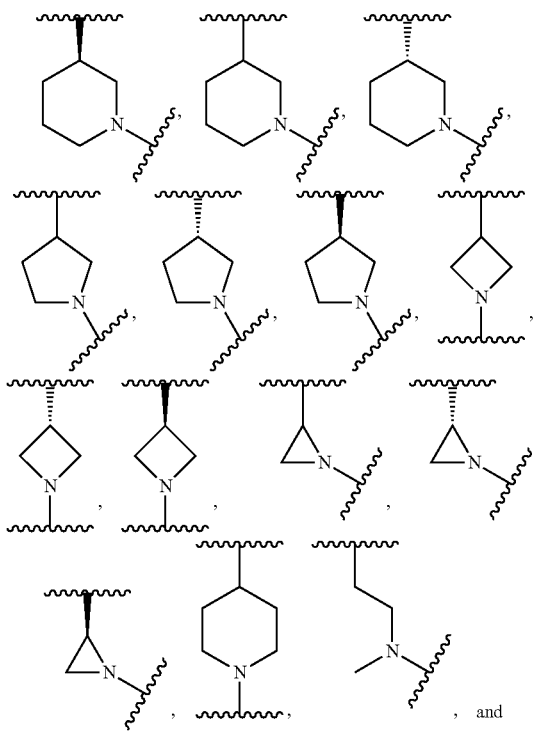

, and

-continued

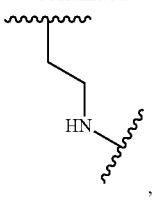

wherein the said

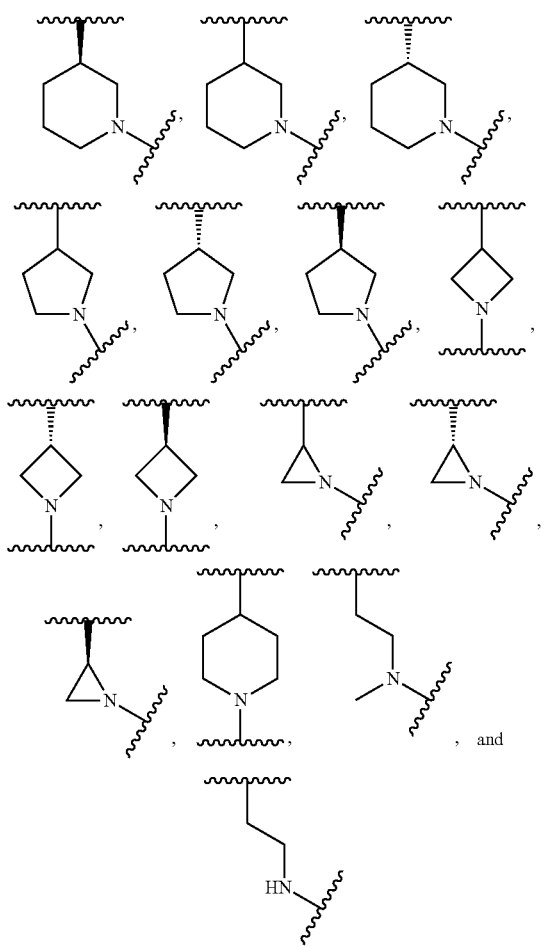

groups are optionally substituted with one or more substituents independently selected from the group consisting of OH, NH₂, CF₃, halogen, lower alkyl, and lower heteroalkyl.

In some embodiments, the compounds of the invention are those represented by formula (IV), wherein Y is selected from the group consisting of -continued

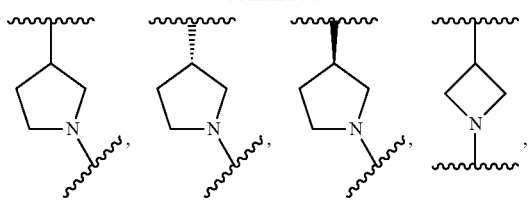

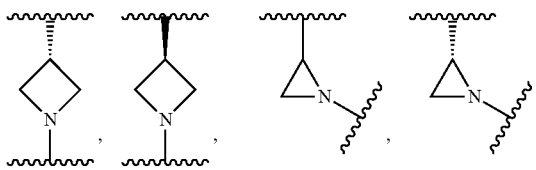

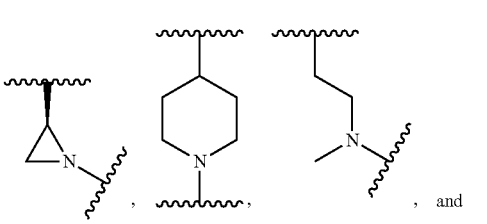

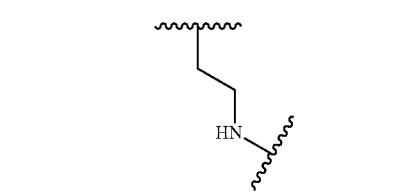

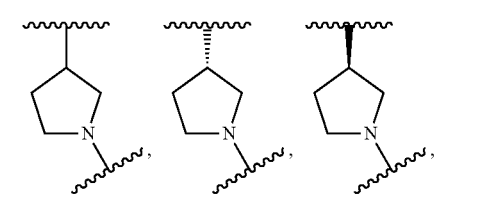

In some embodiments, the compounds of the invention are those represented by formula (IV), wherein Y is selected from the group consisting of

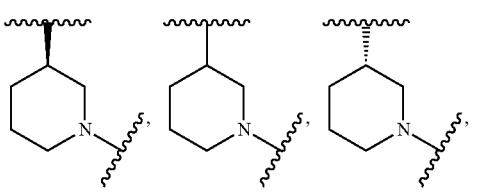

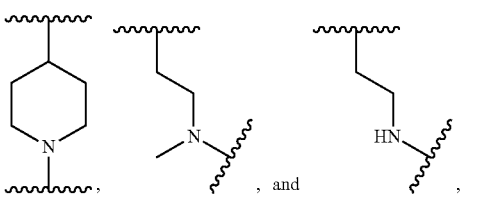

wherein the said

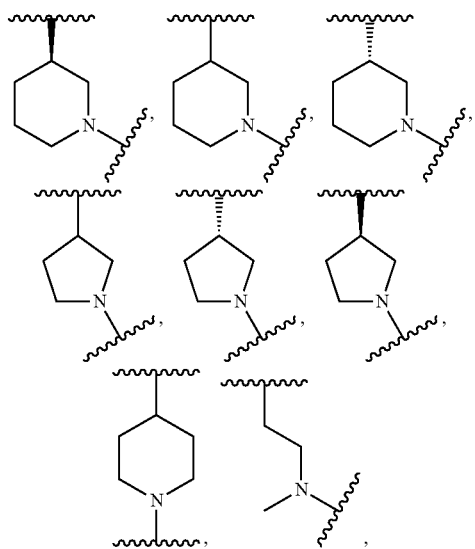

groups are optionally substituted with one or more substituents independently selected from the group consisting of OH, NH$_2$, CF$_3$, halogen, lower alkyl, and lower heteroalkyl.

In some embodiments, the compounds of the invention are those represented by formula (IV), wherein Y is selected from the group consisting of

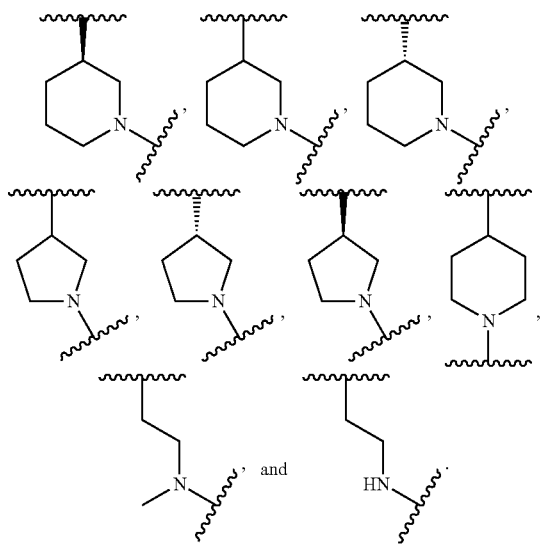

In some embodiments, the compounds of the invention are those represented by formula (IV), wherein X$_1$ is C, X$_2$ and X$_3$ are N; or X$_1$ is N, X$_2$ is CH, and X$_3$ is C; or X$_1$ is C, X$_2$ is CH, and X$_3$ is N.

In some embodiments, the compounds of the invention are those represented by formula (IV), wherein X$_1$ is C, X$_2$ and X$_3$ are N.

In some embodiments, the compounds of the invention are those represented by formula (IV), wherein L$_a$ is selected from the group consisting of O, S and NH.

In some embodiments, the compounds of the invention are those represented by formula (IV), wherein L$_a$ is O.

In some embodiments, the compounds of the invention are those represented by formula (IV), wherein Ar is aryl or heteroaryl.

In some embodiments, the compounds of the invention are those represented by formula (IV), wherein Ar is phenyl.

In some embodiments, the compounds of the invention are those represented by formula (IV), wherein X$_0$ is selected from the group consisting of O, S and NH.

In some embodiments, the compounds of the invention are those represented by formula (IV), wherein X$_0$ is O.

In some embodiments, the compounds of the invention are those represented by formula (IV), wherein R$_2$ and R$_3$ are independently selected from the group consisting of H and C$_{1-4}$alkyl; or R$_2$ and R$_3$ join to form a 3- to 8-membered heterocyclic ring.

In some embodiments, the compounds of the invention are those represented by formula (IV), wherein R$_2$ and R$_3$ are H; or R$_2$ is H, and R$_3$ is C$_{1-4}$alkyl; or R$_3$ is H, and R$_2$ is C$_{1-4}$alkyl.

In some embodiments, the compounds of the invention are those represented by formula (IV), wherein R$_6$ is selected from the group consisting of H, —C$_{1-8}$alkyl, —(CH$_2$)$_n$C$_{3-7}$cycloalkyl, —(CH$_2$)$_n$C$_{2-9}$heterocycloalkyl, —(CH$_2$)$_n$—OH, —(CH$_2$)$_n$(CHOH)$_n$—H, —(CH$_2$)$_n$—O—(CH$_2$)$_n$CH$_3$, —(CH$_2$)$_n$—S—(CH$_2$)$_n$CH$_3$, —(CH$_2$)$_n$—NH$_2$, —(CH$_2$)$_n$—NH(C$_{1-8}$alkyl), —(CH$_2$)$_n$—N(C$_{1-8}$alkyl)$_2$, —C(O)CF$_3$, —C(O)C$_{1-8}$alkyl, —(CH$_2$)$_n$-phenyl, and —(CH$_2$)$_n$-heteroaryl.

In some embodiments, the compounds of the invention are those represented by formula (IV), wherein R$_6$ is selected from the group consisting of H, —C$_{1-8}$alkyl, —(CH$_2$)$_n$C$_{3-7}$cycloalkyl, —(CH$_2$)$_n$C$_{2-9}$heterocycloalkyl, —(CH$_2$)$_n$—OH, —(CH$_2$)$_n$(CHOH)$_n$—H, —(CH$_2$)$_n$—O—(CH$_2$)$_n$CH$_3$, —(CH$_2$)$_n$—S—(CH$_2$)$_n$CH$_3$, —(CH$_2$)$_n$—NH$_2$, —(CH$_2$)$_n$—NH(C$_{1-8}$alkyl), —(CH$_2$)$_n$—N(C$_{1-8}$alkyl)$_2$, and —C(O)C$_{1-8}$alkyl.

In some embodiments, the compounds of the invention are those represented by formula (IV), wherein R$_6$ is selected from the group consisting of H, Me, Et,

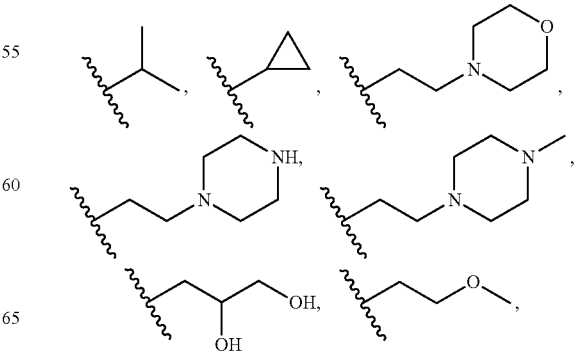

and

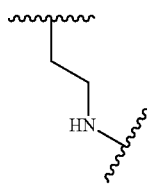

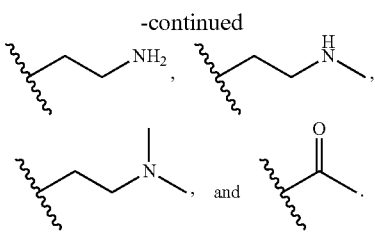

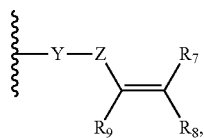

In some embodiments, the compounds of the invention are those represented by formula (IV), wherein n=0, 1, 2, 3, 4, 5, or 6.

In some embodiments, the compounds of the invention are those represented by formula (IV), wherein n=0, 1, 2, 3, or 4.

In some embodiments, the compounds of the invention are those represented by formula (IV), wherein p=0, 1, or 2.

Another embodiment of this invention provides a compound of Formula (V),

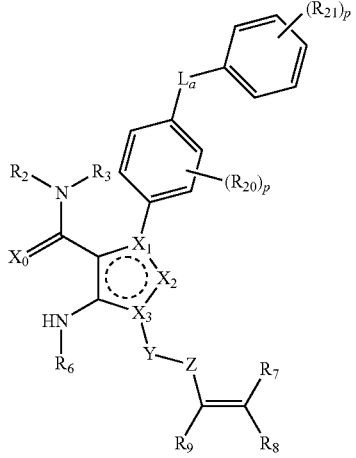

Formula (V)

or a therapeutically acceptable salt, solvate, metabolite, polymorph, ester, tautomer, or prodrug thereof, wherein:

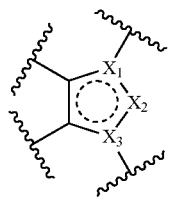

is an aromatic ring;

$L_a$ is selected from the group consisting of a bond, O, S, NH, S(=O), S(=O)$_2$, C(=O), CH$_2$, NHC(O)O, NHC(O) and C(O)NH;

$X_0$ is selected from the group consisting of CH$_2$, O, NH and S;

$X_1$ and $X_3$ are independently selected from the group consisting of C and N;

$X_2$ is selected from the group consisting of CR$_5$, N, and NR$_5$;

$R_5$ is selected from the group consisting of H, halogen, -L$_6$-(C$_{1-3}$alkyl), -L$_6$-(C$_{2-4}$alkenyl), -L$_6$-(aryl), -L$_6$-(heteroaryl) and wherein $L_6$ is selected from the group consisting of a bond, O, S, —S(=O)—, —S(=O)$_2$—, NH, C(=O), —NHC(O)O—, —OC(O)NH—, —NHC(O)—, and —C(O)NH—, and said alkyl, alkenyl, aryl, and heteroaryl are optionally substituted with one or more substituents independently selected from the group consisting of lower alkyl, lower cycloalkyl, lower heteroalkyl, and lower heterocycloalkyl;

$R_2$ and $R_3$ are independently selected from the group consisting of H, and lower alkyl, wherein the lower alkyl is optionally substituted with one or more substituents independently selected from the group consisting of lower heteroalkyl, lower cycloalkyl, and lower heterocycloalkyl; or $R_2$ and $R_3$ may join to form a 3- to 8-membered heterocyclic ring;

$R_{20}$ is independently selected from the group consisting of H, and lower alkyl, wherein the lower alkyl is optionally substituted with one or more substituents independently selected from the group consisting of lower heteroalkyl, lower cycloalkyl, and lower heterocycloalkyl;

$R_{21}$ is selected from the group consisting of H, NO$_2$, OH, NH$_2$, OMe, CF$_3$, halogen, lower alkyl, lower heteroalkyl, lower cycloalkyl, and lower heterocycloalkyl, wherein the said alkyl, heteroalkyl, cycloalkyl, and heterocycloalkyl are optionally substituted with one or more substituents independently selected from the group consisting of H, OH, NH$_2$, OMe, CF$_3$, halogen, lower alkyl, lower heteroalkyl, lower cycloalkyl, and lower heterocycloalkyl;

Y is selected from the group consisting of a bond, alkylene, heteroalkylene, cycloalkylene, heterocycloalkylene, arylene, and heteroarylene;

Z is selected from the group consisting of C(=O), OC(=O), NHC(=O), C(=S), S(=O)$_r$, OS(=O)$_r$, and NHS(=O)$_r$, wherein r is 1 or 2;

$R_6$ is selected from the group consisting of H, halogen, —NH$_2$, —C$_{1-8}$alkyl, —C$_{2-8}$alkenyl, —C$_{2-8}$alkynyl, —(CH$_2$)$_n$C$_{3-7}$cycloalkyl, —(CH$_2$)$_n$C$_{2-9}$heterocycloalkyl, —(CH$_2$)$_n$-phenyl, —(CH$_2$)$_n$-naphthyl, —(CH$_2$)$_n$-heteroaryl, —(CH$_2$)$_n$CO$_2$H, —(CH$_2$)n-(CHOH)n-H, —SR$_{13}$, —OR$_{13}$, —COR$_{13}$, =CH—N(R$_{13}$)$_2$, —(CH$_2$)$_n$—N(R$_{13}$)$_2$, —(CH$_2$)$_n$—N(R$_{13}$)CO$_2$C$_{1-8}$alkyl, —C(O)(CH$_2$)$_n$-aryl, —C(O)C$_{1-8}$alkyl, —C(O)C$_{3-7}$cycloalkyl, —C(O)C$_{2-9}$heterocycloalkyl, —C(O)(CH$_2$)$_n$-heteroaryl, —C(O)CF$_3$, —C(O)(CH$_2$)$_n$—N(R$_{13}$)$_2$, —C(O)N(R$_{13}$)C$_{1-8}$alkyl, —CO$_2$(CH$_2$)$_n$C$_{3-7}$cycloalkyl, —C(O)N(R$_{13}$)(CH$_2$)$_n$C$_{3-7}$cycloalkyl, —C(O)N(R$_{13}$)(CH$_2$)$_n$C$_{2-7}$heterocycloalkyl, —CO$_2$(CH$_2$)$_n$-heteroaryl, —CO$_2$(CH$_2$)$_n$-phenyl, —C(O)N(R$_{13}$)(CH$_2$)$_n$-phenyl, —CO$_2$(CH$_2$)$_n$-naphthyl, —C(O)N(R$_{13}$)(CH$_2$)$_n$-naphthyl, —C(O)N(R$_{13}$)(CH$_2$)$_n$-heteroaryl, —CO$_2$C$_{1-8}$alkyl, —SO$_2$C$_{1-8}$alkyl, —C(S)N(R$_{13}$)(CH$_2$)$_n$-phenyl, —CO$_2$(CH$_2$)$_n$C$_{2-9}$heterocycloalkyl, —SO$_2$C$_{3-7}$cycloalkyl, —SO$_2$C$_{2-9}$heterocycloalkyl, —SO$_2$phenyl, —SO$_2$naphthyl, —SO$_2$heteroaryl, —S(O)N(R$_{13}$)phenyl, —S—C$_{1-8}$alkyl, —S—C$_{3-7}$cycloalkyl, —S—C$_{2-9}$heterocycloalkyl, —S-phenyl, —S-naphthyl and —S-heteroaryl; wherein the said alkyl, alkenyl, alkynyl, cycloalkyl, heterocycloalkyl, aryl, phenyl, naphthyl, heteroaryl, and (CH$_2$) groups are optionally substituted with one or more substituents independently selected from R$_{14}$;

$R_6$ and Y may join to form a 3- to 12-membered ring;

R₇ is selected from the group consisting of H C$_{1-4}$alkyl, C$_{1-4}$heteroalkyl, C$_{1-6}$alkoxyalkyl, C$_{1-8}$alkylaminoalkyl, C$_{3-6}$cycloalkyl, aryl, C$_{2-8}$ heterocycloalkyl, heteroaryl, C$_{1-4}$alkyl(aryl), C$_{1-4}$alkyl(heteroaryl), C$_{1-4}$alkyl(C$_{3-8}$cycloalkyl), and C$_{1-4}$alkyl(C$_{2-8}$heterocycloalkyl), wherein said alkyl, heteroalkyl, alkoxyalkyl, cycloalkyl, aryl, heterocycloalkyl, and heteroaryl are optionally substituted with one or more substituents independently selected from the group consisting of H, OH, NH$_2$, OMe, CF$_3$, halogen, lower alkyl, lower heteroalkyl, lower cycloalkyl, and lower heterocycloalkyl;

R$_8$ and R$_9$ are independently selected from the group consisting of H, C$_{1-4}$alkyl, C$_{1-4}$heteroalkyl, C$_{3-6}$cycloalkyl, and C$_{2-6}$heterocycloalkyl, wherein said alkyl, heteroalkyl, cycloalkyl, and heterocycloalkyl are optionally substituted with one or more substituents independently selected from the group consisting of H, OH, NH$_2$, OMe, CF$_3$, halogen, lower alkyl, lower heteroalkyl, lower cycloalkyl, and lower heterocycloalkyl; or R$_8$ and R$_9$ may join to form a bond;

R$_{13}$ is selected from the group consisting of H, —C$_{1-8}$alkyl, —C$_{2-8}$alkenyl, —C$_{2-8}$alkynyl, —(CH$_2$)-phenyl, —C$_{2-8}$alkenyl-phenyl and —(CH$_2$)$_n$CO$_2$H; wherein the said alkyl, alkenyl, alkynyl, phenyl, and (CH$_2$) groups are optionally substituted with one or more substituents independently selected from —OC$_{1-4}$alkyl and —C$_{1-4}$alkyl;

R$_{14}$ is selected from the group consisting of H, oxo, =NH, —CN, —CF$_3$, —OCF$_3$, —C$_{1-6}$alkyl, —C$_{2-6}$alkenyl, —C$_{2-6}$alkynyl, —(CH$_2$)$_n$C$_{3-6}$cycloalkyl, —(CH$_2$)$_n$C$_{2-9}$heterocycloalkyl, —(CH$_2$)$_n$OR$_{13}$, —(CH$_2$)$_n$CO$_2$R$_{13}$, —(CH$_2$)$_n$CO$_2$(CH$_2$)$_n$-phenyl, —(CH$_2$)$_n$-phenyl, —(CH$_2$)—O-phenyl, —(CH$_2$)$_n$-naphthyl, —(CH$_2$)$_n$-heteroaryl, —N(R$_{13}$)$_2$, —NR$_{13}$C(O)R$_{13}$, —NR$_{13}$CO$_2$R$_{13}$, —C(O)phenyl, —C(O)heteroaryl, —SR$_{13}$, —SO$_2$C$_{1-6}$alkyl and —SO$_2$N(R$_{13}$)$_2$; wherein the said alkyl, alkenyl, alkynyl, phenyl, heteroaryl, heterocycloalkyl, naphthyl, cycloalkyl and (CH$_2$) groups are optionally substituted with one or more substituents independently selected from the group consisting of —OH, halogen, —OCH$_3$ and C$_{1-4}$alkyl;

n is 0, 1, 2, 3, 4, 5, 6, 7, or 8;

p is 0, 1, 2, 3, or 4;

q is 0, 1, 2, 3, 4, or 5.

In some embodiments, the compounds of the invention are those represented by formula (V), wherein R$_8$ and R$_9$ are independently selected from the group consisting of H, C$_{1-4}$alkyl, and C$_{1-4}$heteroalkyl, wherein the said alkyl and heteroalkyl are optionally substituted with one or more substituents independently selected from the group consisting of OH, NH$_2$, CF$_3$, halogen, lower alkyl, and lower heteroalkyl; or R$_8$ and R$_9$ may join to form a bond.

In some embodiments, the compounds of the invention are those represented by formula (IV), wherein R$_8$ and R$_9$ are independently selected from the group consisting of H, C$_{1-4}$alkyl, and C$_{1-4}$heteroalkyl; or R$_8$ and R$_9$ may join to form a bond.

In some embodiments, the compounds of the invention are those represented by formula (V), wherein R$_8$ and R$_9$ are both H; or R$_8$ and R$_9$ may join to form a bond.

In some embodiments, the compounds of the invention are those represented by formula (V), wherein R$_{20}$ is independently selected from the group consisting of H, and lower alkyl;

In some embodiments, the compounds of the invention are those represented by formula (V), wherein R$_{21}$ is independently selected from the group consisting of H, NO$_2$, OMe, CF$_3$, halogen, C$_{1-4}$alkyl, and C$_{1-4}$heteroalkyl.

In some embodiments, the compounds of the invention are those represented by formula (V), wherein R$_7$ is selected from the group consisting of H, C$_{1-4}$alkyl, C$_{1-4}$heteroalkyl, and C$_{1-8}$alkylaminoalkyl, wherein the said alkyl and heteroalkyl are optionally substituted with one or more substituents independently selected from the group consisting of OH, NH$_2$, CF$_3$, halogen, lower alkyl, and lower heteroalkyl.

In some embodiments, the compounds of the invention are those represented by formula (V), wherein R$_7$ is selected from the group consisting of H, C$_{1-4}$alkyl, C$_{1-4}$heteroalkyl, and C$_{1-8}$alkylaminoalkyl.

In some embodiments, the compounds of the invention are those represented by formula (V), wherein R$_7$ is H.

In some embodiments, the compounds of the invention are those represented by formula (V), wherein Z is selected from the group consisting of C(=O), S(=O)$_2$, and S(=O).

In some embodiments, the compounds of the invention are those represented by formula (V), wherein Z is selected from the group consisting of C(=O) and S(=O)$_2$.

In some embodiments, the compounds of the invention are those represented by formula (V), wherein Y is selected from the group consisting of C$_{1-8}$alkyl, C$_{2-9}$heteroalkyl, aryl, heteroaryl, 4- to 7-membered cycloalkyl, and 4- to 7-membered heterocycloalkyl, wherein the said alkyl, heteroalkyl, aryl, heteroaryl, cycloalkyl, and heterocycloalkyl are optionally substituted with one or more substituents independently selected from the group consisting of OH, NH$_2$, CF$_3$, halogen, lower alkyl, and lower heteroalkyl.

In some embodiments, the compounds of the invention are those represented by formula (V), wherein Y is selected from the group consisting of C$_{1-8}$alkyl, C$_{2-9}$heteroalkyl, aryl, heteroaryl, 4- to 7-membered cycloalkyl, and 4- to 7-membered heterocycloalkyl.

In some embodiments, the compounds of the invention are those represented by formula (V), wherein Y is selected from the group consisting of C$_{1-8}$alkyl, 4- to 7-membered cycloalkyl and 4- to 7-membered heterocycloalkyl.

In some embodiments, the compounds of the invention are those represented by formula (V), wherein Y is selected from the group consisting of

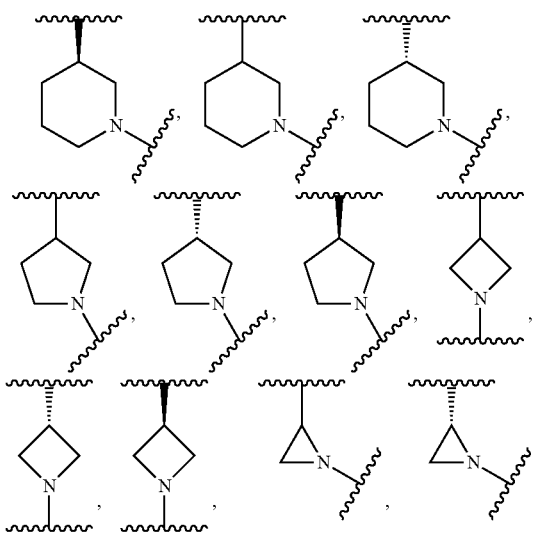

-continued

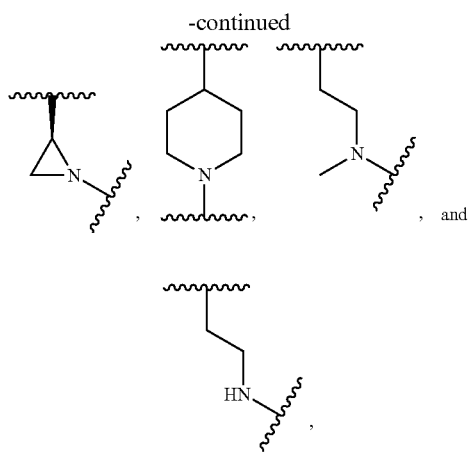

wherein the said

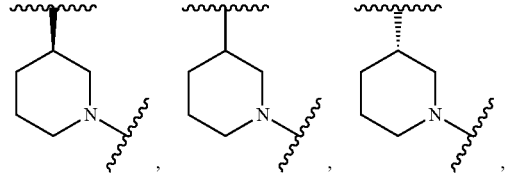

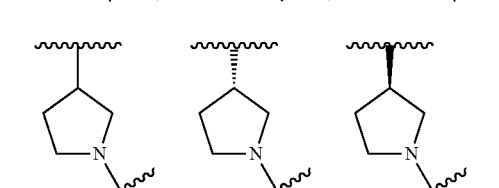

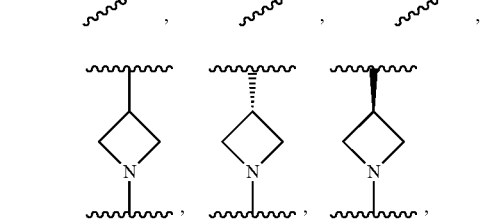

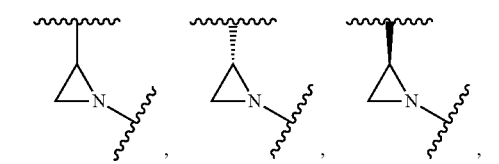

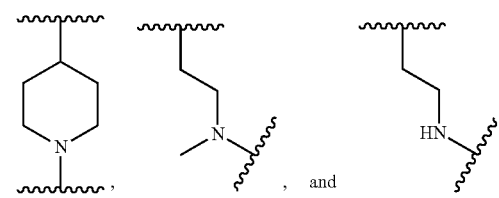

groups are optionally substituted with one or more substituents independently selected from the group consisting of OH, NH$_2$, CF$_3$, halogen, lower alkyl, and lower heteroalkyl.

In some embodiments, the compounds of the invention are those represented by formula (V), wherein Y is selected from the group consisting of

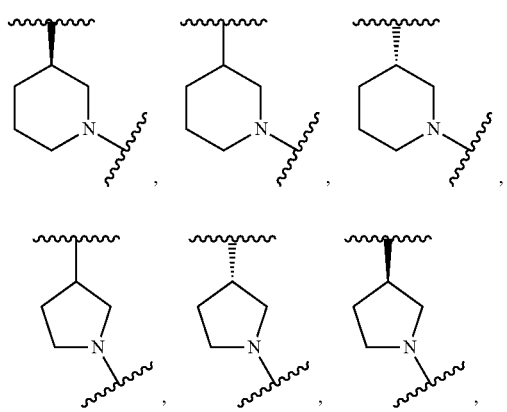

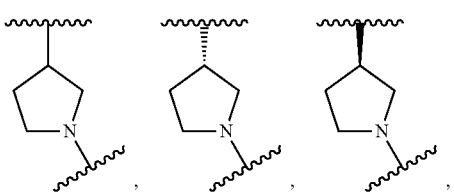

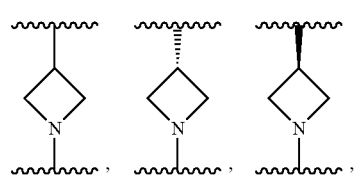

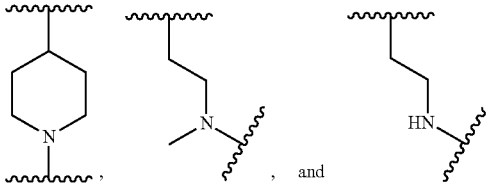

, and

In some embodiments, the compounds of the invention are those represented by formula (V), wherein Y is selected from the group consisting of

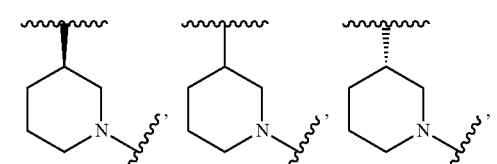

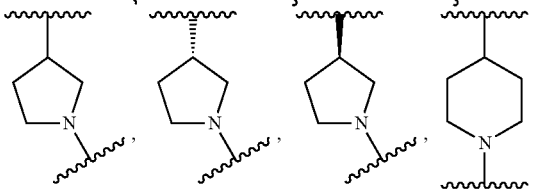

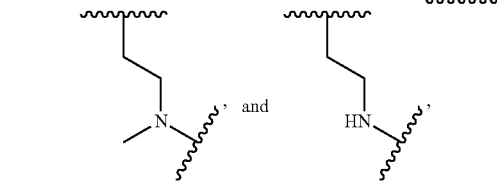

wherein the said

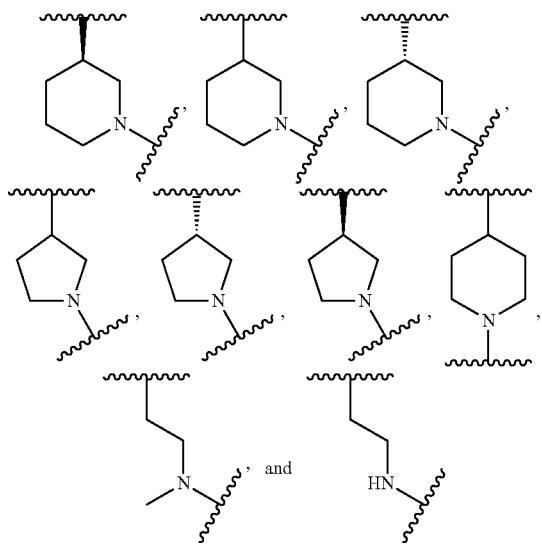

groups are optionally substituted with one or more substituents independently selected from the group consisting of OH, NH$_2$, CF$_3$, halogen, lower alkyl, and lower heteroalkyl.

In some embodiments, the compounds of the invention are those represented by formula (V), wherein Y is selected from the group consisting of

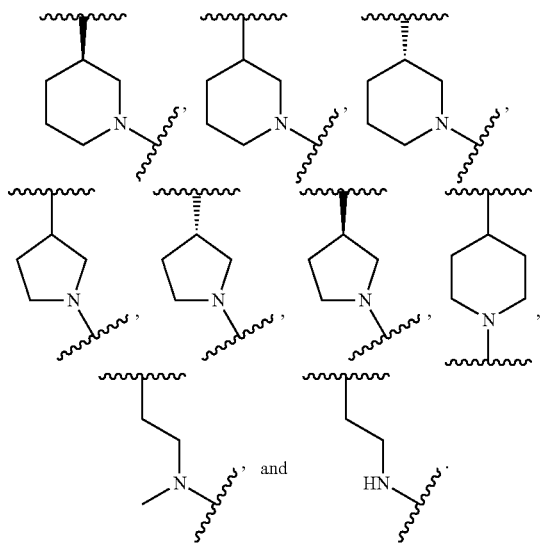

In some embodiments, the compounds of the invention are those represented by formula (V), wherein X$_1$ is C, X$_2$ and X$_3$ are N; or X$_1$ is N, X$_2$ is CH, and X$_3$ is C; or X$_1$ is C, X$_2$ is CH, and X$_3$ is N.

In some embodiments, the compounds of the invention are those represented by formula (V), wherein X$_1$ is C, X$_2$ and X$_3$ are N.

In some embodiments, the compounds of the invention are those represented by formula (V), wherein L$_a$ is selected from the group consisting of O, S and NH.

In some embodiments, the compounds of the invention are those represented by formula (V), wherein L$_a$ is O.

In some embodiments, the compounds of the invention are those represented by formula (V), wherein X$_0$ is selected from the group consisting of O, S and NH.

In some embodiments, the compounds of the invention are those represented by formula (V), wherein X$_0$ is O.

In some embodiments, the compounds of the invention are those represented by formula (V), wherein R$_2$ and R$_3$ are independently selected from the group consisting of H and C$_{1-4}$alkyl; or R$_2$ and R$_3$ join to form a 3- to 8-membered heterocyclic ring.

In some embodiments, the compounds of the invention are those represented by formula (V), wherein R$_2$ and R$_3$ are H; or R$_2$ is H, and R$_3$ is C$_{1-4}$alkyl; or R$_3$ is H, and R$_2$ is C$_{1-4}$alkyl.

In some embodiments, the compounds of the invention are those represented by formula (V), wherein R$_6$ is selected from the group consisting of H, —C$_{1-8}$alkyl, —(CH$_2$)$_n$C$_{3-7}$cycloalkyl, —(CH$_2$)$_n$C$_{2-9}$heterocycloalkyl, —(CH$_2$)$_n$—OH, —(CH$_2$)$_n$(CHOH)$_n$—H, —(CH$_2$)$_n$—O—(CH$_2$)$_n$CH$_3$, —(CH$_2$)$_n$—S—(CH$_2$)$_n$CH$_3$, —(CH$_2$)$_n$—NH$_2$, —(CH$_2$)$_n$—NH(C$_{1-8}$alkyl), —(CH$_2$)$_n$—N(C$_{1-8}$ alkyl)$_2$, —C(O)CF$_3$, —C(O)C$_{1-8}$alkyl, —(CH$_2$)$_n$-phenyl, and —(CH$_2$)$_n$-heteroaryl.

In some embodiments, the compounds of the invention are those represented by formula (V), wherein R$_6$ is selected from the group consisting of H, —C$_{1-8}$alkyl, —(CH$_2$)$_n$C$_{3-7}$cycloalkyl, —(CH$_2$)$_n$C$_{2-9}$heterocycloalkyl, —(CH$_2$)$_n$—OH, —(CH$_2$)$_n$(CHOH)$_n$—H, —(CH$_2$)$_n$—O—(CH$_2$)$_n$CH$_3$, —(CH$_2$)$_n$—S—(CH$_2$)$_n$CH$_3$, —(CH$_2$)$_n$—NH$_2$, —(CH$_2$)$_n$—NH(C$_{1-8}$alkyl), —(CH$_2$)$_n$—N(C$_{1-8}$alkyl)$_2$, and —C(O)C$_{1-8}$alkyl.

In some embodiments, the compounds of the invention are those represented by formula (V), wherein R$_6$ is selected from the group consisting of H, Me, Et,

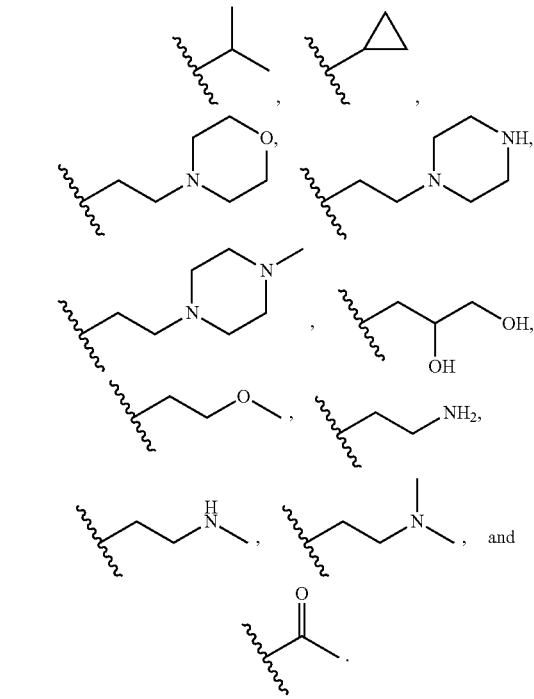

In some embodiments, the compounds of the invention are those represented by formula (V), wherein n=0, 1, 2, 3, 4, 5, or 6.

In some embodiments, the compounds of the invention are those represented by formula (V), wherein n=0, 1, 2, 3, or 4.

In some embodiments, the compounds of the invention are those represented by formula (V), wherein p=0, 1, or 2.
In some embodiments, the compounds of the invention are those represented by formula (V), wherein q=0, 1, 2, or 3.
In some embodiments, the compounds of the present invention are those represented by any of the following formula
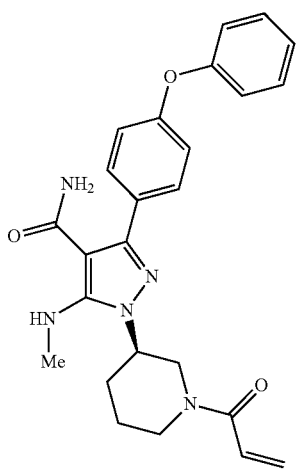
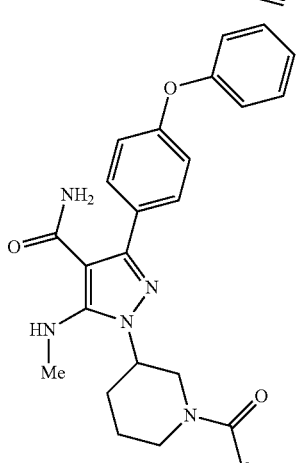
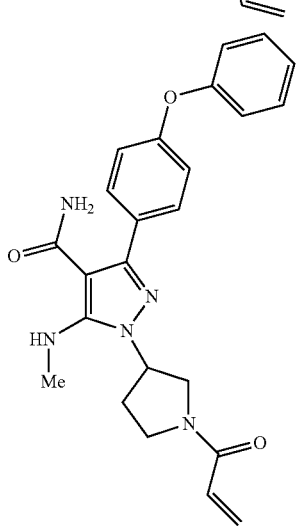
-continued
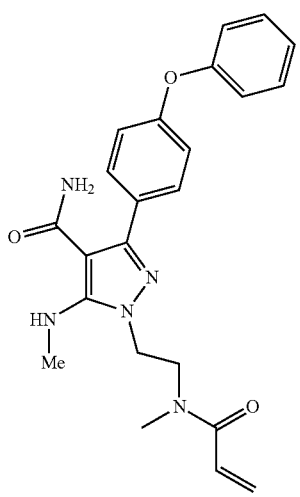
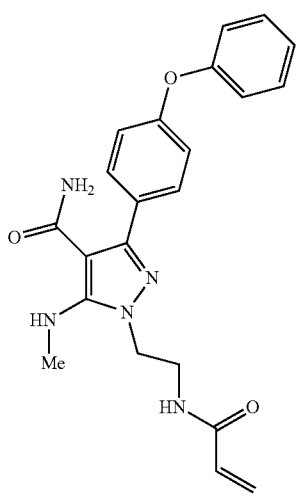
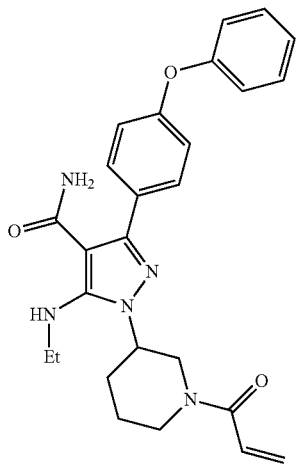

29
-continued
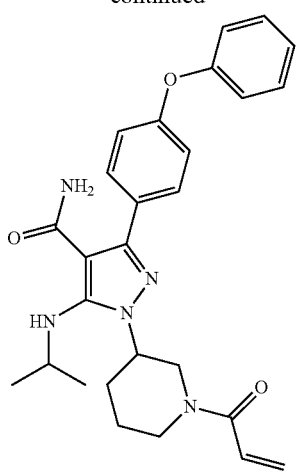
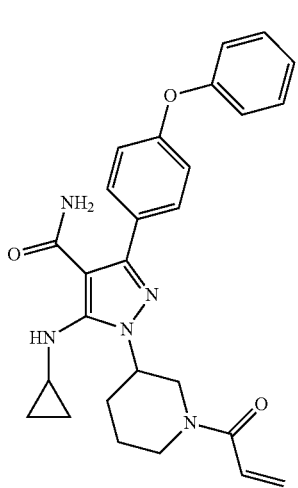
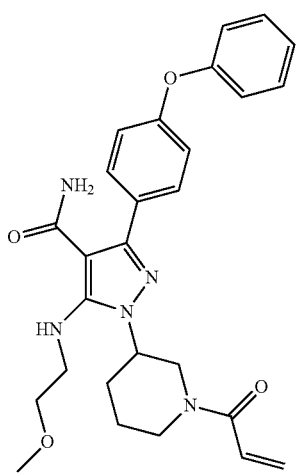
30
-continued
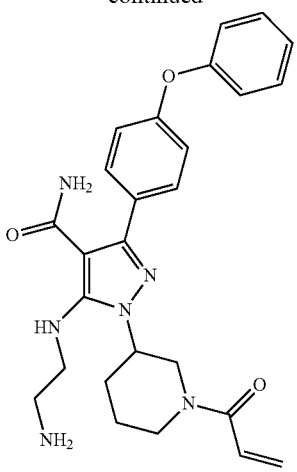
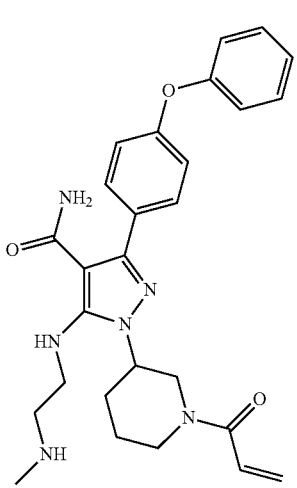
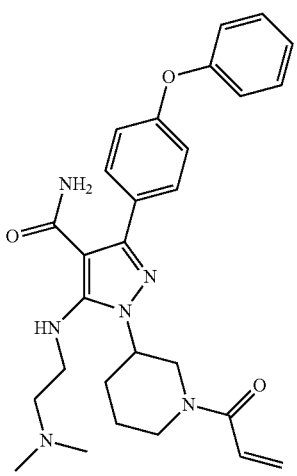

31
-continued
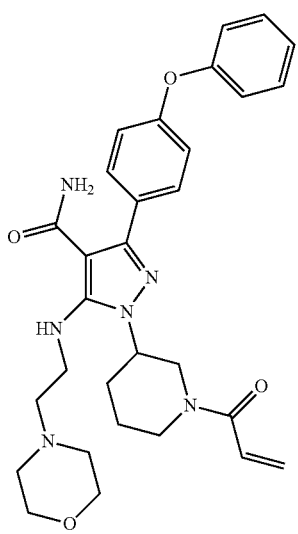
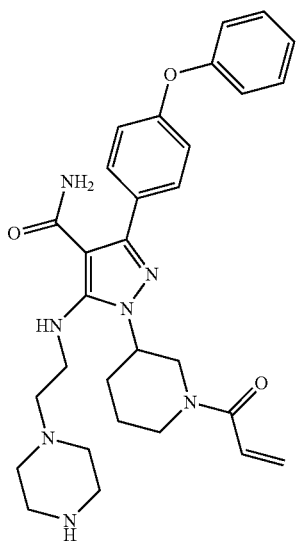
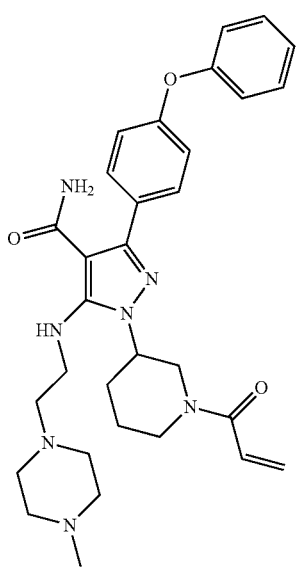
32
-continued
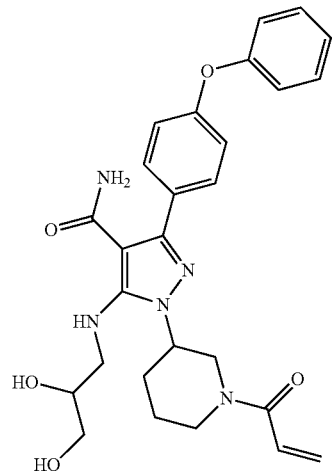
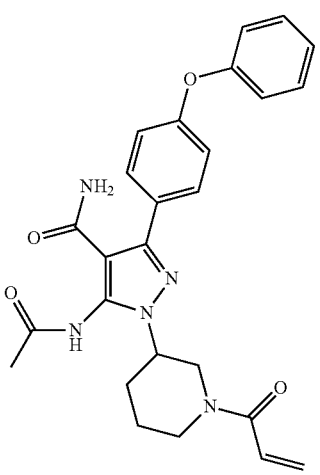
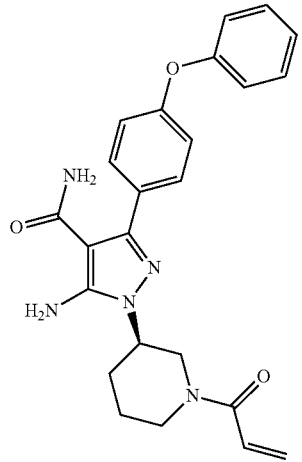

33
34
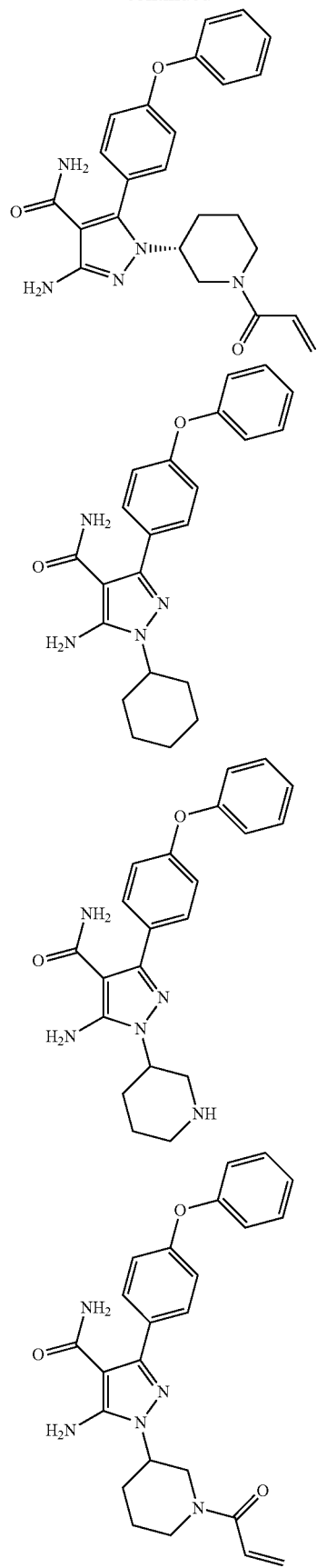
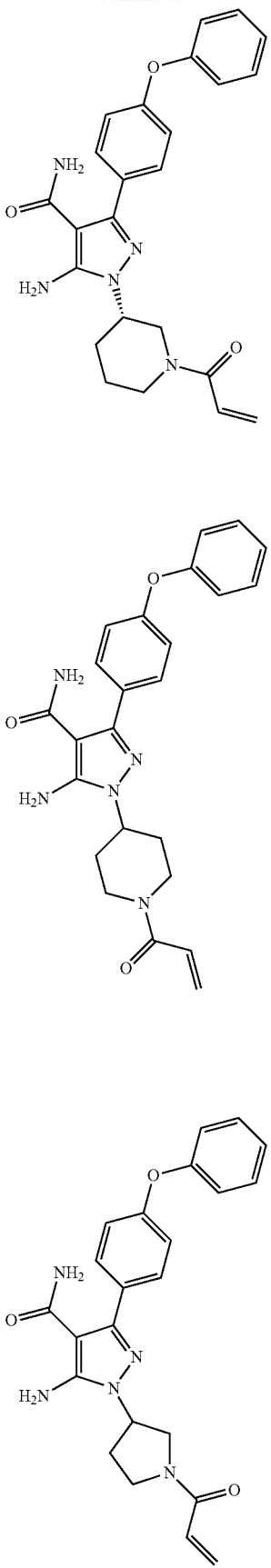

35
-continued
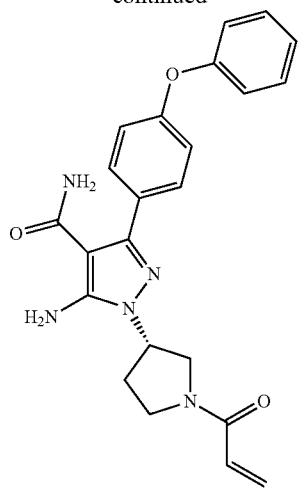
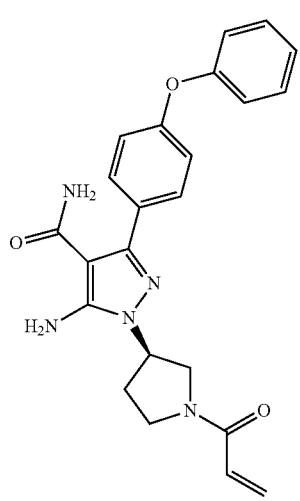
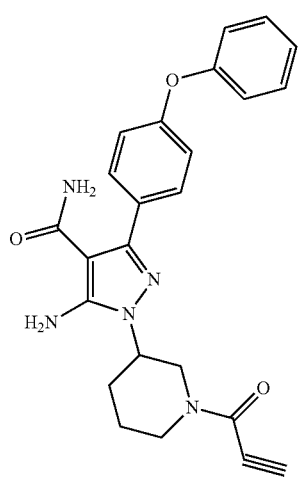
36
-continued
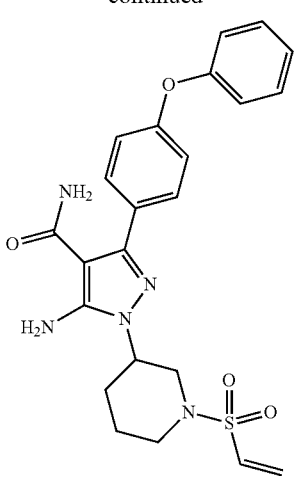
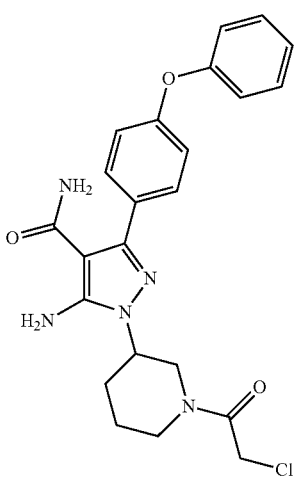
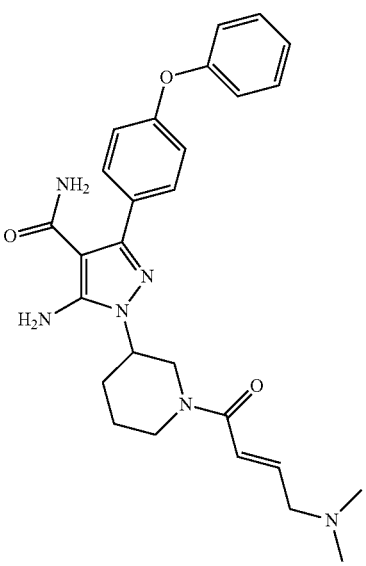

37
-continued
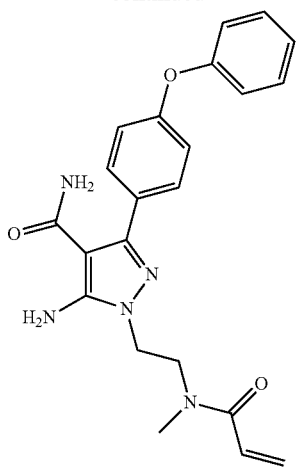
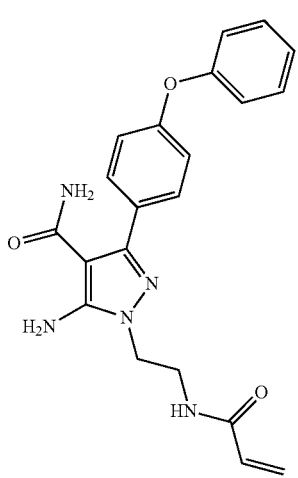
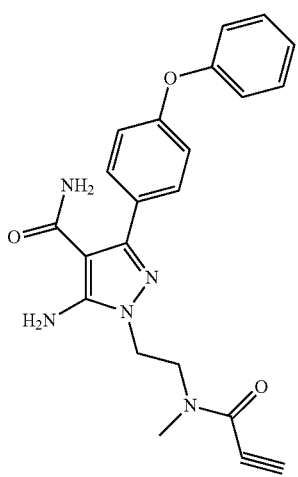
38
-continued
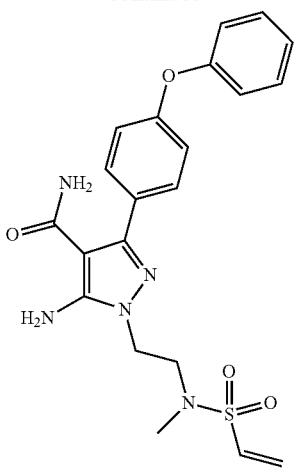
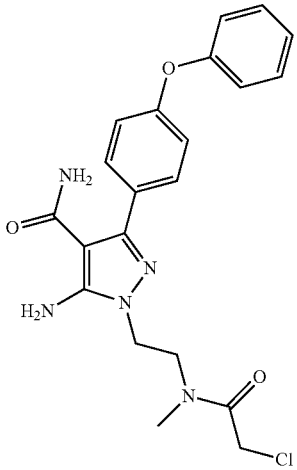
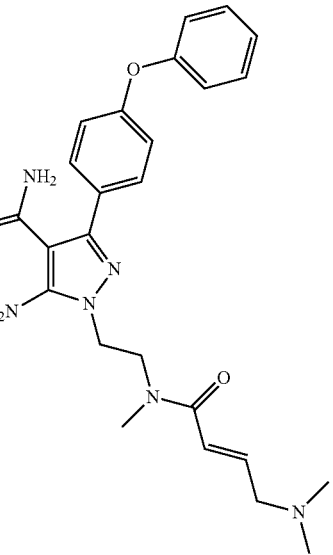

39
-continued
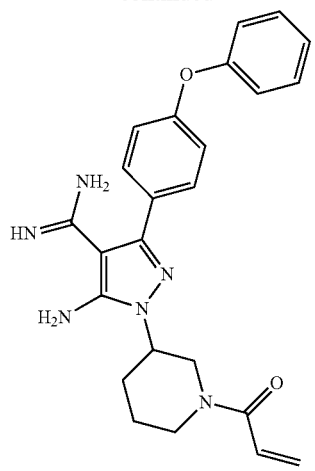
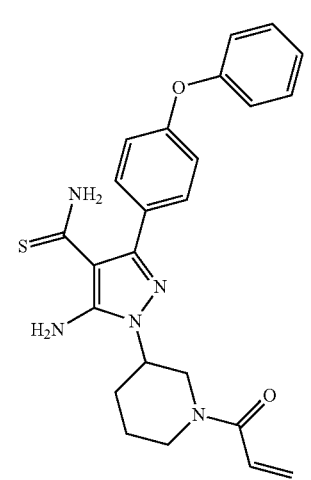
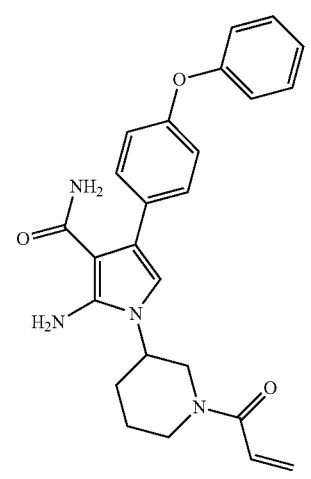
40
-continued
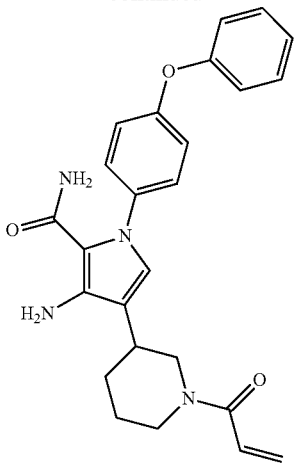
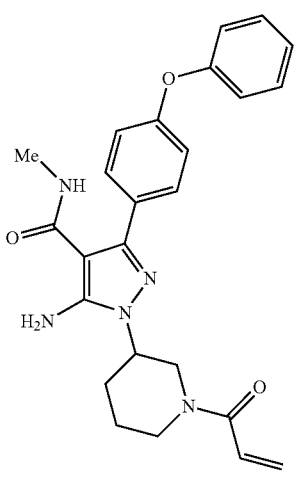
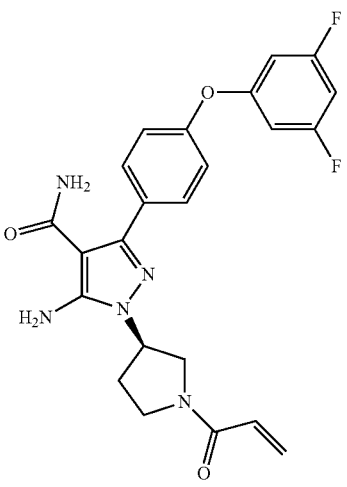

41
-continued
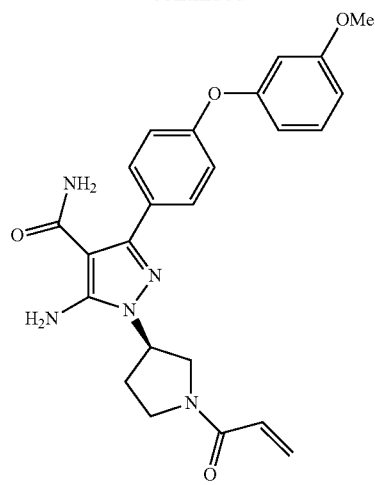
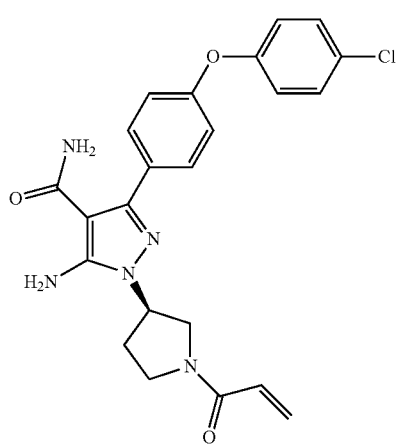
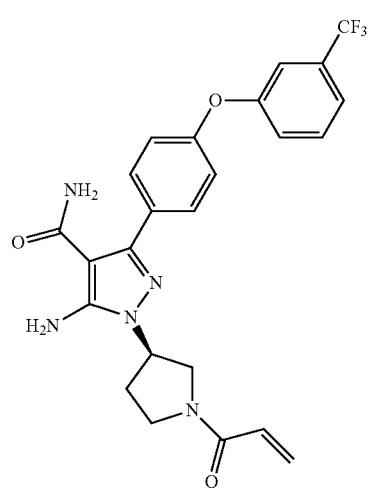
42
-continued
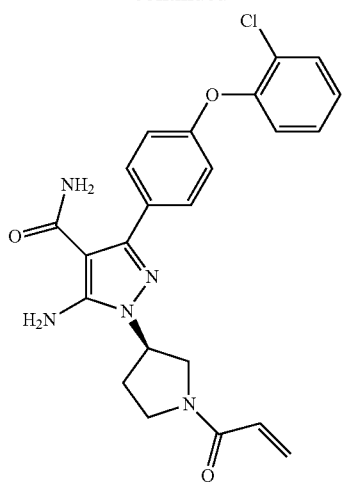
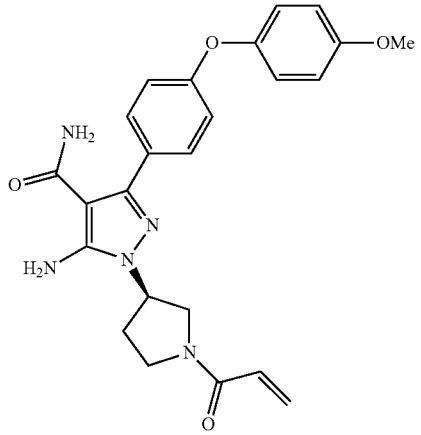
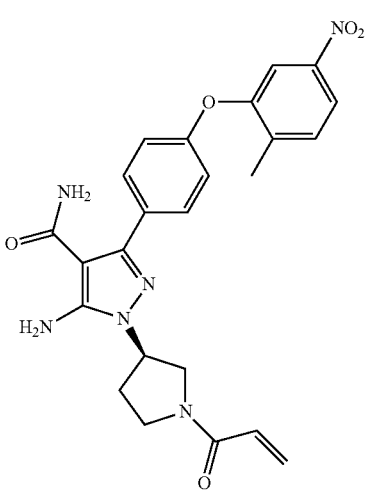

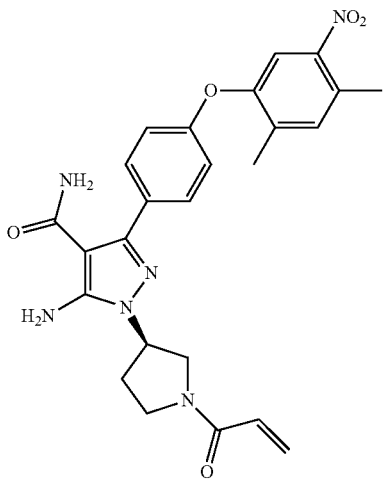

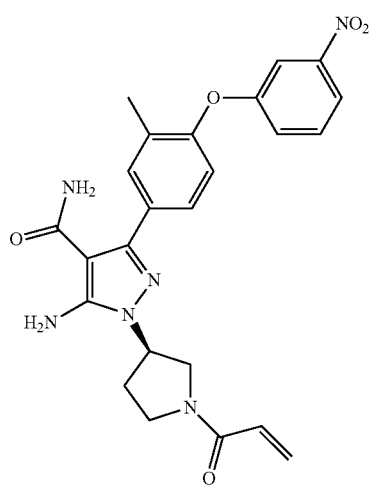

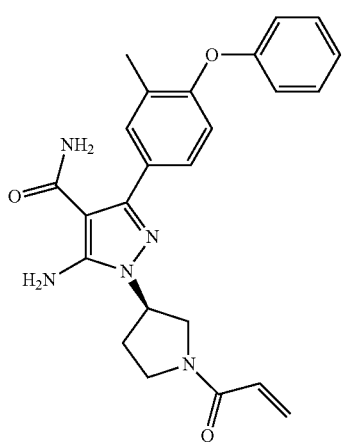

In another aspect, the invention provides use of a compound, or a therapeutically acceptable salt, solvate, metabolite, polymorph, ester, tautomer, or prodrug thereof, as a medicament.

In another aspect, the invention provides a pharmaceutical composition comprising at least one compound of the invention, or a therapeutically acceptable salt, solvate, metabolite, polymorph, ester, tautomer, or prodrug thereof, and a pharmaceutically acceptable carrier.

In another aspect, the invention provides a method for preventing or treating a subject suffering from or at risk of autoimmune disease, inflammatory disease, asthma, arthritis, rheumatoid arthritis, systemic Lupus Erythematosus (SLE), or cancer such as B-cell histiocytosis, comprising: administering to mammals (especially human beings) an effective amount of a compound of the invention, or a therapeutically acceptable salt, solvate, metabolite, polymorph, ester, tautomer, or prodrug thereof.

In another aspect, the invention provides a method for preventing or treating a subject suffering from or at risk of chronic lymphocytic lymphoma, diffuse large B cell lymphoma (DLBCL), follicular lymphoma, or chronic lymphoblastic leukaemia, comprising: administering to mammals (especially human beings) an effective amount of a compound of the invention, or a therapeutically acceptable salt, solvate, metabolite, polymorph, ester, tautomer, or prodrug thereof.

In another aspect, the invention provides a method for treating an autoimmune disease related to abnormal elevation of BTK kinase activity of a mammal (especially a human being), comprising: administering to said subject an effective amount of a compound according to any compound of the invention, or a therapeutically acceptable salt, solvate, metabolite, polymorph, ester, tautomer, or prodrug thereof.

In another aspect, the invention provides use of a compound of the invention, or a therapeutically acceptable salt, solvate, metabolite, polymorph, ester, tautomer, or prodrug thereof, in the preparation of a medicament for preventing or treating a subject suffering from or at risk of autoimmune disease, inflammatory disease, asthma, arthritis, rheumatoid arthritis, systemic Lupus Erythematosus (SLE), or cancer such as B-cell histiocytosis.

In another aspect, the invention provides use of a compound of the invention, or a therapeutically acceptable salt, solvate, metabolite, polymorph, ester, tautomer, or prodrug thereof, in the preparation of a medicament for preventing or treating a subject suffering from or at risk of chronic lymphocytic lymphoma, diffuse large B cell lymphoma (DLBCL), follicular lymphoma, or chronic lymphoblastic leukaemia.

In another aspect, the invention provides use of a compound of the invention, or a therapeutically acceptable salt, solvate, metabolite, polymorph, ester, tautomer, or prodrug thereof, in the preparation of a medicament for preventing or treating a mammal (especially a human being) suffering from diseases related to abnormal elevation of BTK kinase activity.

In another aspect, the invention provides a method to inhibit the BTK kinase activity, comprising: reaction of the BTK kinase with a compound of the invention, or a therapeutically acceptable salt, solvate, metabolite, polymorph, ester, tautomer, or prodrug thereof, either in vitro or in vivo.

In another aspect, the inhibited tyrosine kinase, comprising a Bruton's tyrosine kinase, a Bruton's tyrosine kinase hamolog, or a Btk tyrosine kinase cysteine homolog, bound to an inhibitor having the structure:

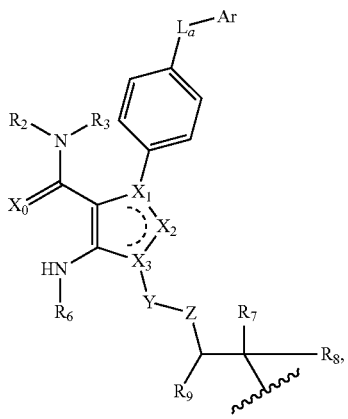

wherein, ~~~~~ indicates the point of attachment between the inhibitor of the tyrosine kinase. In another aspect, the inhibitor is covalently bound to a cysteine residue on the tyrosine kinase.

In one aspect, the invention provides a compound of Formula (I),

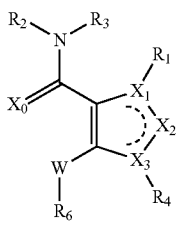

Formula (I)

or a therapeutically acceptable salt, solvate, ester, acid, or prodrug thereof, wherein:

$X_0$ is selected from the group consisting of O, $CH_2$, NH and S;

$X_1$ and $X_3$ are independently selected from the group consisting of C and N;

$X_2$ is selected from the group consisting of $CR_5$, N, and $NR_5$;

$R_1$ is selected from the group consisting of H, $L_2$-(optionally substituted alkyl), $L_2$-(optionally substituted cycloalkyl), $L_2$-(optionally substituted alkenyl), $L_2$-(optionally substituted cycloalkenyl), $L_2$-(optionally substituted heterocycle), $L_2$-(optionally substituted aryl), and $L_2$-(optionally substituted heteroaryl), wherein $L_2$ is selected from the group consisting of a bond, O, S, —S(=O)—, —S(=O)$_2$—, —C(=O)—, -(optionally substituted $C_{1-6}$alkyl)-, and -(optionally substituted $C_{2-6}$alkenyl)-;

$R_2$ and $R_3$ are independently selected from the group consisting of H and optionally substituted lower alkyl; or $R_2$ and $R_3$, together with the nitrogen atom to which they are attached, form a 3 to 8-membered heterocyclic ring;

$R_4$ is $L_3$-X-$L_4$-G, wherein, $L_3$ is selected from the group consisting of a bond, optionally substituted alkylene, optionally substituted cycloalkylene, optionally substituted alkenylene, and optionally substituted alkynylene;

X is selected from the group consisting of a bond, O, —C(=O)—, S, —S(=O)—, —S(=O)$_2$—, —$NR_{10}$—, —NHC(O)—, —$NR_{10}$C(O)—, —C(O)$NR_{10}$—, —NHS(=O)$_2$—, —S(=O)$_2NR_{10}$—, —$NR_{10}$S(=O)$_2$—, —NHC(O)O—, —OC(O)$NR_{10}$—, —$NR_{10}$C(O)O—, —CH=NO—, —ON=CH—, —$NR_{11}$C(O)$NR_{11}$—, heteroarylene, arylene, —$NR_{11}$C(=$NR_{12}$)$NR_{11}$—, —$NR_{11}$C(=$NR_{12}$)—, —C(=$NR_{12}$)$NR_{11}$—, —OC(=$NR_{12}$)—, and —C(=$NR_{12}$)O—; wherein, $R_{10}$ and $R_{11}$ are independently selected from the group consisting of H, optionally substituted lower alkyl and optionally substituted lower cycloalkyl; or $R_{10}$ and $R_{11}$ may join to form a 5 to 8-membered heterocyclic ring;

$R_{12}$ is independently selected from the group consisting of H, —S(=O)$_2R_9$, —S(=O)$_2NH_2$, —C(O)$R_9$, —CN, —$NO_2$, heteroaryl, and heteroalkyl; or two $R_{12}$ groups may join to form a 5 to 8-membered heterocyclic ring;

$L_4$ is selected from the group consisting of a bond, optionally substituted alkylene, optionally substituted cycloalkylene, optionally substituted heterocycloalkylene-, optionally substituted alkenylene, optionally substituted alkynylene, optionally substituted arylene, and optionally substituted heteroarylene; or $L_3$, X and $L_4$ join to form a nitrogen containing heterocyclic ring;

G is selected from the group consisting of H,

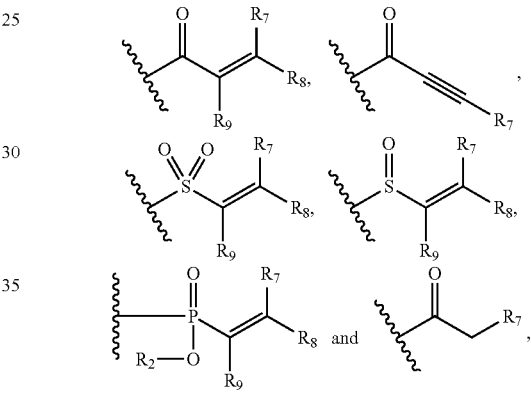

wherein, $R_7$, $R_8$ and $R_9$ are independently selected from the group consisting of H, halogen, optionally substituted lower alkyl, optionally substituted lower heteroalkyl, optionally substituted lower cycloalkyl, and optionally substituted lower heterocycloalkyl;

$R_5$ is selected from the group consisting of H, halogen, -$L_6$-(optionally substituted $C_{1-3}$alkyl), -$L_6$-(optionally substituted $C_{2-4}$alkenyl), -$L_6$-(optionally substituted aryl) and -$L_6$-(optionally substituted heteroaryl), wherein $L_6$ is selected from the group consisting of a bond, O, S, —S(=O)—, —S(=O)$_2$—, NH, —C(=O)—, —NHC(O)O—, —OC(O)NH—, —NHC(O)—, and —C(O)NH—; or $R_5$ is the same as $R_4$.

W is selected from the group consisting of a bond, —O—, —NH—, —S—, —(CH$_2$)$_m$—, —(CH$_2$)$_mC_{2-6}$heterocycloalkyl-, —(CH$_2$)$_nC_{2-6}$heterocycloalkyl-(CH$_2$)$_n$—$NR_{13}$—, —$NR_{13}$—(CH$_2$)$_n$—$C_{3-6}$cycloalkyl-(CH$_2$)$_n$—$NR_{13}$—, —(CH$_2$)$_mNR_{13}$—, —$NR_{13}$—(CH$_2$)$_m$—, —(CH$_2$)$_n$—$NR_{13}$—(CH$_2$)$_n$—$NR_{13}$—, —$NR_{13}$—$C_{2-6}$alkenyl-, —$NR_{13}$—$C_{2-6}$alkynyl-, —$NR_{13}$-phenyl-, —$NR_{13}$-phenyl-$NR_{13}$—, —$NR_{13}$—(CH$_2$)$_n$-heteroaryl-, —$NR_{13}$—(CH$_2$)$_n$—$C_{2-6}$heterocycloalkyl-, and —$NR_{13}$-heteroaryl-$NR_{13}$—; wherein the said alkenyl, alkynyl, cycloalkyl, heterocycloalkyl, phenyl, heteroaryl, and (CH$_2$) groups are optionally substituted with one or more substituents selected from —OH, halogen, —OCH$_3$ and $C_{1-8}$alkyl;

$R_6$ is selected from the group consisting of H, halogen, —$NH_2$, —$C_{1-8}$alkyl, —$C_{2-8}$alkenyl, —$C_{2-8}$alkynyl, —$(CH_2)_nC_{3-7}$cycloalkyl, —$(CH_2)_nC_{2-9}$heterocycloalkyl, —$(CH_2)_n$-phenyl, —$(CH_2)_n$-naphthyl, —$(CH_2)_n$-heteroaryl, —$(CH_2)_nCO_2H$, —$(CH_2)_n$—$(CHOH)_n$—$CH_2OH$, —$SR_{13}$, —$OR_{13}$, —$COR_{13}$, —$CH_2$—$N(R_{13})_2$, —$(CH_2)_n$—$N(R_{13})_2$, —$(CH_2)_n$—$N(R_{13})CO_2C_{1-8}$alkyl, —$C(O)(CH_2)_n$-aryl, —$C(O)C_{1-8}$alkyl, —$C(O)C_{3-7}$cycloalkyl, —$C(O)C_{2-9}$heterocycloalkyl, —$C(O)(CH_2)_n$-heteroaryl, —$C(O)CF_3$, —$C(O)(CH_2)_n$—$N(R_{13})_2$, —$C(O)N(R_{13})C_{1-8}$alkyl, —$CO_2(CH_2)_nC_{3-7}$cycloalkyl, —$C(O)N(R_{13})(CH_2)_nC_{3-7}$cycloalkyl, —$C(O)N(R_{13})(CH_2)_nC_{2-7}$heterocycloalkyl, —$CO_2(CH_2)_n$-heteroaryl, —$CO_2(CH_2)_n$-phenyl, —$C(O)N(R_{13})(CH_2)_n$-phenyl, —$CO_2(CH_2)_n$-naphthyl, —$C(O)N(R_{13})(CH_2)_n$-naphthyl, —$C(O)N(R_{13})(CH_2)_n$-heteroaryl, —$CO_2C_{1-8}$alkyl, —$SO_2C_{1-8}$alkyl, —$C(S)N(R_{13})(CH_2)_n$-phenyl, —$CO_2(CH_2)_nC_{2-9}$heterocycloalkyl, —$SO_2C_{3-7}$cycloalkyl, —$SO_2C_{2-9}$heterocycloalkyl, —$SO_2$-phenyl, —$SO_2$-naphthyl, —$SO_2$-heteroaryl, —$S(O)N(R_{13})$-phenyl, —S—$C_{1-8}$alkyl, —S—$C_{3-7}$ cycloalkyl, —S—$C_{2-9}$heterocycloalkyl, —S-phenyl, —S-naphthyl and —S-heteroaryl; wherein the said alkyl, alkenyl, alkynyl, cycloalkyl, heterocycloalkyl, aryl, phenyl, naphthyl, heteroaryl, and (CH2) groups are optionally substituted with one or more substituents independently selected from $R_{14}$;

R6 and L4 may join to form a 3- to 12-membered ring;

R13 is selected from the group consisting of H, —C1-8alkyl, —C2-8alkenyl, —C2-8alkynyl, —(CH2)n-phenyl, —C2-8alkenyl-phenyl and —(CH2)nCO2H; wherein the said alkyl, alkenyl, alkynyl, phenyl and ($CH_2$) groups are optionally substituted with one or more substituents independently selected from the group consisting of —$OC_{1-4}$alkyl and —$C_{1-4}$alkyl;

$R_{14}$ is selected from the group consisting of H, oxo, =NH, —CN, —$CF_3$, —$OCF_3$, —$C_{1-6}$ alkyl, —$C_{2-6}$alkenyl, —$C_{2-6}$alkynyl, —$(CH_2)_nC_{3-6}$cycloalkyl, —$(CH_2)_nC_{2-9}$heterocycloalkyl, —$(CH_2)_nOR_{13}$, —$(CH_2)_nCO_2R_{13}$, —$(CH_2)_nCO_2(CH_2)_n$-phenyl, —$(CH_2)_n$-phenyl, —$(CH_2)_n$—O-phenyl, —$(CH_2)_n$-naphthyl, —$(CH_2)_n$-heteroaryl, —$N(R_{13})_2$, —$NR_{13}C(O)R_{13}$, —$NR_{13}CO_2R_{13}$, —$C(O)$phenyl, —$C(O)$heteroaryl, —$SR_{13}$, —$SO_2C_{1-6}$alkyl and —$SO_2N(R_{13})_2$; wherein the said alkyl, alkenyl, alkynyl, phenyl, heteroaryl, heterocycloalkyl, naphthyl, cycloalkyl and ($CH_2$) groups are optionally substituted with one or more substituents independently selected from the group consisting of —OH, halogen, —$OCH_3$ and $C_{1-4}$alkyl;

n is 0, 1, 2, 3, 4, 5, 6, 7, or 8;

m is 1, 2, 3, 4, 5, 6, 7, or 8.

Another embodiment of this invention provides a compound of Formula (II)

Formula (II)

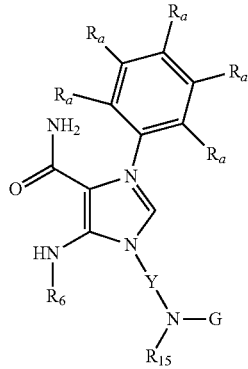

or a therapeutically acceptable salt, solvate, ester, acid, or prodrug thereof, wherein:

Y is selected from the group consisting of optionally substituted alkylene and 4-, 5-, and 6-membered cycloalkyl ring;

$R_a$ is independently selected from the group consisting of H, halogen, —$CF_3$, —CN, —$NO_2$, —OH, —$NH_2$, -$L_a$-(optionally substituted alkyl), -$L_a$-(optionally substituted alkenyl), -$L_a$-(optionally substituted aryl), -$L_a$-(optionally substituted heteroaryl), wherein $L_a$ is selected from the group consisting of a bond, O, S, S(=O), S(=O)$_2$, NH, C(=O), $CH_2$, NHC(O)O, NHC(O) and C(O)NH;

G is selected from the group consisting of H,

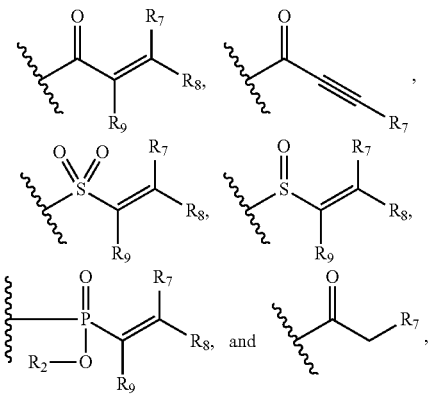

wherein $R_7$, $R_8$ and $R_9$ are independently selected from the group consisting of H, halogen, optionally substituted lower alkyl, optionally substituted lower heteroalkyl, optionally substituted lower cycloalkyl, and optionally substituted lower heterocycloalkyl;

$R_{15}$ is selected from the group consisting of H and lower alkyl;

Y and $R_{15}$ may join to form a 4-, 5-, or 6-membered heterocyclic ring;

$R_6$ is selected from the group consisting of H, halogen, amino, —$C_{1-8}$alkyl, —$C_{2-8}$ alkenyl, —$C_{2-8}$alkynyl, —$(CH_2)_nC_{3-7}$ cycloalkyl, —$(CH_2)_nC_{2-9}$ heterocycloalkyl, —$(CH_2)_n$-phenyl, —$(CH_2)_n$-naphthyl, —$(CH_2)_n$-heteroaryl, —$(CH_2)_nCO_2H$, —$(CH_2)_n$—$(CHOH)_n$—$CH_2OH$, —$COR_{13}$, —$(CH_2)_n$—$N(R_{13})_2$, —$(CH_2)_n$—$N(R_{13})CO_2C_{1-8}$alkyl, —$C(O)(CH_2)_n$-aryl, —$C(O)C_{1-8}$alkyl, —$C(O)C_{3-7}$cycloalkyl, —$C(O)C_{2-9}$heterocycloalkyl, —$C(O)(CH_2)$-heteroaryl, —$C(O)CF_3$, —$C(O)(CH_2)$—$N(R_{13})_2$, —$C(O)N(R_{13})C_{1-8}$alkyl, —$CO_2$ $(CH_2)_nC_{3-7}$ cycloalkyl, —$C(O)N(R_{13})(CH_2)_nC_{3-7}$ cycloalkyl, —$C(O)N(R_{13})(CH_2)_nC_{2-7}$heterocycloalkyl, —$CO_2$ $(CH_2)_n$-heteroaryl, —$CO_2$ $(CH_2)_n$-phenyl, —$C(O)N(R_{13})(CH_2)_n$-phenyl, —$CO_2(CH_2)$-naphthyl, —$C(O)N(R_{13})(CH_2)_n$-naphthyl, —$C(O)N(R_{13})(CH_2)_n$-heteroaryl, —$CO_2C_{1-8}$alkyl, —$SO_2C_{1-8}$ alkyl, —$C(S)N(R_{13})(CH_2)_n$-phenyl, —$CO_2$ $(CH_2)_nC_{2-9}$heterocycloalkyl, —$SO_2C_{3-7}$cycloalkyl, —$SO_2C_{2-9}$ heterocycloalkyl, —$SO_2$phenyl, —$SO_2$naphthyl, —$SO_2$heteroaryl, and —$S(O)N(R_{13})$phenyl; wherein the said alkyl, alkenyl, alkynyl, cycloalkyl, heterocycloalkyl, aryl, phenyl, naphthyl, heteroaryl, and ($CH_2$) groups are optionally substituted with one or more substituents independently selected from $R_{14}$;

$R_6$ and $R_{15}$ may join to form a 3- to 12-membered ring;

$R_{13}$ is selected from the group consisting of H, —$C_{1-8}$alkyl, —$C_{2-8}$alkenyl, —$C_{2-8}$alkynyl, —$(CH_2)$-phenyl, —C$_{2-8}$alkenyl-phenyl and —(CH$_2$)$_n$CO$_2$H; wherein the said alkyl, alkenyl, alkynyl, phenyl, and (CH$_2$) groups are optionally substituted with one ore more substituents independently selected from —OC$_{1-4}$alkyl and —C$_{1-4}$alkyl;

R$_{14}$ is selected from the group consisting of H, oxo, =NH, —CN, —CF$_3$, —OCF$_3$, —C$_{1-6}$ alkyl, —C$_{2-6}$alkenyl, —C$_{2-6}$alkynyl, —(CH$_2$)$_n$C$_{3-6}$ cycloalkyl, —(CH$_2$)$_n$C$_{2-9}$heterocycloalkyl, —(CH$_2$)$_n$OR$_{13}$, —(CH$_2$)$_n$CO$_2$R$_{13}$, —(CH$_2$)$_n$CO$_2$(CH$_2$)$_n$-phenyl, —(CH$_2$)$_n$-phenyl, —(CH$_2$)—O-phenyl, —(CH$_2$)$_n$-naphthyl, —(CH$_2$)$_n$-heteroaryl, —N(R$_{13}$)$_2$, —NR$_3$C(O)R$_{13}$, —NR$_{13}$CO$_2$R$_{13}$, —C(O)phenyl, —C(O)heteroaryl, —SR$_{13}$, —SO$_2$C$_{1-6}$alkyl and —SO$_2$N(R$_{13}$)$_2$; wherein the said alkyl, alkenyl, alkynyl, phenyl, heteroaryl, heterocycloalkyl, naphthyl, cycloalkyl and (CH$_2$) groups are optionally substituted with one or more substituents independently selected from the group consisting of —OH, halogen, —OCH$_3$ and C$_{1-4}$alkyl;

n is 0, 1, 2, 3, 4, 5, 6, 7, or 8;

m is 1, 2, 3, 4, 5, 6, 7, or 8.

In some embodiments, the compounds of the invention are those represented by formula (II), wherein G is selected from the group consisting of

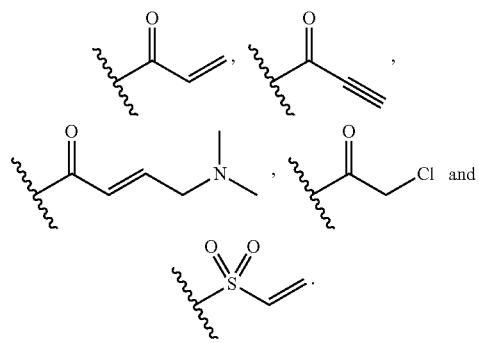

In some embodiments, the compounds of the invention are those represented by formula (II), wherein

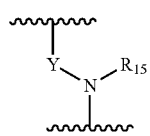

is selected from the group consisting of

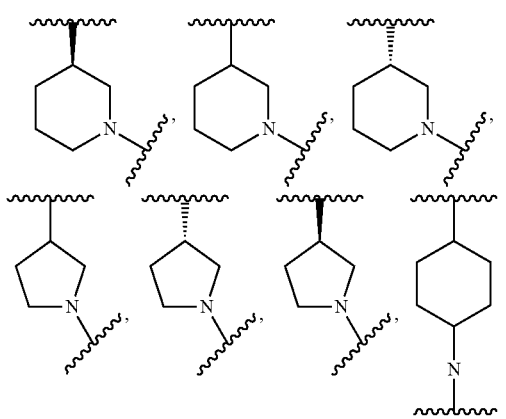

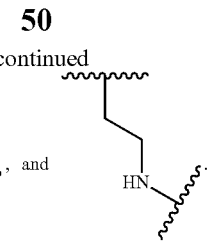

Another embodiment of this invention provides a compound of Formula (III),

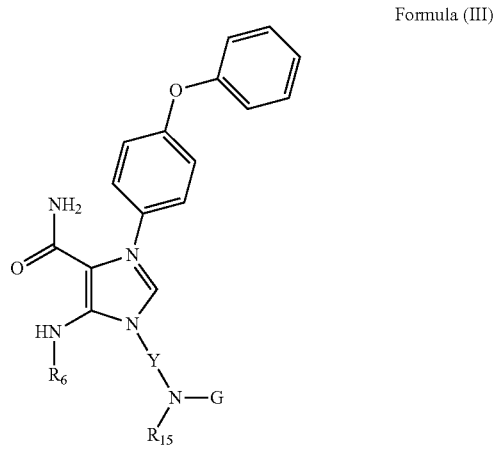

Formula (III)

or a therapeutically acceptable salt, solvate, ester, acid, or prodrug thereof, wherein:

Y is selected from the group consisting of a bond, optionally substituted alkyl and a 4-, 5-, or 6-membered cycloalkyl ring;

In some embodiments, the compounds of the invention are those represented by formula (III), wherein is selected from the group consisting of

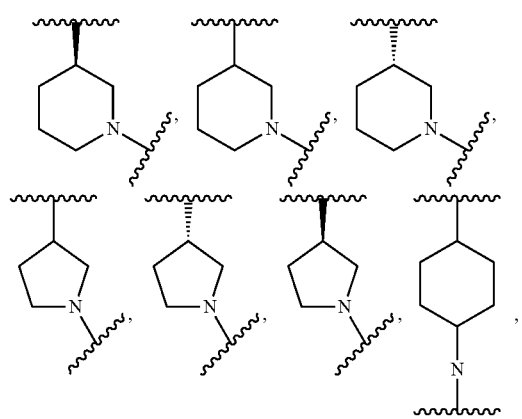

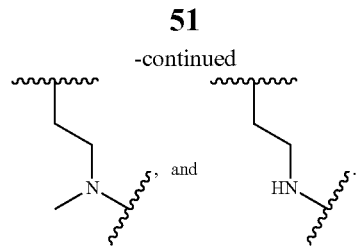

$R_{15}$ is selected from the group consisting of H and lower alkyl; or

Y and $R_{15}$ may join to form a 4-, 5-, or 6-membered heterocyclic ring;

G is selected from the group consisting of H,

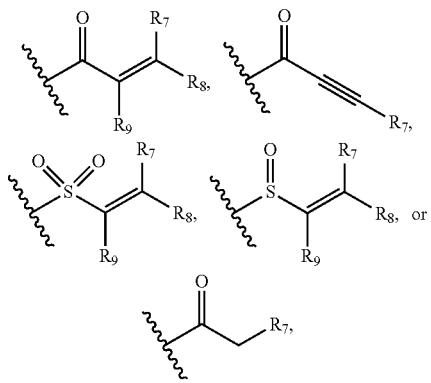

wherein $R_7$, $R_8$ and $R_9$ are independently selected from the group consisting of H, halogen, optionally substituted lower alkyl, and optionally substituted lower heteroalkyl;

In some embodiments, the compounds of the invention are those represented by formula (III), wherein G is selected from the group consisting of

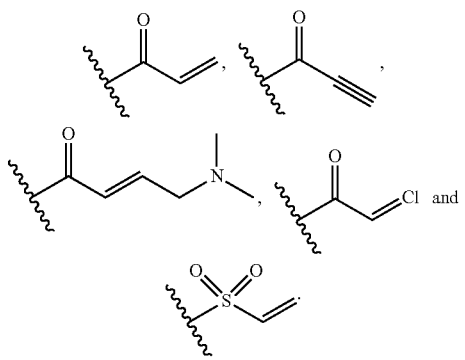

$R_6$ is selected from the group consisting of H, —$C_{1-8}$alkyl, —$(CH_2)_nC_{3-7}$cycloalkyl, —$(CH_2)_nC_{2-9}$heterocycloalkyl, —$(CH_2)_n$—OH, —$(CH_2)_n$—(CHOH)$_n$—H, —$(CH_2)_n$—O—$(CH_2)_n$CH$_3$, —$(CH_2)_n$—S—$(CH_2)_n$CH$_3$, —$(CH_2)_n$—NH$_2$, —$(CH_2)_n$—NH($C_{1-8}$ alkyl), —$(CH_2)_n$—N($C_{1-8}$ alkyl)$_2$, and —C(O)$C_{1-8}$ alkyl;

In some embodiments, the compounds of the invention are those represented by formula (III), wherein $R_6$ is selected from the group consisting of H, Me, Et,

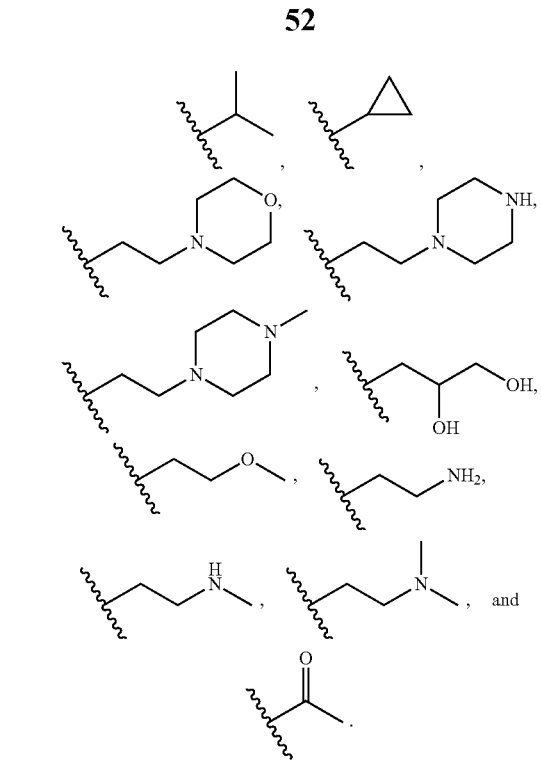

n is 0, 1, 2, 3, or 4.

Another embodiment of this invention provides a compound of Formula (IV),

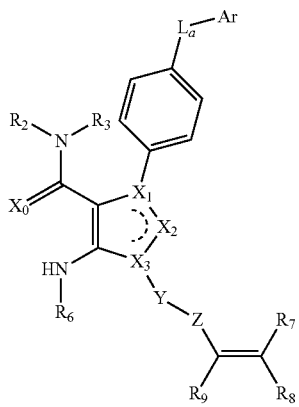

Formula (IV)

or a therapeutically acceptable salt, solvate, metabolite, polymorph, ester, tautomer, or prodrug thereof, wherein:

$L_a$ is selected from the group consisting of a bond, O, S, NH, S(=O), S(=O)$_2$, C(=O), CH$_2$, NHC(O)O, NHC(O) and C(O)NH;

$X_0$ is selected from the group consisting of CH$_2$, O, NH and S;

$X_1$ and $X_3$ are independently selected from the group consisting of C and N;

$X_2$ is selected from the group consisting of CR$_5$, N, and NR$_5$;

$R_5$ is selected from the group consisting of H, halogen, -$L_6$-(optionally substituted $C_{1-3}$alkyl), -$L_6$-(optionally substituted $C_{2-4}$alkenyl), -$L_6$-(optionally substituted aryl), -$L_6$-(optionally substituted heteroaryl) and

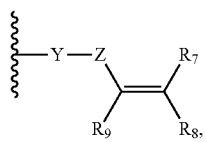

wherein $L_6$ is selected from the group consisting of a bond, O, S, —S(=O)—, —S(=O)$_2$—, NH, C(=O), —NHC(O)O—, —OC(O)NH—, —NHC(O)—, and —C(O)NH—;

$R_2$ and $R_3$ are independently selected from the group consisting of H, and optionally substituted lower alkyl; or $R_2$ and $R_3$ may join to form a 3- to 8-membered heterocyclic ring;

Ar is selected from the group consisting of optionally substituted aryl and optionally substituted heteroaryl;

Y is selected from the group consisting of a bond, alkylene, heteroalkylene, cycloalkylene, heterocycloalkylene, arylene, and heteroarylene;

Z is selected from the group consisting of C(=O), OC(=O), NHC(=O), C(=S), S(=O)$_r$, OS(=O)$_x$, and NHS(=O)$_r$, wherein r is 1 or 2;

$R_6$ is selected from the group consisting of H, halogen, —NH$_2$, —C$_{1-8}$alkyl, —C$_{2-8}$ alkenyl, —C$_{2-8}$alkynyl, —(CH$_2$)$_n$C$_{3-7}$ cycloalkyl, —(CH$_2$)$_n$C$_{2-9}$ heterocycloalkyl, —(CH$_2$)$_n$-phenyl, —(CH$_2$)$_n$-naphthyl, —(CH$_2$)$_n$-heteroaryl, —(CH$_2$)$_n$CO$_2$H, —(CH$_2$)n-(CHOH)n-H, —SR$_{13}$, —OR$_{13}$, —COR$_{13}$, =CH—N(R$_{13}$)$_2$, —(CH$_2$)$_n$—N(R$_{13}$)$_2$, —(CH$_2$)$_n$—N(R$_{13}$)CO$_2$C$_{1-8}$alkyl, —C(O)(CH$_2$)$_n$-aryl, —C(O)C$_{1-8}$alkyl, —C(O)C$_{3-7}$cycloalkyl, —C(O)C$_{2-9}$heterocycloalkyl, —C(O)(CH$_2$)$_n$-heteroaryl, —C(O)CF$_3$, —C(O)(CH$_2$)$_n$—N(R$_{13}$)$_2$, —C(O)N(R$_{13}$)C$_{1-8}$alkyl, —CO$_2$(CH$_2$)$_n$C$_{3-7}$ cycloalkyl, —C(O)N(R$_{13}$)(CH$_2$)$_n$C$_{3-7}$cycloalkyl, —C(O)N(R$_{13}$)(CH$_2$)$_n$C$_{2-7}$heterocycloalkyl, —CO$_2$(CH$_2$)$_n$-heteroaryl, —CO$_2$(CH$_2$)$_n$-phenyl, —C(O)N(R$_{13}$)(CH$_2$)$_n$-phenyl, —CO$_2$(CH$_2$)-naphthyl, —C(O)N(R$_{13}$)(CH$_2$)$_n$-naphthyl, —C(O)N(R$_{13}$)(CH$_2$)$_n$-heteroaryl, —CO$_2$C$_{1-8}$alkyl, —SO$_2$C$_{1-8}$alkyl, —C(S)N(R$_{13}$)(CH$_2$)$_n$-phenyl, —CO$_2$(CH$_2$)$_n$C$_{2-9}$heterocycloalkyl, —SO$_2$C$_{3-7}$cycloalkyl, —SO$_2$C$_{2-9}$ heterocycloalkyl, —SO$_2$phenyl, —SO$_2$naphthyl, —SO$_2$heteroaryl, —S(O)N(R$_{13}$)phenyl, —S—C$_{1-8}$ alkyl, —S—C$_{3-7}$ cycloalkyl, —S—C$_{2-9}$heterocycloalkyl, —S-phenyl, —S-naphthyl and —S-heteroaryl; wherein the said alkyl, alkenyl, alkynyl, cycloalkyl, heterocycloalkyl, aryl, phenyl, naphthyl, heteroaryl, and (CH$_2$) groups are optionally substituted with one or more substituents independently selected from $R_{14}$;

$R_6$ and Y may join to form a 3- to 12-membered ring;

$R_7$ is selected from the group consisting of H, optionally substituted C$_{1-8}$alkyl, optionally substituted C$_{1-4}$heteroalkyl, C$_{1-6}$ alkoxyalkyl, C$_{1-8}$ alkylamino alkyl, optionally substituted C$_{3-6}$ cycloalkyl, optionally substituted aryl, optionally substituted C$_{3-8}$ heterocycloalkyl, optionally substituted heteroaryl, C$_{1-4}$alkyl(aryl), C$_{1-4}$ alkyl(heteroaryl), C$_{1-4}$alkyl (C$_{3-8}$ cycloalkyl), and C$_{1-4}$alkyl(C$_{2-8}$heterocycloalkyl);

$R_8$ and $R_9$ are independently selected from the group consisting of H, optionally substituted C$_{1-8}$alkyl, optionally substituted C$_{1-4}$heteroalkyl, optionally substituted C$_{3-6}$cycloalkyl, and optionally substituted C$_{2-6}$heterocycloalkyl; or $R_8$ and $R_9$ may join to form a bond;

$R_{13}$ is selected from the group consisting of H, —C$_{1-8}$alkyl, —C$_{2-8}$alkenyl, —C$_{2-8}$alkynyl, —(CH$_2$)-phenyl, —C$_{2-8}$alkenyl-phenyl and —(CH$_2$)$_n$CO$_2$H; wherein the said alkyl, alkenyl, alkynyl, phenyl, and (CH$_2$) groups are optionally substituted with one or more substituents independently selected from —OC$_{1-4}$alkyl and —C$_{1-8}$alkyl;

$R_{14}$ is selected from the group consisting of H, oxo, =NH, —CN, —CF$_3$, —OCF$_3$, —C$_{1-6}$ alkyl, —C$_{2-6}$alkenyl, —C$_{2-6}$alkynyl, —(CH$_2$)$_n$C$_{3-6}$ cycloalkyl, —(CH$_2$)$_n$C$_{2-9}$heterocycloalkyl, —(CH$_2$)$_n$OR$_{13}$, —(CH$_2$)$_n$CO$_2$R$_{13}$, —(CH$_2$)$_n$CO$_2$(CH$_2$)$_n$-phenyl, —(CH$_2$)$_n$-phenyl, —(CH$_2$)—O-phenyl, —(CH$_2$)$_n$-naphthyl, —(CH$_2$)$_n$-heteroaryl, —N(R$_{13}$)$_2$, —NR$_3$C(O)R$_{13}$, —NR$_{13}$CO$_2$R$_{13}$, —C(O)phenyl, —C(O)heteroaryl, —SR$_{13}$, —SO$_2$C$_{1-6}$alkyl and —SO$_2$N(R$_{13}$)$_2$; wherein the said alkyl, alkenyl, alkynyl, phenyl, heteroaryl, heterocycloalkyl, naphthyl, cycloalkyl and (CH$_2$) groups are optionally substituted with one or more substituents independently selected from the group consisting of —OH, halogen, —OCH$_3$ and C$_{1-8}$alkyl;

n is 0, 1, 2, 3, 4, 5, 6, 7, or 8.

In some embodiments, the compounds of the invention are those represented by formula (IV), wherein $R_8$ and $R_9$ are independently selected from the group consisting of H, optionally substituted C$_{1-4}$alkyl, and C$_{1-4}$heteroalkyl; or $R_8$ and $R_9$ may join to form a bond.

In some embodiments, the compounds of the invention are those represented by formula (IV), wherein $R_8$ and $R_9$ are both H; or $R_8$ and $R_9$ may join to form a bond.

In some embodiments, the compounds of the invention are those represented by formula (IV), wherein $R_7$ is selected from the group consisting of H, optionally substituted C$_{1-4}$alkyl, C$_{1-4}$heteroalkyl, and C$_{1-8}$alkylaminoalkyl.

In some embodiments, the compounds of the invention are those represented by formula (IV), wherein $R_7$ is H.

In some embodiments, the compounds of the invention are those represented by formula (IV), wherein Z is selected from the group consisting of C(=O), S(=O)$_2$, and S(=O).

In some embodiments, the compounds of the invention are those represented by formula (IV), wherein Z is selected from the group consisting of C(=O) and S(=O)$_2$.

In some embodiments, the compounds of the invention are those represented by formula (IV), wherein Y is selected from the group consisting of optionally substituted C$_{1-8}$alkyl, C$_{2-9}$heteroalkyl, aryl, heteroaryl, 4- to 7-membered cycloalkyl, and 4- to 7-membered heterocycloalkyl.

In some embodiments, the compounds of the invention are those represented by formula (IV), wherein Y is selected from the group consisting of optionally substituted C$_{1-8}$alkyl, 4-, 5-, 6-, or 7-membered cycloalkyl and 4-, 5-, 6-, or 7-membered heterocycloalkyl.

In some embodiments, the compounds of the invention are those represented by formula (IV), wherein $X_1$ is C, $X_2$ and $X_3$ are N; or $X_1$ is N, $X_2$ and $X_3$ are C; or $X_1$ and $X_2$ are C, $X_3$ is N.

In some embodiments, the compounds of the invention are those represented by formula (IV), wherein $X_1$ is C, $X_2$ and $X_3$ are N.

In some embodiments, the compounds of the invention are those represented by formula (IV), wherein $L_a$ is selected from the group consisting of O, S and NH.

In some embodiments, the compounds of the invention are those represented by formula (IV), wherein $L_a$ is O.

In some embodiments, the compounds of the invention are those represented by formula (IV), wherein Ar is aryl or heteroaryl.

In some embodiments, the compounds of the invention are those represented by formula (IV), wherein Ar is phenyl.

In some embodiments, the compounds of the invention are those represented by formula (IV), wherein $X_0$ is selected from the group consisting of O, S and NH.

In some embodiments, the compounds of the invention are those represented by formula (IV), wherein $X_0$ is O.

In some embodiments, the compounds of the invention are those represented by formula (IV), wherein $R_2$ and $R_3$ are independently selected from the group consisting of H and $C_{1-4}$alkyl; or $R_2$ and $R_3$ join to form a 3- to 8-membered heterocyclic ring.

In some embodiments, the compounds of the invention are those represented by formula (IV), wherein $R_2$ and $R_3$ are H; or $R_2$ is H, and $R_3$ is $C_{1-4}$alkyl; or $R_3$ is H, and $R_2$ is $C_{1-4}$ alkyl.

In some embodiments, the compounds of the invention are those represented by formula (IV), wherein $R_6$ is selected from the group consisting of H, —$C_{1-8}$alkyl, —$(CH_2)_n$ $C_{3-7}$cycloalkyl, —$(CH_2)_nC_{2-9}$heterocycloalkyl, —$(CH_2)_n$—OH, —$(CH_2)_n(CHOH)_n$—H, —$(CH_2)_n$—O—$(CH_2)_nCH_3$, —$(CH_2)_n$—S—$(CH_2)_nCH_3$, —$(CH_2)_n$—$NH_2$, —$(CH_2)_n$—$NH(C_{1-8}alkyl)$, —$(CH_2)_n$—$N(C_{1-8}alkyl)_2$, —$C(O)CF_3$, —$C(O)C_{1-8}$alkyl, —$(CH_2)_n$-phenyl, and —$(CH_2)_n$-heteroaryl.

In some embodiments, the compounds of the invention are those represented by formula (IV), wherein $R_6$ is selected from the group consisting of H, —$C_{1-8}$alkyl, —$(CH_2)_n$ $C_{3-7}$cycloalkyl, —$(CH_2)_nC_{2-9}$heterocycloalkyl, —$(CH_2)_n$—OH, —$(CH_2)_n(CHOH)_n$—H, —$(CH_2)_n$—O—$(CH_2)_nCH_3$, —$(CH_2)_n$—S—$(CH_2)_nCH_3$, —$(CH_2)_n$—$NH_2$, —$(CH_2)_n$—$NH(C_{1-8}alkyl)$, —$(CH_2)_n$—$N(C_{1-8}alkyl)_2$, and —$C(O)C_{1-8}$alkyl.

In some embodiments, the compounds of the invention are those represented by formula (IV), wherein n=0, 1, 2, 3, 4, 5, 6, 7, or 8.

In some embodiments, the compounds of the invention are those represented by formula (IV), wherein n=0, 1, 2, 3, or 4.

In some embodiments, the compounds of the present invention are those represented by any of the following formula:

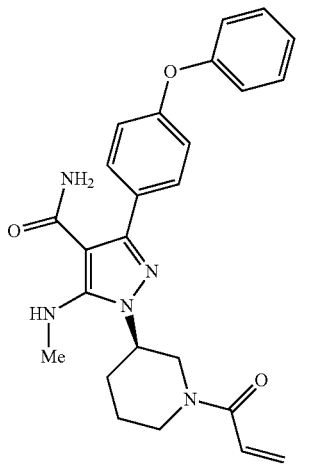

-continued

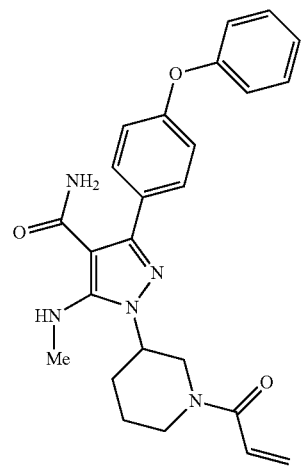

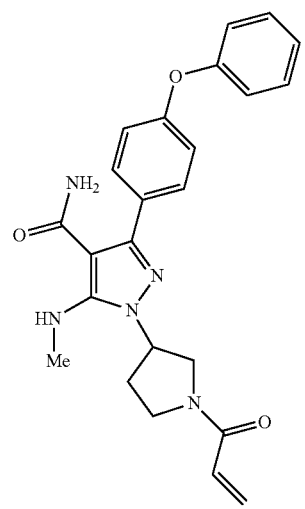

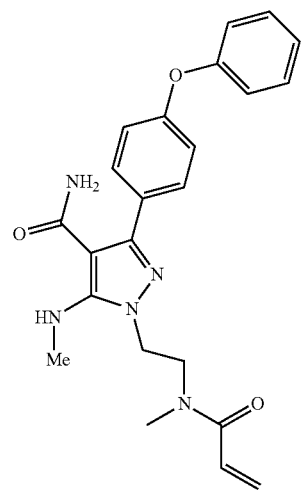

57
-continued
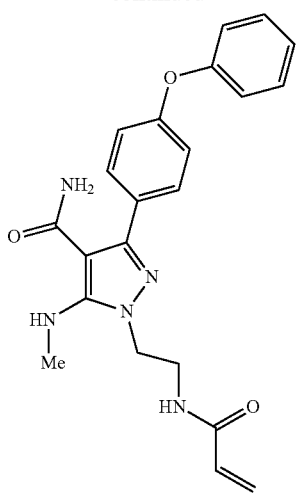
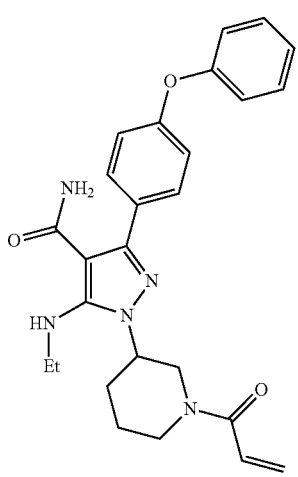
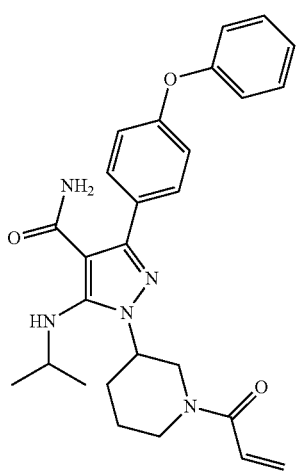
58
-continued
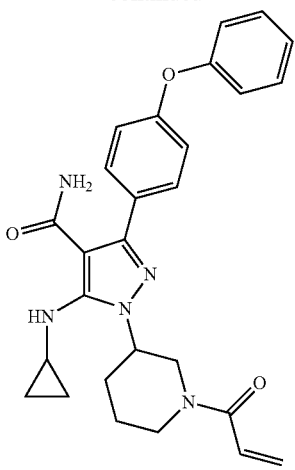
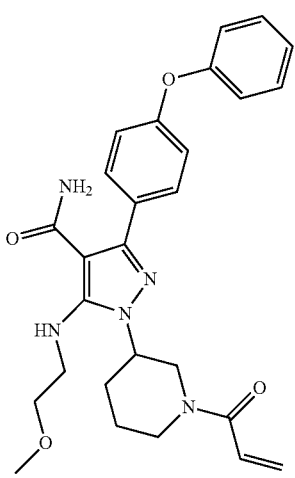
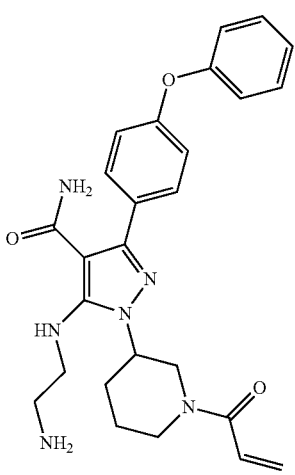

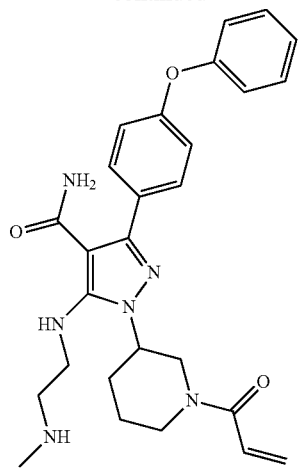
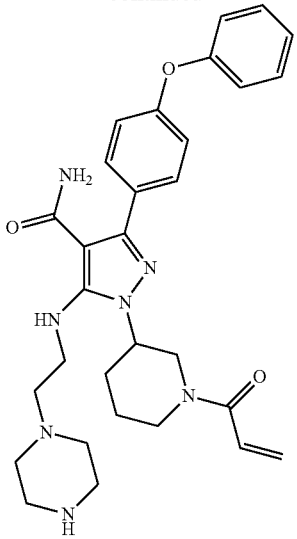
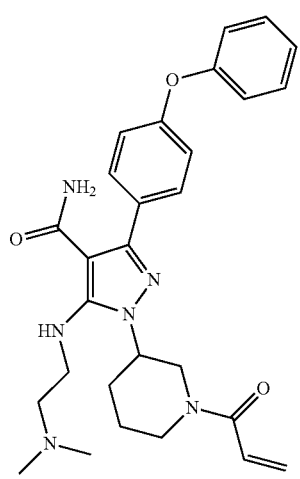
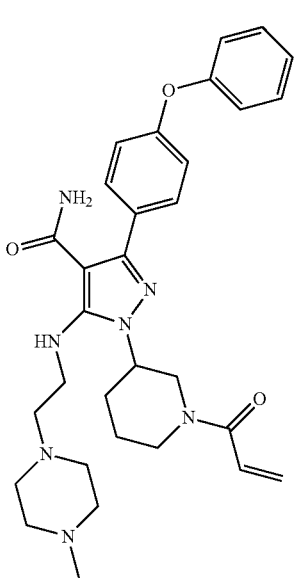
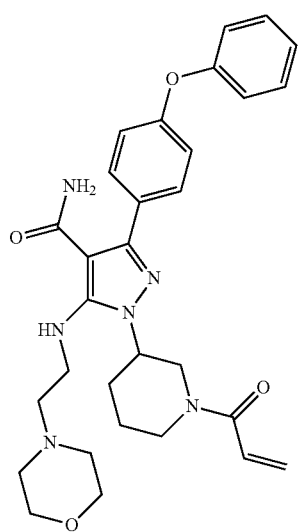
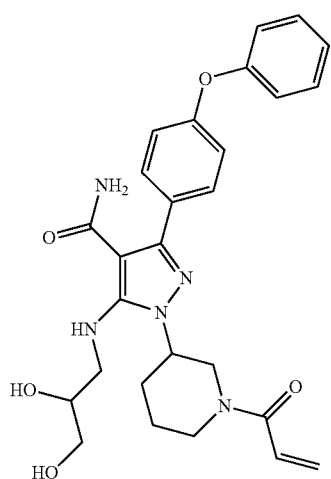

-continued
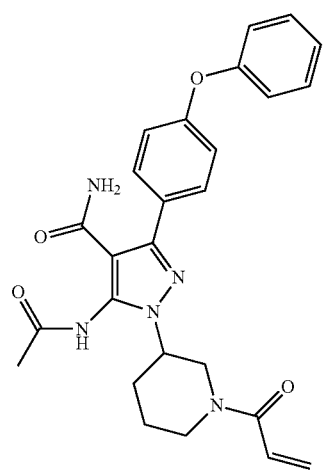
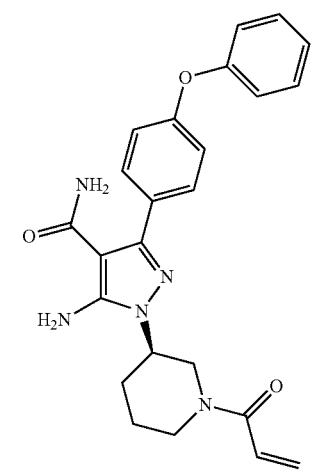
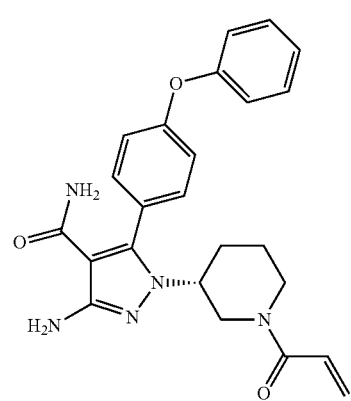
-continued
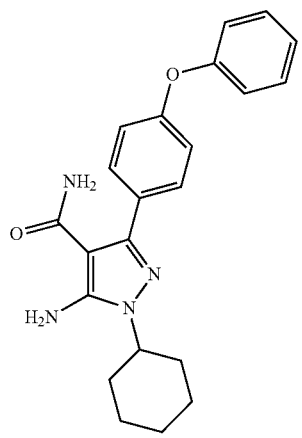
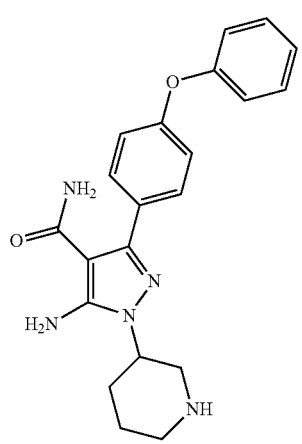
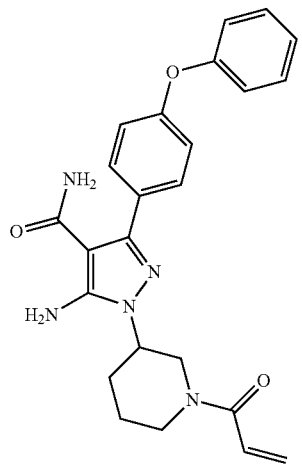

63
-continued
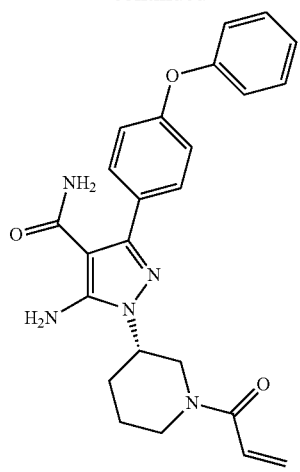
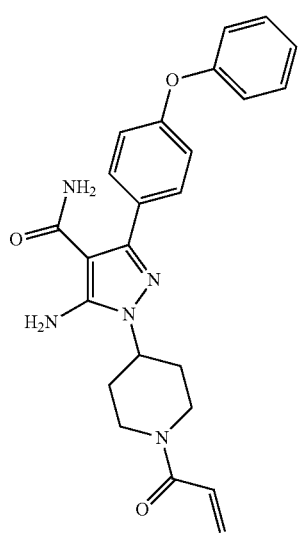
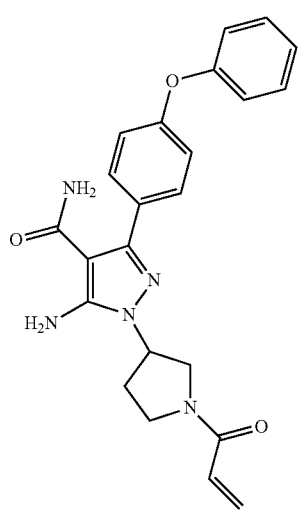
64
-continued
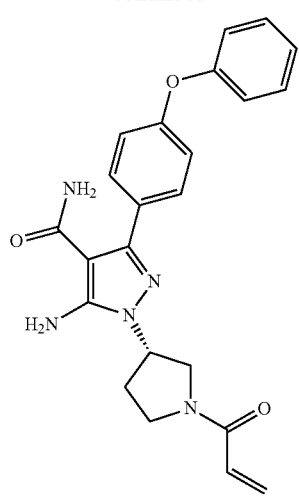
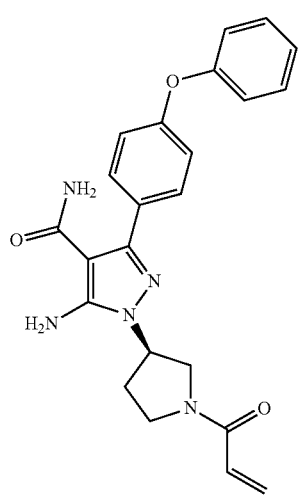
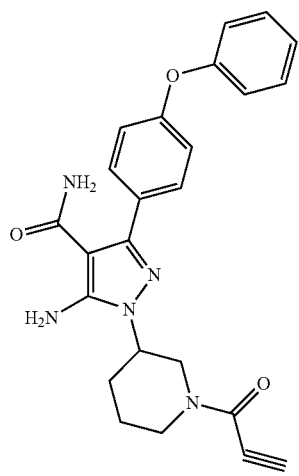

-continued
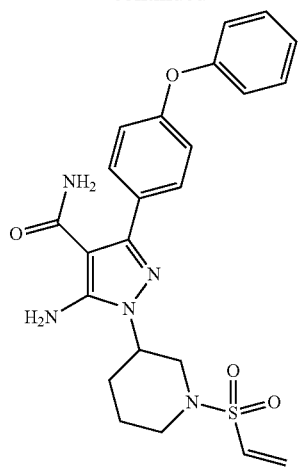
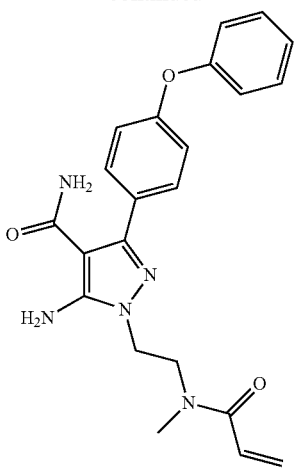
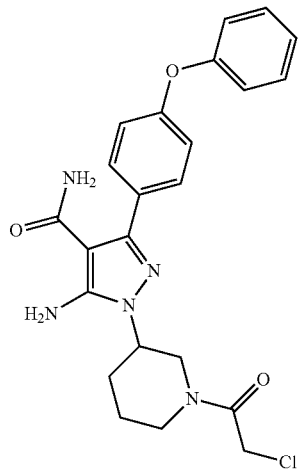
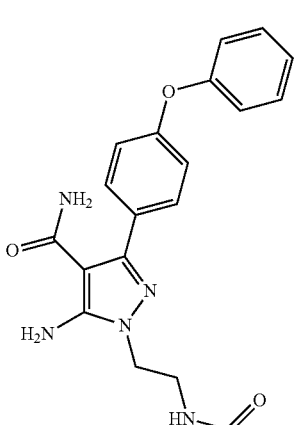
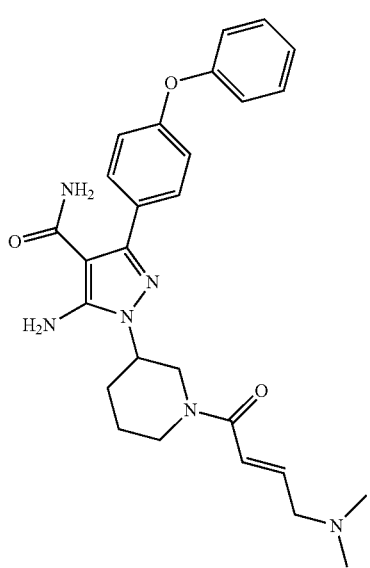
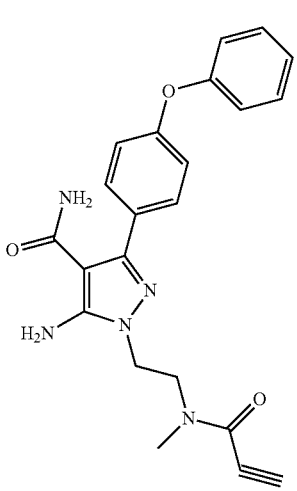

67
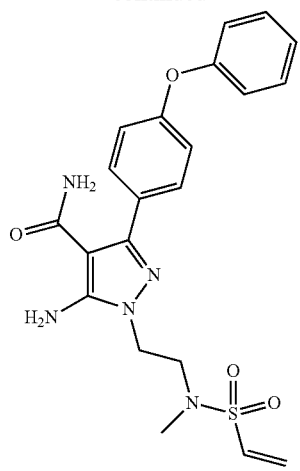
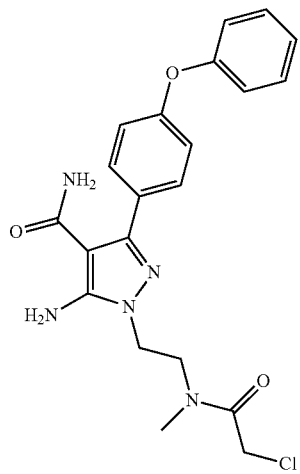
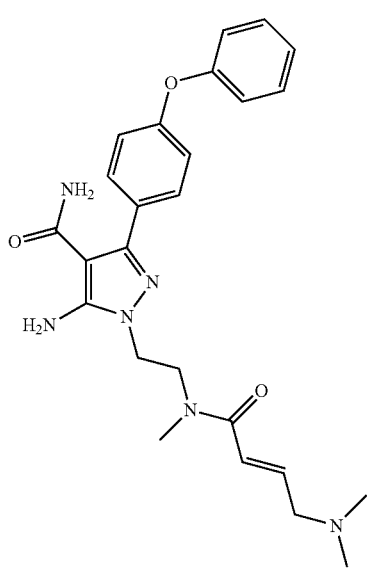
68
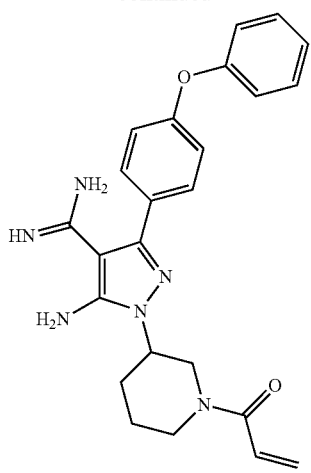
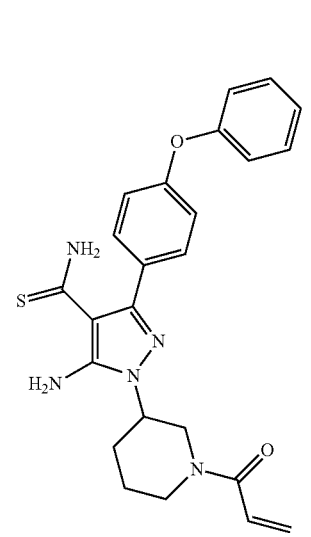
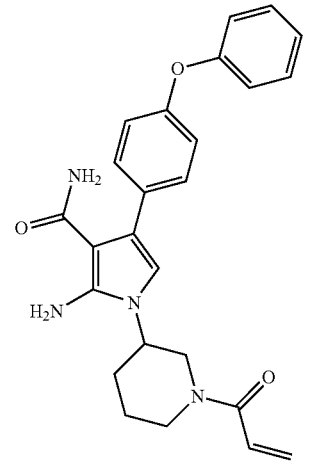

69
-continued
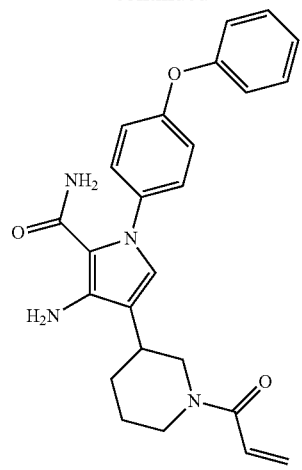
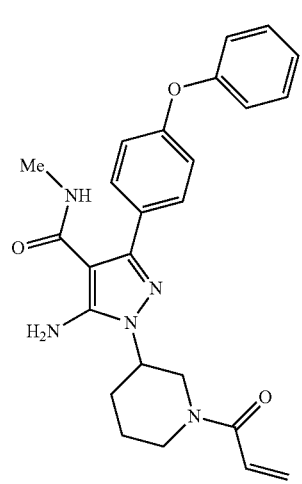
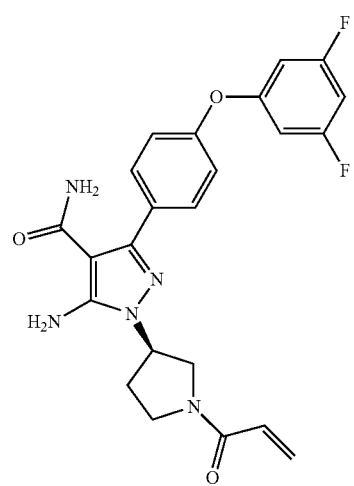
70
-continued
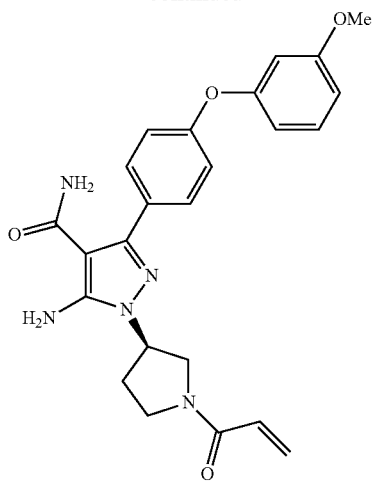
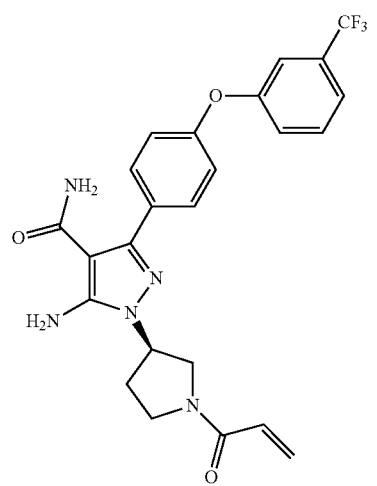

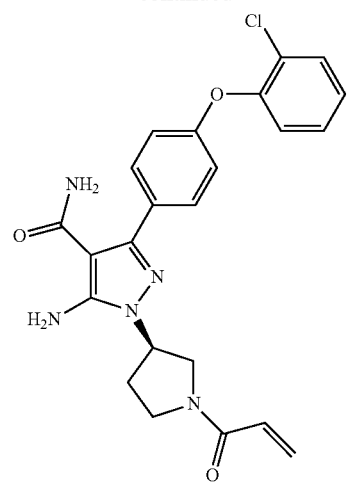
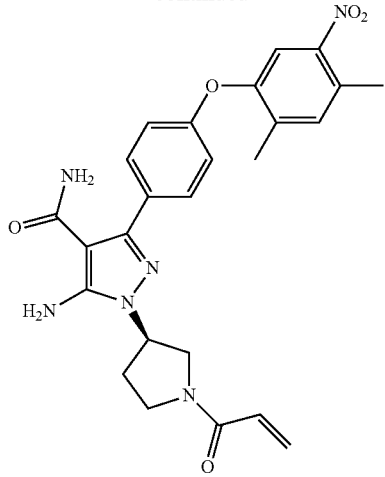

In a further aspect, this application provided pharmaceutical compositions, which include a therapeutically effective amount of at least one of any of the compounds herein, or a pharmaceutically acceptable salt, pharmaceutically active metabolite, pharmaceutically acceptable prodrug, or pharmaceutically acceptable solvate. In certain embodiments, compositions provided herein further include a pharmaceutically acceptable diluents, excipient and/or binder.

In a further aspect, this application also provided methods for treating a patient by administering a compound provided herein. In some embodiments, provided herein is a method of inhibiting the activity of tyrosine kinase(s), such as Btk, or of treating a disease, disorder, or condition, which would benefit from inhibition of tyrosine kinase(s), such as Btk, in a patient, which includes administering to the patient a therapeutically effective amount of at least one of any of the compounds herein, or pharmaceutically acceptable salt, pharmaceutically active metabolite, pharmaceutically acceptable prodrug, or pharmaceutically acceptable solvate.

In a further aspect, this application provided methods for inhibiting Bruton's tyrosine kinase in a subject in need thereof by administering to the subject thereof a composition containing a therapeutically effective amount of at least one compound having the structure of any of Formula (I), Formula (II), Formula (III) and Formula (IV). In some embodiments, the subject in need is suffering from an autoimmune disease, such as lupus and inflammatory bowel disease; from a heteroimmune condition or disease, such as greft versus host disease; from an inflammatory disease, such as asthma; from a cancer, such as diffuse large B cell lymphoma; from a thromboembolic disorder, such as myocardial infarct.

In another aspect, any compounds of Formula (I), Formula (II), Formula (III) and Formula (IV) form a covalent bond with a cysteine residue on Bruton's tyrosine kinase.

In yet another aspect, methods for modulating, including irreversibly inhibiting the activity of Btk or other tyrosine kinases, wherein the other tyrosine kinases share homology with Btk by having a cysteine residue (including a Cys 481 residue) that can form a covalent bond with at least one irreversible inhibitor described herein, in a mammal comprising administering to the mammal at least once an effective amount of at least one compound having the structure of any of Formula (I), Formula (II), Formula (III) or Formula (IV). In another aspect are methods for modulating, including irreversibly inhibiting, the activity of Btk in a mammal comprising administering to the mammal at least once an effective amount of at least one compound having the structure of any of Formula (I), Formula (II), Formula (III) or Formula (IV). In another aspect are methods for treating Btk-dependent or Btk mediated conditions or diseases, comprising administering to the mammal at least once an effective amount of at least one compound having the structure of any Formula (I), Formula (II), Formula (III) or Formula (IV).

DETAILED DESCRIPTION

This invention provided methods for inhibiting Bruton's tyrosine kinase in a subject in need thereof by administering to the subject thereof a composition containing a therapeutically effective amount of at least one compound having the structure of any of Formula (I), Formula (II), Formula (III) and Formula (IV). In some embodiments, the subject in need is suffering from an autoimmune disease, such as lupus and inflammatory bowel disease; from a heteroimmune condition or disease, such as greft versus host disease; from an inflammatory disease, such as asthma; from a cancer, such as diffuse large B cell lymphoma; from a thromboembolic disorder, such as myocardial infarct.

In some embodiments, any compounds of Formula (I), Formula (II), Formula (III) and Formula (IV) form a covalent bond with a cysteine residue on Bruton's tyrosine kinase.

In some embodiments, the irreversible Btk inhibitor compound used for the methods described herein inhibits Btk or a Btk homolog kinase activity with an in vitro $IC_{50}$ of less than 10 µM (e.g., less than 1 µM, less than 100 nM, less than 10 nM, less than 1 nM, less than 0.5 nM).

Described herein are compounds of any of Formula (I), Formula (II), Formula (III), or Formula (IV). Also described herein are pharmaceutically acceptable salts, pharmaceutically acceptable solvates, pharmaceutically active metabolites, and pharmaceutically acceptable prodrugs of such compounds. Pharmaceutical compositions that include at least one such compound or a pharmaceutically acceptable salt, pharmaceutically acceptable solvate, pharmaceutically active metabolite or pharmaceutically acceptable prodrug of such compound, are provided. In some embodiments, when compounds disclosed herein contain an oxidizable nitrogen atom, the nitrogen atom can be converted to an N-oxide by methods well known in the art. In certain embodiments, isomers and chemically protected forms of compounds having a structure represented by any of Formula (I), Formula (II), Formula (III), or Formula (IV), are also provided.

Certain Chemical Terminology

Unless defined otherwise, all technical and scientific terms used herein have the same meaning as is commonly understood by one of skill in the art to which the claimed subject matter belongs. All patents, patent applications, published materials referred to throughout the entire disclosure herein, unless noted otherwise, are incorporated by reference in their entirety. In the event that there is a plurality of definitions for terms herein, those in this section prevail. Wherein reference is made to a URL or other such identifier or address, it is understood that such identifiers can change and particular information on the internet can come and go, but equivalent information can be found by searching the internet or other appropriate reference source. Reference thereto evidences the availability and public dissemination of such information.

It is to be understood that the foregoing general description and the following detailed description are exemplary and explanatory only and are not restrictive of any subject matter claimed. In this application, the use of the singular includes the plural unless specifically stated otherwise. It must be noted that, as used in the specification and the appended claims, the singular forms "a", "an" and "the" include plural referents unless the context clearly dictates otherwise. It should also be noted that use of "or" means "and/or" unless stated otherwise. Furthermore, use of the term "including" as well as other forms, such as "include", "includes", and "included" is not limiting. Likewise, use of the term "comprising" as well as other forms, such as "comprise", "comprises", and "comprised" is not limiting.

The section headings used herein are for organizational purposes only and are not to be construed as limiting the subject matter described. All documents, or portions of documents, cited in the invention including, but not limited to, patents, patent applications, articles, books, manuals, and treatises are hereby expressly incorporated by reference in their entirety for any purpose.

Definition of standard chemistry terms may be found in reference works, including Carey and Sundberg "ADVANCED ORGANIC CHEMISTRY $4^{TH}$ ED." Vols. A (2000) and B (2001), Plenum Press, New York. Unless otherwise indicated, conventional methods of mass spectroscopy, NMR, HPLC, protein chemistry, biochemistry, recombinant DNA techniques and pharmacology, within the skill of the art are employed. Unless specific definitions are provided, the nomenclature employed in connection with, and the laboratory procedures and techniques of, analytical chemistry, synthetic organic chemistry, and medicinal and pharmaceutical chemistry described herein are those known in the art. Standard techniques can be used for chemical syntheses, chemical analyses, pharmaceutical preparation, formulation, and delivery, and treatment of patients. Standard techniques can be used for recombinant DNA, oligonucleotide synthesis, and tissue culture and transformation (e.g., electroporation, lipofection). Reactions and purification techniques can be performed e.g., using kits of manufacturer's specifications or as commonly accomplished in the art or as described herein. The foregoing techniques and procedures can be generally performed of conventional methods well known in the art and as described in various general and more specific references that are cited and discussed throughout the present specification.

Wherein substituent groups are specified by their conventional chemical formulas, written from left to right, they equally encompass the chemically identical substituents that would result from writing the structure from right to left. As a non-limiting example, $CH_2O$ is equivalent to $OCH_2$.

Unless otherwise noted, the use of general chemical terms, such as though not limited to "alkyl," "amine," "aryl," are equivalent to their optionally substituted forms. For example, "alkyl," as used herein, includes optionally substituted alkyl.

The compounds presented herein may possess one or more stereocenters and each center may exist in the R or S configuration, or combinations thereof. Likewise, the compounds presented herein may possess one or more double bonds and each may exist in the E (trans) or Z (cis) configuration, or combinations thereof. Presentation of one particular stereoisomer, regioisomer, diastereomer, enantiomer or epimer should be understood to include all possible stereoisomers, regioisomers, diastereomers, enantiomers or epimers and mixtures thereof. Thus, the compounds presented herein include all separate configurational stereoisomeric, regioisomeric, diastereomeric, enantiomeric, and epimeric forms as well as the corresponding mixtures thereof. Techniques for inverting or leaving unchanged a particular stereocenter, and those for resolving mixtures of stereoisomers are well known in the art and it is well within the ability of one of skill in the art to choose an appropriate method for a particular situation. See, for example, Fumiss et al. (eds.), VOGEL'S ENCYCLOPEDIA OF PRACTICAL ORGANIC CHEMISTRY 5.sup.TH ED., Longman Scientific and Technical Ltd., Essex, 1991, 809-816; and Heller, Acc. Chem. Res. 1990, 23, 128.

It is to be understood that the methods and compositions described herein are not limited to the particular methodology, protocols, cell lines, constructs, and reagents described herein and as such may vary. It is also to be understood that the terminology used herein is for the purpose of describing particular embodiments only, and is not intended to limit the scope of the methods and compositions described herein, which will be limited only by the appended claims.

All publications and patents mentioned herein are incorporated herein by reference in their entirety for the purpose of describing and disclosing, for example, the constructs and methodologies that are described in the publications, which might be used in connection with the methods, compositions and compounds described herein. The publications discussed herein are provided solely for their disclosure prior to the filing date of the present application. Nothing herein is to be construed as an admission that the inventors described herein are not entitled to antedate such disclosure by virtue of prior invention or for any other reason.

The terms "moiety", "chemical moiety", "group" and "chemical group" as used herein, alone or in combination, refer to a specific segment or functional group of a molecule. Chemical moieties are often recognized chemical entities embedded in or appended to a molecule.

The terms "bond" or "single bond" as used herein, alone or in combination, refer to a chemical bond between two atoms, or two moieties when the atoms joined by the bond are considered to be part of larger substructure.

The term "catalytic group" as used herein, alone or in combination, refers to a chemical functional group that assists catalysis by acting to lower the activation barrier to reaction.

The term "optional" or "optionally" means that the subsequently described event or circumstance may or may not occur, and that the description includes instances wherein said event or circumstance occurs and instances in which it does not. For example, "optionally substituted alkyl" means either "alkyl" or "substituted alkyl" as defined below. Further, an optionally substituted group may be un-substituted (e.g., $CH_2CH_3$), fully substituted (e.g., $CF_2CF_3$), mono-substituted (e.g., $CH_2CH_2F$) or substituted at a level anywhere in in-between fully substituted and mono-substituted (e.g., $CH_2CHF_2$, $CF_2CH_3$, $CFHCHF_2$, etc). It will be understood by those skilled in the art with respect to any group containing one or more substituents that such groups are not intended to introduce any substitution or substitution patterns (e.g., substituted alkyl includes optionally substituted cycloalkyl groups, which in turn are defined as including optionally substituted alkyl groups, potentially ad infinitum) that are sterically impractical and/or synthetically non-feasible. Thus, any substituents described should generally be understood as having a maximum molecular weight of about 1,000 daltons, and more typically, up to about 500 daltons (except in those instances wherein macromolecular substituents are clearly intended, e.g., polypeptides, polysaccharides, polyethylene glycols, DNA, RNA and the like).

As used herein, alone or in combination, $C_{1-x}$ includes $C_{1-2}, C_{1-3} \ldots C_{1-x}$.

The term "alkyl" refers to a functional group (or substituent) that is derived from the alkanes by the removal of a hydrogen atom.

The term "heteroalkyl" as used herein, alone or in combination, refers to optionally substituted alkyl structures, as described above, in which one or more of the skeletal chain carbon atoms (and any associated hydrogen atoms, as appropriate) are each independently replaced with a heteroatom (i.e. an atom other than carbon, such as though not limited to oxygen, nitrogen, sulfur, silicon, phosphorous, tin or combinations thereof.

The term "lower alkyl" as used herein, alone or in combination, refers to an alkyl having relatively less carbon atoms, for example having one to about eight carbon atoms, preferably having one to 6, or one to five, or one to four, or one to three, or one to two carbon atoms.

The term "lower heteroalkyl" as used herein, alone or in combination, refers to a heteroalkyl having relatively less carbon atoms, for example having one to about eight carbon atoms, preferably having one to 6, or one to five, or one to four, or one to three, or one to two carbon atoms.

The alkyl group of the compounds described herein may be designated as "$C_{1-4}$alkyl" or similar designations. By way of example only, "$C_{1-4}$alkyl" indicates that there are one to four carbon atoms in the alky chain, e.g., the alkyl chain is selected from among methyl, ethyl, propyl, iso-propyl, n-butyl, iso-butyl, sec-butyl, and t-butyl. Thus $C_{1-4}$alkyl includes $C_{1-2}$alkyl and $C_{1-3}$alkyl. Alkyl groups can be optionally substituted. Examples include, but are not limited to methyl, ethyl, n-propyl, isopropyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-1-pentyl, 3-methyl-1-pentyl, 4-methyl-1-pentyl, 2-methyl-2-pentyl, 3-methyl-2- pentyl, 4-methyl-2-pentyl, 2,2-dimethyl-1-butyl, 3,3-dimethyl-1-butyl, 2-ethyl-1-butyl, n-butyl, isobutyl, sec-butyl, t-butyl, n-pentyl, isopentyl, neopentyl, tert-amyl and hexyl, and longer alkyl groups, such as heptyl, octyl and the like. Whenever it appears herein, a numerical range such as "$C_1$-$C_6$ alkyl" or "$C_{1-6}$ alkyl", means that the alkyl group may consist of 1 carbon atom, 2 carbon atoms, 3 carbon atoms, 4 carbon atoms, 5 carbon atoms or 6 carbon atoms, although the present definition also covers the occurrence of the term "alkyl" wherein no numerical range is designated.

The term "non-cyclic alkyl" as used herein, alone or in combination, refers to an alkyl that is not cyclic, that is a straight or branched chain containing at least one carbon atom. Non-cyclic alkyls can be fully saturated or can contain non-cyclic alkenes and/or alkynes. Non-cyclic alkyls can be optionally substituted.

The term "alkylene" as used herein, alone or in combination, refers to a diradical derived from the above-defined monoradical, alkyl. Examples include, but are not limited to methylene (—$CH_2$—), ethylene (—$CH_2CH_2$—), propylene (—$CH_2CH_2CH_2$—), isopropylene (—$CH(CH_3)CH_2$—) and the like.

The term "heteroalkylene" as used herein, alone or in combination, refers to optionally substituted alkylene structures, as described above, in which one or more of the skeletal chain carbon atoms (and any associated hydrogen atoms, as appropriate) are each independently replaced with a heteroatom (i.e. an atom other than carbon, such as though not limited to oxygen, nitrogen, sulfur, silicon, phosphorous, tin or combinations thereof.

The term "alkenyl" as used herein, alone or in combination, refers to a type of alkyl group in which the first two atoms of the alky group form a double bond that is not part of an aromatic group. That is, an alkenyl group begins with the atoms C(R)=C(R)—R, wherein R refers to the remaining portions of the alkenyl group, which may be the same or different. Alkenyl groups could have 2 to 10 carbons. The alkenyl group could also be a "lower alkenyl" having 2 to 6 carbon atoms.

The term "alkenylene" as used herein, alone or in combination, refers to a diradical derived from the above-defined monoradical alkenyl. Examples include, but are not limited to ethenylene (—CH=CH—), the propenylene isomers (e.g., —$CH_2$CH=CH— and —C($CH_3$)=CH—) and the like.

The term "alkynyl" as used herein, alone or in combination, refers to a type of alkyl group in which the first two atoms of the alkyl group form a triple bond. That is, an alkynyl group begins with the atoms —C≡C—R, wherein R refers to the remaining portions of the alkynyl group, which may be the same or different. The "R" portion of the alkynyl moiety may be branched, straight chain, or cyclic. Alkynyl groups can have 2 to 10 carbons. The alkynyl group could also be a "lower alkynyl" having 2 to 6 carbon atoms.

The term "alkynylene" as used herein, alone or in combination, refers to a diradical derived from the above-defined monoradical, alkynyl. Examples include, but are not limited to ethynylene (—C≡C—), propargylene (—$CH_2$C≡C—) and the like.

The term "alkoxy" as used herein, alone or in combination, refers to a (alkyl)O-group, wherein alkyl is as defined herein.

An "amide" is a chemical moiety with the formula —C(O)NHR or —NHC(O)R, wherein R is selected from among alkyl, cycloalkyl, aryl, heteroaryl and heteroalicyclic. An amide moiety may form a linkage between an amino acid or a peptide molecule and a compound described herein, thereby forming a prodrug.

The term "ester" as used herein, alone or in combination, refers to a chemical moiety with formula —COOR, wherein R is selected from among alkyl, cycloalkyl, aryl, heteroaryl and heteroalicyclic. Any hydroxyl, or carboxyl side chain on the compounds described herein can be esterified.

The term "ring" as used herein, alone or in combination, refers to any covalently closed structure. Ring include, for example, carbocycles, heterocycles, aromatics, and non-aromatics. Ring can be optionally substituted. Rings can be monocyclic or polycyclic.

The term "membered ring" can embrace any cyclic structure. The term "membered" as used herein, alone or in combination, is meant to denote the number of skeletal atoms that constitute the ring. Thus, for example, pyridine and thiopyran are 6-membered rings and cyclophentyl and pyrrole are 5-membered rings.

The terms "carbocyclic" and "carbocycle" as used herein, alone or in combination, refer to a ring wherein each of the atoms forming the ring is a carbon atom. Carbocycle includes aryl and cycloalkyl. The term thus distinguishes carbocycle from heterocycle in which the ring backbone contains at least one atom which is different from carbon. Heterocycle includes heteroaryl and heterocycloalkyl. Carbocycles and heterocycles can be optionally substituted.

The term "cycloalkyl" as used herein, alone or in combination, refers to an optionally substituted, saturated, hydrocarbon monoradical ring, containing from three to about fifteen ring carbon atoms or from three to about ten ring carbon atoms, though may include additional, non-ring carbon atoms as substituents (e.g. methylcyclopropyl). The cycloalkyl may have three to about ten, or three to about eight, or three to about six, or three to five ring atoms. The examples include but not limited to cyclopropyl, cyclobutyl, cyclopentyl, and cyclohexyl.

The term "cycloalkylene" as used herein, alone or in combination, refers to a radical derived from the above-defined monoradical, cycloalkyl.

The term "heterocycloalkyl" as used herein, alone or in combination, refers to cycloalkyl groups which contain at least one heteroatom such as O, S, or N in the ring.

The term "lower heterocycloalkyl" as used herein, alone or in combination, refers to a heterocycloalkyl having relatively less carbon atoms, for example having one to about eight carbon atoms, preferably having one to 6, or one to five, or one to four, or one to three, or one to two carbon atoms.

The term "heterocycloalkylene" as used herein, alone or in combination, refers to a radical derived from the above-defined monoradical, heterocycloalkyl.

The term "aromatic" as used herein, alone or in combination, refers to a planar ring having a delocalized π-electron system containing $4n+2\pi$ electrons, wherein n is an integer. Aromatic rings can be formed from five, six, seven, eight, nine, or more than nine atoms. Aromatics can be optionally substituted. This term "aromatic" includes both carbocyclic aryl and heterocyclic aryl groups. The more, this term "aromatic" also includes monocyclic or fused-ring polycyclic groups.

The term "aryl" as used herein, alone or in combination, refers to an aromatic ring wherein each of the atoms forming the ring is a carbon atom. Aryl ring can be formed by five, six, seven, eight, nine, or more than nine carbon atoms. Aryl groups can be optionally substituted. Examples of aryl groups include, but are not limited to phenyl, naphthalenyl, phenanthrenyl, anthracenyl, fluorenyl, and indenyl. Depending on the structure, an aryl group can be a monoradical or a diradical.

The term "arylene" as used herein, alone or in combination, refers to a diradical derived from the above-defined monoradical, aryl. Examples include, but are not limited to 1,2-phenylene, 1,3-phenylene, 1,4-phenylene, 1,2-naphthylene and the like.

The term "cycloalkyl" as used herein, alone or in combination, refers to a monocyclic or polycyclic radical that contains only carbon and hydrogen, and may be saturated, partially unsaturated, or fully unsaturated. Cycloalkyl groups include groups having from 3 to 10 ring atoms. Illustrative examples of cycloalkyl groups include the following moieties:

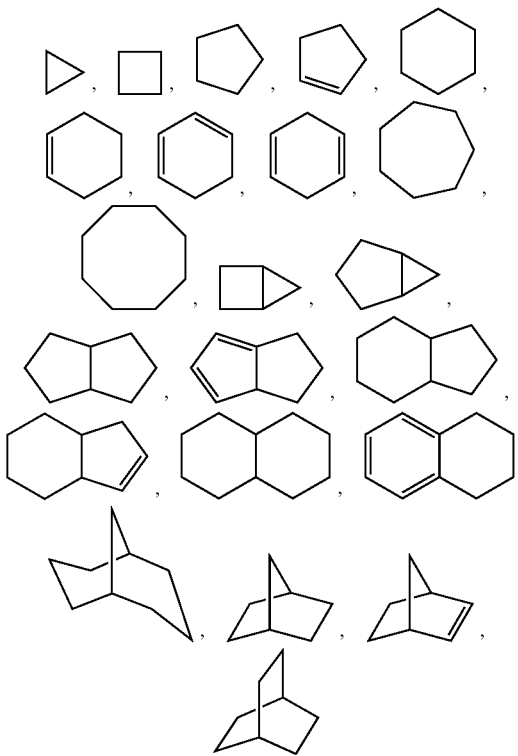

and so on. Depending on the structure, a cycloalkyl group can be a monoradical or a diradical. The cycloalkyl group could also be a "lower cycloalkyl" having 3 to 8 carbon atoms.

The terms "heterocycle" or "heterocycle ring" as used herein, alone or in combination, refers to heteroaromatic and heteroalicyclic groups containing one to four heteroatoms each selected from O, S and N, wherein each heterocyclic group has from 4 to 10 atoms in its ring system, and with the proviso that the ring of said group does not contain two adjacent O or S atoms. Herein, whenever the number of carbon atoms in a heterocycle is indicated, at least one other atom must be present in the ring. Designations such as "$C_{1-6}$heterocycle" refer only to the number of carbon atoms in the ring and do not refer to the total number of atoms in the ring. It is understood that the heterocyclic ring can have additional heteroatoms in the ring. Designations such as "4-6 membered heterocycle" refer to the total number of atoms that are contained in the ring. In heterocycles that have two or more heteroatoms, those two or more heteroatoms can be the same or different from one another. Heterocycles can be optionally substituted. Binding to a heterocycle can be at a heteroatom or via a carbon atom. Non-aromatic heterocyclic groups include groups having only 4 atoms in their ring system, but aromatic heterocyclic groups must have at least 5 atoms in their sing system. The heterocyclic groups include benzo-fused ring systems. An example of a 4-membered heterocyclic group is azetidinyl (derived from azetidine). An example of a 5-membered heterocyclic group is thiazolyl. An example of a 6-membered heterocyclic group is pyridyl, and an example of a 10-membered heterocyclic group is quinolinyl. Examples of non-aromatic heterocyclic groups are pyrrolidinyl, tetrahydrofuranyl, dihydrofuranyl, tetrahydrothienyl, tetrahydropyranyl, dihydropyranyl, tetrahydrothiopyranyl, piperidino, morpholino, thiomorpholino, thioxanyl, piperazinyl, azetidinyl, oxetanyl, thietanyl, homopiperidinyl, oxepanyl, thiepanyl, oxazepinyl, diazepinyl, thiazepinyl, 1,2,3,4-tetrahydropyridinyl, 2-pyrrolinyl, 3-pyrrolinyl, indolinyl, 2H-pyranyl, 4-Hpyranyl, dioxanyl, 1,3-dioxolanyl, pyrazolinyl, dithianyl, dithiolanyl, dihydropyranyl, dihydrothienyl, pyrazolidinyl, imidazolinyl, imidazolidinyl, 3-azabicyclo[3.1.0]hexanyl, 3-azabicyclo[4.1.0]heptanyl, 3H-indolyl and quinolizinyl. Examples of aromatic heterocyclic groups are pyridinyl, imidazolyl, pyrimidinyl, pyrazolyl, triazolyl, pyrazinyl, tetrazolyl, furyl, thienyl, isoxazolyl, thiazolyl, oxzzolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxaziazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl.

The term "phenylene" refers to a phenyl group with an additional hydrogen atom removed. Examples include, but are not limited to 1,2-phenylene, 1,3-phenylene, 1,4-phenylene, and the like.

The term "heteroaryl" as used herein, alone or in combination, refers to optionally substituted aromatic mono-radicals containing from about five to about twenty skeletal ring atoms, wherein one or more of the ring atoms is a heteroatom independently selected from among oxygen, nitrogen, sulfur, phosphorous, silicon, selenium and tin but not limited to these atoms and with the proviso that the ring of said group does not contain two adjacent 0 or S atoms. In embodiments in which two or more heteroatoms are present in the ring, the two or more heteroatoms can be the same as each another, or some or all of the two or more heteroatoms can each be different from the others. The term heteroaryl includes optionally substituted fused and non-fused heteroaryl radicals having at least one heteroatom. The term heteroaryl also includes fused and non-fused heteroaryls having from five to about twelve skeletal ring atoms, as well as those having from five to about ten skeletal ring atoms. Bonding to a heteroaryl group can be via a carbon atom or a heteroatom. Thus, as a non-limiting example, an imidiazole group may be attached to a parent molecule via any of its carbon atoms (imidazol-2-yl, imidazol-4-yl or imidazol-5-yl), or its nitrogen atoms (imidazol-1-yl or imidazol-3-yl). Likewise, a heteroaryl group may be further substituted via any or all of its carbon atoms, and/or any or all of its heteroatoms. A fused heteroaryl radical may contain from two to four fused rings wherein the ring of attachment is a heteroaromatic ring and the other individual rings may be alicyclic, heterocyclic, aromatic, heteroaromatic or any combination thereof. A non-limiting example of a single ring heteroaryl group includes pyridyl; fused ring heteroaryl groups include benzimidazolyl, quinolinyl, acridinyl; and a non-fused bi-heteroaryl group includes bipyridinyl. Further examples of heteroaryls include, without limitation, furanyl, thienyl, oxazolyl, acridinyl, phenazinyl, benzimidazolyl, benzofuranyl, benzoxazolyl, benzothiazolyl, benzothiadiazolyl, benzothiophenyl, benzoxadiazolyl, benzotriazolyl, imidazolyl, indolyl, isoxazolyl, isoquinolinyl, indolizinyl, isothiazolyl, isoindolyloxadiazolyl, indazolyl, pyridyl, pyridazyl, pyrimidyl, pyrazinyl, pyrrolyl, pyrazolyl, purinyl, phthalazinyl, pteridinyl, quinolinyl, quinazolinyl, quinoxalinyl, triazolyl, tetrazolyl, thiazolyl, triazinyl, thiadiazolyl and the like, and their oxides, such as for example pyridyl-N-oxide and the like.

The term "heteroarylene" as used herein, alone or in combination, refers to a diradical derived from the above-defined monoradical heteroaryl. Examples include, but are not limited to pyridinylene and pyrimidinylene.

The terms "non-aromatic heterocycle", "heterocycloalkyl" or "heteroalicyclic" as used herein, alone or in combination refer to a non-aromatic ring wherein one or more atoms forming the ring is a heteroatom. A "non-aromatic heterocycle" or "heterocycloalkyl" group refers to a cycloalkyl group that includes at least one heteroatom selected from nitrogen, oxygen and sulfur. The radicals may be fused with an aryl or heteroaryl. Heterocycloalkyl rings can be formed by three, four, five, six, seven, eight, nine, or more than nine atoms. Heterocycloalkyl rings can be optionally substituted. In certain embodiments, non-aromatic heterocycles contain one or more carbonyl or thiocarbonyl groups such as, for example, oxo- and thio-containing groups. Examples of heterocycloalkyls include, but are not limited to, lactams, lactones, cyclic imides, cyclic thioimides, cyclic carbamates, tetrahydrothiopyran, 4H-pyran, tetrahydropyran, piperidine, 1,3-dioxin, 1,3-dioxane, 1,4-dioxin, 1,4-dioane, piperazine, 1,3-oxathiane, 1,4-oxathiin, 1,4-oxathiane, tetrahydro-1,4-thiazine, 2H-1,2-oxazine, maleimide, succinimide, barbituric acid, thiobarbituric acid, dioxopiperazine, hydantoin, dihydrouracil, morpholine, trioxane, hexahydro-1,3,5-triazine, tetrahydrothiophene, tetrahydrofuran, pyrroline, pyrrolidine, pyrrolidone, pyrrolidione, pyrazoline, pyrazolidine, imidazoline, imidazolidine, 1,3-dioxole, 1,3-dioxolane, 1,3-dithiole, 1,3-dithiolane, isoxazoline, isoxazolidine, oxazoline, oxazolidine, oxazolidinone, thiazoline, thiazolidine, and 1,3-oxathiolane. Illustrative examples of heterocycloalkyl groups, also referred to as non-aromatic heterocycles, include:

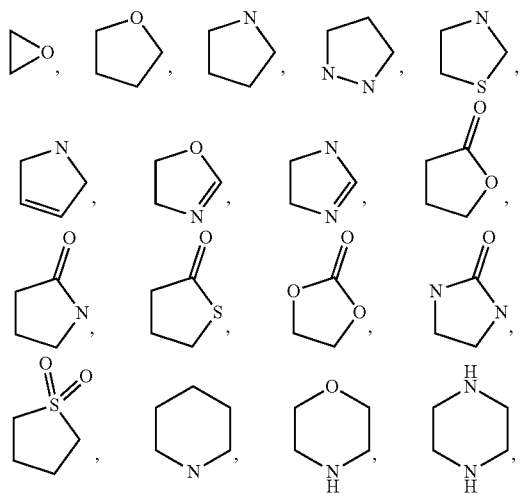

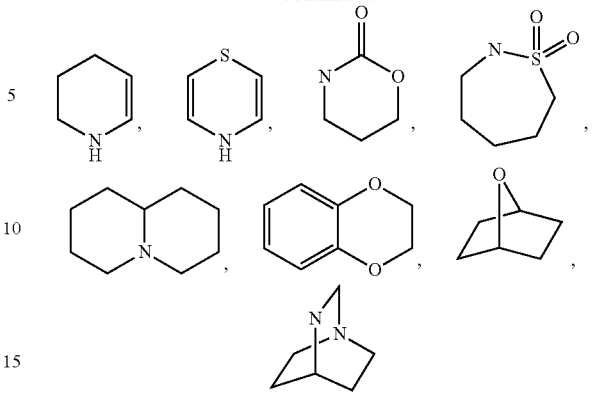

and the like.

The terms "halogen", "halo" or "halide" as used herein, alone or in combination refer to fluoro, chloro, bromo and iodo.

The term "sulfinyl" as used herein, alone or in combination, refers to a —S(=O)—R.

The term "sulfonyl" as used herein, alone or in combination, refers to a —S(=O)$_2$—R.

The terms "sulfonamide", "sulfonamido" and "sulfonamidyl" as used herein, alone or in combination, refer to the groups of —S(O)$_2$NH— and —NHS(=O)$_2$—.

The term "cyano" as used herein, alone or in combination, refers to a group of formula —CN.

Certain Pharmaceutical Terminology

The term "Bruton's tyrosine kinase" as used herein, refer to a Bruton's tyrosine kinase from *Homo sapiens*, as disclosed in, e.g., U.S. Pat. No. 6,326,469 (GenBank Accession No. NP_000052).

The term "Bruton's tyrosine kinase homolog" as used herein, refers to orthologs of Bruton's tyrosine kinase, e.g., the orthologs from mouse (GenBank Accession No. AAB47246), dog (GenBank Accession No. XP_549139), rat (GenBank Accession No. NP_001007799), chicken (GenBank Accession No. NP_989564), or zebra fish (GenBank Accession No. XP_698117), and fusion proteins of any of the foregoing that exhibit kinase activity towards one or more substrates of Bruton's tyrosine kinase (e.g. a peptide substrate having the amino acid sequence "AVLESEEEL-YSSARQ").

The terms "prevention of", "prophylaxis" and "prevent" includes reducing the likelihood of a patient incurring or developing autoimmune disease, heteroimmune disease, inflammatory disease, thromboembolic disorder or cancer (such as, diffuse large B-cell lymphoma, chronic lymphocytic lymphoma, and B-cell prolymphocytic leukemia).

The term "subject", "patient" or "individual" as used herein in reference to individuals suffering from a disease, a disorder, a condition, and the like, encompasses mammals and non-mammals. Examples of mammals include, but are not limited to, any member of the Mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. Examples of non-mammals include, but are not limited to, birds, fish and the like. In one embodiment of the methods and compositions provided herein, the mammal is a human.

The terms "treat," "treating" or "treatment," and other grammatical equivalents as used herein, include alleviating, abating or ameliorating a disease or condition symptoms, preventing additional symptoms, ameliorating or preventing the underlying metabolic causes of symptoms, inhibiting the disease or condition, e.g., arresting the development of the disease or condition, relieving the disease or condition, causing regression of the disease or condition, relieving a condition caused by the disease or condition, or stopping the symptoms of the disease or condition, and are intended to include prophylaxis. The terms further include achieving a therapeutic benefit and/or a prophylactic benefit. By therapeutic benefit is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient may still be afflicted with the underlying disorder. For prophylactic benefit, the compositions may be administered to a patient at risk of developing a particular disease, or to a patient reporting one or more of the physiological symptoms of a disease, even though a diagnosis of this disease may not have been made.

The terms "effective amount", "therapeutically effective amount" or "pharmaceutically effective amount" as used herein, refer to a sufficient amount of at least one agent or compound being administered which will relieve to some extent one or more of the symptoms of the disease or condition being treated. The result can be reduction and/or alleviation of the signs, symptoms, or causes of a disease, or any other desired alteration of a biological system. For example, an "effective amount" for therapeutic uses is the amount of the composition comprising a compound as disclosed herein required to provide a clinically significant decrease in a disease. An appropriate "effective" amount in any individual case may be determined using techniques, such as a dose escalation study.

The terms "administer," "administering", "administration," and the like, as used herein, refer to the methods that may be used to enable delivery of compounds or compositions to the desired site of biological action. These methods include, but are not limited to oral routes, intraduodenal routes, parenteral injection (including intravenous, subcutaneous, intraperitoneal, intramuscular, and intravascular or infusion), topical and rectal administration. Those of skill in the art are familiar with administration techniques that can be employed with the compounds and methods described herein, e.g., as discussed in Goodman and Gilman, The Pharmacological Basis of Therapeutics, current ed.; Pergamon; and Remington's, Pharmaceutical *Sciences* (current edition), Mack Publishing Co., Easton, Pa. In preferred embodiments, the compounds and compositions described herein are administered orally.

The term "acceptable" as used herein, with respect to a formulation, composition or ingredient, means having no persistent detrimental effect on the general health of the subject being treated.

The term "pharmaceutically acceptable" as used herein, refers to a material, such as a carrier or diluent, which does not abrogate the biological activity or properties of the compounds described herein, and is relatively nontoxic, i.e., the material may be administered to an individual without causing undesirable biological effects or interacting in a deleterious manner with any of the components of the composition in which it is contained.

The term "pharmaceutical composition," as used herein, refers to a biologically active compound, optionally mixed with at least one pharmaceutically acceptable chemical component, such as, though not limited to carriers, stabilizers, diluents, dispersing agents, suspending agents, thickening agents, and/or excipients.

The term "carrier" as used herein, refers to relatively nontoxic chemical compounds or agents that facilitate the incorporation of a compound into cells or tissues.

The term "agonist," as used herein, refers to a molecule such as a compound, a drug, an enzyme activator or a hormone modulator which enhances the activity of another molecule or the activity of a receptor site.

The term "antagonist," as used herein, refers to a molecule such as a compound, a drug, an enzyme inhibitor, or a hormone modulator, which diminishes, or prevents the action of another molecule or the activity of a receptor site.

The term "modulate," as used herein, means to interact with a target either directly or indirectly so as to alter the activity of the target, including, by way of example only, to enhance the activity of the target, to inhibit the activity of the target, to limit the activity of the target, or to extend the activity of the target.

The term "modulator," as used herein, refers to a molecule that interacts with a target either directly or indirectly. The interactions include, but are not limited to, the interactions of an agonist and an antagonist.

The term "pharmaceutically acceptable salt" as used herein, refers to salts that retain the biological effectiveness of the free acids and bases of the specified compound and that are not biologically or otherwise undesirable. Compounds described herein may possess acidic or basic groups and therefore may react with any of a number of inorganic or organic bases, and inorganic and organic acids, to form a pharmaceutically acceptable salt. These salts can be prepared in situ during the final isolation and purification of the compounds of the invention, or by separately reacting a purified compound in its free base form with a suitable organic or inorganic acid, and isolating the salt thus formed. Examples of pharmaceutically acceptable salts include those salts prepared by reaction of the compounds described herein with a mineral or organic acid or an inorganic base, such salts including, acetate, acrylate, adipate, alginate, aspartate, benzoate, benzenesulfonate, bisulfate, bisulfite, bromide, butyrate, butyn-1,4-dioate, camphorate, camphorsulfonate, caprylate, chlorobenzoate, chloride, citrate, cyclopentanepropionate, decanoate, digluconate, dihydrogenphosphate, dinitrobenzoate, dodecylsulfate, ethanesulfonate, formate, fumarate, glucoheptanoate, glycerophosphate, glycolate, hemisulfate, heptanoate, hexanoate, hexyne-1,6-dioate, hydroxybenzoate, y-hydroxybutyrate, hydrochloride, hydrobromide, hydro iodide, 2-hydroxyethanesulfonate, iodide, isobutyrate, lactate, maleate, malonate, methanesulfonate, mandelate. metaphosphate, methoxybenzoate, methylbenzoate, monohydrogenphosphate, 1-napthalenesulfonate, 2-napthalenesulfonate, nicotinate, nitrate, palmoate, pectinate, persulfate, 3-phenylpropionate, phosphate, picrate, pivalate, propionate, pyrosulfate, pyrophosphate, propiolate, phthalate, phenylacetate, phenylbutyrate, propanesulfonate, salicylate, succinate, sulfate, sulfite, suberate, sebacate, sulfonate, tartrate, thiocyanate, tosylate undeconate and xylenesulfonate. Other acids, such as oxalic, while not in themselves pharmaceutically acceptable, may be employed in the preparation of salts useful as intermediates in obtaining the compounds of the invention and their pharmaceutically acceptable acid addition salts (See examples at Berge et al., *J. Pharm. Sci.* 1977, 66, 1-19.).

Further, those compounds described herein which may comprise a free acid group may react with a suitable base, such as the hydroxide, carbonate or bicarbonate of a pharmaceutically acceptable metal cation, with ammonia, or with a pharmaceutically acceptable organic primary, secondary or tertiary amine. Representative alkali or alkaline earth salts include the lithium, sodium, potassium, calcium, magnesium, and aluminum salts and the like. Illustrative examples of bases include sodium hydroxide, potassium hydroxide, choline hydroxide, sodium carbonate, IV' $(C_{1-4}$ alkyl$)_4$, and the like. Representative organic amines useful for the formation of base addition salts include ethylamine, diethylamine, ethylenediamine, ethanolamine, diethanolamine, piperazine and the like. It should be understood that the compounds described herein also include the quaternization of any basic nitrogen-containing groups they may contain. Water or oil-soluble or dispersible products may be obtained by such quaternization. See, for example, Berge et al., supra.

The term "solvate" as used herein refers to a combination of a compound of this invention with a solvent molecule formed by solvation. In some embodiments, the solvate refers to a hydrate, e.g., the solvent molecule is a water molecule, the combination of a compound of this invention and water forms a hydrate.

The term "polymorph" or "polymorphism" as used herein refers to a compound of this invention present in different crystal lattice forms.

The term "ester" as used herein refers to a derivative of a compound of this invention derived from an oxoacid group and a hydroxyl group, either one of which can be present at the compound of this invention.

The term "tautomer" as used herein refers to an isomer readily interconverted from a compound of this invention by e.g., migration of a hydrogen atom or proton.

The term "pharmaceutically acceptable derivative or prodrug" as used herein, refers to any pharmaceutically acceptable salt, ester, salt of an ester or other derivative of a compound of this invention, which, upon administration to a recipient, is capable of providing, either directly or indirectly, a compound of this invention or a pharmaceutically active metabolite or residue thereof. Particularly favored derivatives or prodrugs are those that increase the bioavailability of the compounds of this invention when such compounds are administered to a patient (e.g., by allowing orally administered compound to be more readily absorbed into blood) or which enhance delivery of the parent compound to a biological compartment (e.g., the brain or lymphatic system).

The terms "enhance" or "enhancing," as used herein, means to increase or prolong either in potency or duration of a desired effect. Thus, in regard to enhancing the effect of therapeutic agents, the term "enhancing" refers to the ability to increase or prolong, either in potency or duration, the effect of other therapeutic agents on a system.

An "enhancing-effective amount," as used herein, refers to an amount adequate to enhance the effect of another therapeutic agent in a desired system.

The terms "pharmaceutical combination", "administering an additional therapy", "administering an additional therapeutic agent" and the like, as used herein, refer to a pharmaceutical therapy resulting from mixing or combining more than one active ingredient and includes both fixed and non-fixed combinations of the active ingredients. The term "fixed combination" means that at least one of the compounds described herein, and at least one co-agent, are both administered to a patient simultaneously in the form of a single entity or dosage. The term "non-fixed combination" means that at least one of the compounds described herein, and at least one co-agent, are administered to a patient as separate entities either simultaneously, concurrently or sequentially with variable intervening time limits, wherein such administration provides effective levels of the two or more compounds in the body of the patient. These also apply to cocktail therapies, e.g. the administration of three or more active ingredients.

The terms "co-administration", "administered in combination with" and their grammatical equivalents or the like, as used herein, are meant to encompass administration of the selected therapeutic agents to a single patient, and are intended to include treatment regimens in which the agents are administered by the same or different route of administration or at the same or different times. In some embodiments the compounds described herein will be co-administered with other agents. These terms encompass administration of two or more agents to an animal so that both agents and/or their metabolites are present in the animal at the same time. They include simultaneous administration in separate compositions, administration at different times in separate compositions, and/or administration in a composition in which both agents are present. Thus, in some embodiments, the compounds of the invention and the other agent (s) are administered in a single composition.

The term "metabolite," as used herein, refers to a derivative of a compound which is formed when the compound is metabolized.

The term "active metabolite," as used herein, refers to a biologically active derivative of a compound that is formed when the compound is metabolized.

The term "metabolized," as used herein, refers to the sum of the processes (including, but not limited to, hydrolysis reactions and reactions catalyzed by enzymes) by which a particular substance is changed by an organism. Thus, enzymes may produce specific structural alterations to a compound. For example, cytochrome P450 catalyzes a variety of oxidative and reductive reactions while uridine diphosphate glucuronyltransferases catalyze the transfer of an activated glucuronic-acid molecule to aromatic alcohols, aliphatic alcohols, carboxylic acids, amines and free sulphydryl groups. Further information on metabolism may be obtained from *The Pharmacological Basis of Therapeutics*, 9th Edition, McGraw-Hill (1996).

The term "Michael acceptor moiety," as used herein, refers to a functional group that can participate in a Michael reaction, wherein a new covalent bond is formed between a portion of the Michael acceptor moiety and the donor moiety. The Michael acceptor moiety is an electrophile and the "donor moiety" is a nucleophile. The "G" groups presented in any of Formula (I), Formula (II), Formula (III), or Formula (IV) are non-limiting examples of Michael acceptor moieties.

The terms "nucleophile" and "nucleophilic" as used herein, refer to an electron rich compound, or moiety thereof. An example of a nucleophile includes, but in no way is limited to, a cysteine residue of a molecule, such as, for example Cys 481 of Btk.

The terms "electrophile" and "electrophilic" as used herein, refer to an electro poor or electron deficient molecule, or moiety thereof. Examples of electrophiles include, but in no way are limited to, Michael acceptor moieties.

The term "bioavailability" as used herein, refers to the percentage of the weight of compounds disclosed herein, such as, compounds of any of Formula (I), Formula (II), Formula (III), or Formula (IV), dosed that is delivered into the general circulation of the animal or human being studied.

The total exposure ($AUC_{(0-\infty)}$) of a drug when administered intravenously is usually defined as 100% bioavailable (F %).

The term "oral bioavailability" as used herein, refers to the extent to which compounds disclosed herein, such as, compounds of any of Formula (I), Formula (II), Formula (III), or Formula (IV), are absorbed into the general circulation when the pharmaceutical composition is taken orally as compared to intravenous injection.

The term "blood plasma concentration" as used herein, refers to the concentration of compounds disclosed herein, such as, compounds of any of Formula (I), Formula (II), Formula (III), or Formula (IV), in the plasma component of blood of a subject. It is understood that the plasma concentration of compounds of any of Formula (I), Formula (II), Formula (III), or Formula (IV), may vary significantly between subjects, due to variability with respect to metabolism and/or possible interactions with other therapeutic agents. In accordance with one embodiment disclosed herein, the blood plasma concentration of the compounds of any of Formula (I), Formula (II), Formula (III), or Formula (IV), may vary from subject to subject. Likewise, values such as maximum plasma concentration ($C_{max}$) or time to reach maximum plasma concentration ($T_{max}$), or total area under the plasma concentration time curve ($AUC_{(0-\infty)}$) may vary from subject to subject. Due to this variability, the amount necessary to constitute "a therapeutically effective amount" of a compound of any of Formula (I), Formula (II), Formula (III), or Formula (IV), may vary from subject to subject.

The term "target activity" as used herein, refers to a biological activity capable of being modulated by a selective modulator. Certain exemplary target activities include, but are not limited to, binding affinity, signal transduction, enzymatic activity, tumor growth, inflammation or inflammation-related processes, and amelioration of one or more symptoms associated with a disease or condition.

The term "target protein" as used herein, refers to a molecule or a portion of a protein capable of being bound by a selective binding compound. In certain embodiments, a target protein is Btk.

The term "$IC_{50}$" as used herein, refers to an amount, concentration or dosage of a particular test compound that achieves a 50% inhibition of a maximal response, such as inhibition of Btk, in an assay that measures such response.

Compounds

The Btk inhibitor compounds described herein are selective for Btk and kinases having a cysteine residue in an amino acid sequence position of the tyrosine kinase that is homologous to the amino acid sequence position of cysteine 481 in Btk. The irreversible Btk inhibitor compound selectively and irreversibly inhibits an activated form of its target tyrosine kinase, such as a phosphorylated form of the tyrosine kinase.

Irreversible Btk inhibitor compounds can used for the manufacture of a medicament for treating any of the foregoing conditions, such as autoimmune diseases, inflammatory diseases, allergy disorders, B-cell proliferative disorders, or thromboembolic disorders. Inhibitor compounds described herein include a Michael acceptor moiety.

Described herein are compounds of formula (IV), pharmaceutically acceptable salts, solvates, metabolites, polymorphs, esters, tautomers or prodrugs thereof,

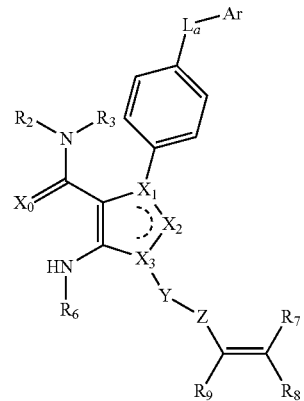

Formula (IV)

wherein:

$L_a$ is selected from the group consisting of a bond, O, S, NH, S(=O), S(=O)$_2$, C(=O), CH$_2$, NHC(O)O, NHC(O) and C(O)NH;

$X_0$ is selected from the group consisting of CH$_2$, O, NH and S;

$X_1$ and $X_3$ are independently selected from the group consisting of C and N;

$X_2$ is selected from the group consisting of CR$_5$, N, and NR$_5$;

$R_5$ is selected from the group consisting of H, halogen, -L$_6$-(optionally substituted C$_{1-3}$alkyl), -L$_6$-(optionally substituted C$_{2-4}$alkenyl), -L$_6$-(optionally substituted aryl), -L$_6$-(optionally substituted heteroaryl) and

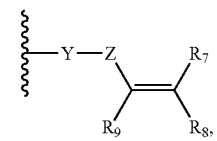

wherein L$_6$ is selected from the group consisting of a bond, O, S, —S(=O)—, —S(=O)$_2$—, NH, C(=O), —NHC(O) O—, —OC(O)NH—, —NHC(O)—, and —C(O)NH—;

R$_2$ and R$_3$ are independently selected from the group consisting of H, and optionally substituted lower alkyl; or R$_2$ and R$_3$ may join to form a 3- to 8-membered heterocyclic ring;

Ar is selected from the group consisting of optionally substituted aryl and optionally substituted heteroaryl;

Y is selected from the group consisting of a bond, alkylene, heteroalkylene, cycloalkylene, heterocycloalkylene, arylene, and heteroarylene;

Z is selected from the group consisting of C(=O), OC(=O), NHC(=O), C(=S), S(=O)$_r$, OS(=O)$_r$, and NHS(=O)$_r$, wherein r is 1 or 2;

R$_6$ is selected from the group consisting of H, halogen, —NH$_2$, —C$_{1-8}$alkyl, —C$_{2-8}$alkenyl, —C$_{2-8}$alkynyl, —(CH$_2$)$_n$C$_{3-7}$cycloalkyl, —(CH$_2$)$_n$C$_{2-9}$heterocycloalkyl, —(CH$_2$)$_n$-phenyl, —(CH$_2$)$_n$-naphthyl, —(CH$_2$)$_n$-heteroaryl, —(CH$_2$)$_n$CO$_2$H, —(CH$_2$)n-(CHOH)n-H, —SR$_{13}$, —OR$_{13}$, —COR$_{13}$, =CH—N(R$_{13}$)$_2$, —(CH$_2$)$_n$—N(R$_{13}$)$_2$, —(CH$_2$)$_n$—N(R$_{13}$)CO$_2$C$_{1-8}$alkyl, —C(O)(CH$_2$)$_n$-aryl, —C(O)C$_{1-8}$alkyl, —C(O)C$_{3-7}$cycloalkyl, —C(O)C$_{2-9}$heterocycloalkyl, —C(O)(CH$_2$)$_n$-heteroaryl, —C(O)CF$_3$, —C(O)(CH$_2$)$_n$—N(R$_{13}$)$_2$, —C(O)N(R$_{13}$)C$_{1-8}$alkyl, —CO$_2$(CH$_2$)$_n$C$_{3-7}$ cycloalkyl, —C(O)N(R$_{13}$)(CH$_2$)$_n$C$_{3-7}$cycloalkyl, —C(O)N($R_{13}$)($CH_2$)$_n$$C_{2-7}$heterocycloalkyl, —$CO_2$($CH_2$)$_n$-heteroaryl, —$CO_2$($CH_2$)$_n$-phenyl, —C(O)N($R_{13}$)($CH_2$)$_n$-phenyl, —$CO_2$($CH_2$)$_n$-naphthyl, —C(O)N($R_{13}$)($CH_2$)$_n$-naphthyl, —C(O)N($R_{13}$)($CH_2$)$_n$-heteroaryl, —$CO_2$$C_{1-8}$alkyl, —$SO_2$$C_{1-8}$ alkyl, —C(S)N($R_{13}$)($CH_2$)$_n$-phenyl, —$CO_2$($CH_2$)$_n$$C_{2-9}$heterocycloalkyl, —$SO_2$$C_{3-7}$cycloalkyl, —$SO_2$$C_{2-9}$ heterocycloalkyl, —$SO_2$phenyl, —$SO_2$naphthyl, —$SO_2$heteroaryl, —S(O)N($R_{13}$)phenyl, —S—$C_{1-8}$alkyl, —S—$C_{3-7}$ cycloalkyl, —S—$C_{2-9}$heterocycloalkyl, —S-phenyl, —S-naphthyl and —S-heteroaryl; wherein the said alkyl, alkenyl, alkynyl, cycloalkyl, heterocycloalkyl, aryl, phenyl, naphthyl, heteroaryl, and ($CH_2$) groups are optionally substituted with one or more substituents independently selected from $R_{14}$;

$R_6$ and Y may join to form a 3- to 12-membered ring;

$R_7$ is selected from the group consisting of H, optionally substituted $C_{1-4}$alkyl, optionally substituted $C_{1-4}$heteroalkyl, $C_{1-6}$ alkoxyalkyl, $C_{1-8}$ alkylamino alkyl, optionally substituted $C_{3-6}$ cycloalkyl, optionally substituted aryl, optionally substituted $C_{2-8}$ heterocycloalkyl, optionally substituted heteroaryl, $C_{1-4}$alkyl(aryl), $C_{1-4}$ alkyl(heteroaryl), $C_{1-4}$alkyl ($C_{3-8}$ cycloalkyl), and $C_{1-4}$alkyl($C_{2-8}$heterocycloalkyl);

$R_8$ and $R_9$ are independently selected from the group consisting of H, optionally substituted $C_{1-4}$alkyl, optionally substituted $C_{1-4}$heteroalkyl, optionally substituted $C_{3-6}$cycloalkyl, and optionally substituted $C_{2-6}$heterocycloalkyl; or $R_8$ and $R_9$ may join to form a bond;

$R_{13}$ is selected from the group consisting of H, —$C_{1-8}$alkyl, —$C_{2-8}$alkenyl, —$C_{2-8}$alkynyl, —($CH_2$)-phenyl, —$C_{2-8}$alkenyl-phenyl and —($CH_2$)$_n$$CO_2$H; wherein the said alkyl, alkenyl, alkynyl, phenyl, and ($CH_2$) groups are optionally substituted with one or more substituents independently selected from —$OC_{1-4}$alkyl and —$C_{1-4}$alkyl;

$R_{14}$ is selected from the group consisting of H, oxo, =NH, —CN, —$CF_3$, —$OCF_3$, —$C_{1-6}$ alkyl, —$C_{2-6}$alkenyl, —$C_{2-6}$alkynyl, —($CH_2$)$_n$$C_{3-6}$ cycloalkyl, —($CH_2$)$_n$$C_{2-9}$heterocycloalkyl, —($CH_2$)$_n$$OR_{13}$, —($CH_2$)$_n$$CO_2R_{13}$, —($CH_2$)$_n$$CO_2$($CH_2$)$_n$-phenyl, —($CH_2$)$_n$-phenyl, —($CH_2$)—O-phenyl, —($CH_2$)$_n$-naphthyl, —($CH_2$)$_n$-heteroaryl, —N($R_{13}$)$_2$, —$NR_3$C(O)$R_{13}$, —$NR_{13}$$CO_2R_{13}$, —C(O)phenyl, —C(O)heteroaryl, —$SR_{13}$, —$SO_2C_{1-6}$alkyl and —$SO_2$N($R_{13}$)$_2$; wherein the said alkyl, alkenyl, alkynyl, phenyl, heterocycloalkyl, naphthyl, cycloalkyl and ($CH_2$) groups are optionally substituted with one or more substituents independently selected from the group consisting of —OH, halogen, —$OCH_3$ and $C_{1-4}$ alkyl;

n is 0, 1, 2, 3, 4, 5, 6, 7, or 8;

m is 1, 2, 3, 4, 5, 6, 7, or 8.

Methods for synthesizing the compounds described herein are provided. In some embodiments, the compounds described herein can be prepared by the methods described below. The procedures and examples below are intended to illustrate those methods. Neither the procedures nor the examples should be construed as limiting the invention in any way. Compounds described herein may also be synthesized using standard synthetic techniques known to those of skill in the art or using methods known in the art in combination with methods described herein.

SYNTHETIC PROCEDURES AND EXAMPLES

Scheme 1

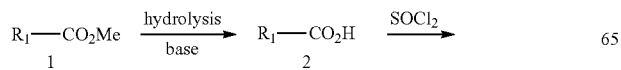

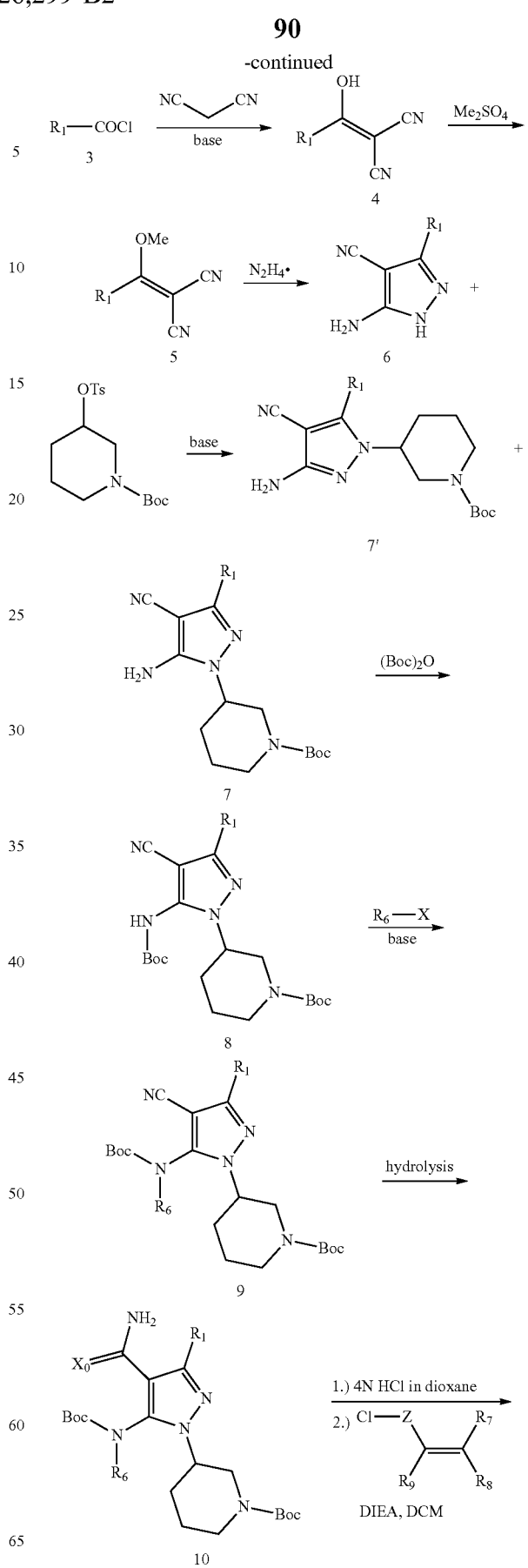

-continued

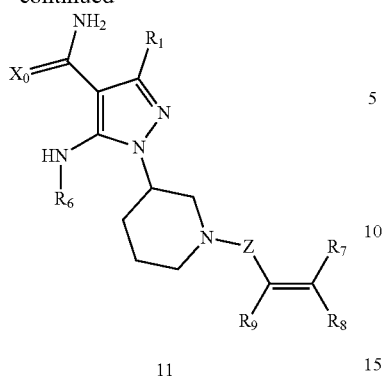

A non-limiting example of a synthetic approach towards the preparation of compounds of any of Formula (I), Formula (II), Formula (III) or Formula (IV) is shown in Scheme I. The products of the reactions may be isolated and purified, if desired, using conventional techniques, including, but not limited to, filtration, distillation, crystallization, chromatography and the like. The starting material used for the synthesis of the compounds described herein may be synthesized or can be obtained from commercial sources, such as, but not limited to Aldrich or Sigma. Such materials may be characterized using conventional means, including physical constants and spectral data. Compounds described herein may be prepared using the synthetic methods described herein as a single isomer or a mixture of isomers.

The starting material 1 was purchased from commercial sources directly or synthesized by oneself. Hydrolysis of 1 using base, such as NaOH in EtOH/H$_2$O at 70° C. for 1 h to get intermediate 2, which was treated with sulfurous dichloride to give intermediate 3. Malononitrile was reacted with intermediate 3 using base, such as NaH, in dry THF at 0° C. to get intermediate 4, which was treated with dimethyl sulfate to get intermediate 5. Hydrazine hydrate was reacted with intermediate 5 to give an entry into the synthesis of compounds of Formula (I), Formula (II), Formula (III) and Formula (IV). In one embodiment, base (such as Cs$_2$CO$_3$) mediated SN$_2$ reaction was carried out between Ts-protected N-Boc-3-hydroxypiperdine (as non-limiting example) and intermediate 6 to give the pure Boc-protected (tert-butyloxycarbonyl) intermediate 7 and 7'. Intermediate 7 was treated with (Boc)$_2$O in a base, such as pyridine, to give compound 8. Intermediate 9 was obtained via SN$_2$ reaction with R$_6$X (such as R$_6$F, R$_6$Cl, R$_6$Br or R$_6$I) using base, such as K$_2$CO$_3$ in DMF. Hydrolysis of 9 (such as, con.H$_2$SO$_4$, base/H$_2$O$_2$, or O,O-diethyl dithiophosphate) provided intermediate 10 with good yield. De-protection of intermediate 10 with an acid (such as TFA), followed by the reaction with, but not limited to, an acid chloride, such as, but not limited to, acryloyl chloride, gave the final product 11.

Example 1

1-(1-acryloylpiperidin-3-yl)-5-(methylamino)-3-(4-phenoxyphenyl)-1H-pyrazole-4-carboxamide

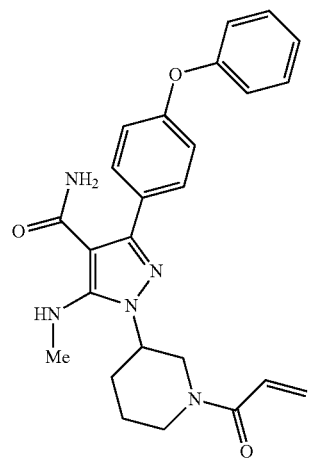 [SMILES: C=CC(=O)N1CCCC(n2nc(-c3ccc(Oc4ccccc4)cc3)c(C(N)=O)c2NC)C1]

Step A: Methyl 4-phenoxybenzoate

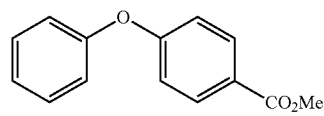 [SMILES: COC(=O)c1ccc(Oc2ccccc2)cc1]

To a stirred solution of methyl 4-iodobenzoate (400 g, 1.0 eq) and phenol (172.4 g, 1.2 eq) in 1500 mL DMF at r.t. was added Cs$_2$CO$_3$ (995 g, 2.0 eq), CuI (58.1 g, 20%) and N,N-dimethylglycine (63.0 g, 40%). After addition was completed, the reaction mixture was heated to 110° C. and stirred at that temperature overnight. Water was added and the mixture was extracted with organic solvent of Petrol/EtOAc (9:1). The organic extract was washed with 1N NaOH, water and brine, dried with anhydrous Na$_2$SO$_4$, evaporated the organic solvent to give the product as a white solid directly (192.5 g, 55%). $^1$H NMR (400 MHz, CDCl$_3$) δ 7.99-8.01 (m, 2H), 7.37-7.41 (m, 2H), 7.17-7.21 (m, 1H), 7.05-7.08 (m, 2H), 6.97-7.00 (m, 2H), 3.90 (s, 3H).

Step B: 4-phenoxybenzoic Acid

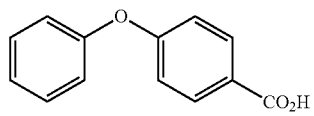 [SMILES: O=C(O)c1ccc(Oc2ccccc2)cc1]

To a stirred solution of methyl 4-phenoxybenzoate (580 g, 1.0 eq) in 1000 mL EtOH at r.t. was added NaOH (203 g, 2.0 eq) in 500 mL water. After addition was completed, the reaction mixture was heated to 70° C. and stirred at that temperature for 1 hour. The solvent of EtOH was removed by concentration, and then ice water was added. After pH was adjusted to 2-3, the mixture was stirred at r.t. for 15 min.

Step C: 4-phenoxybenzoyl Chloride

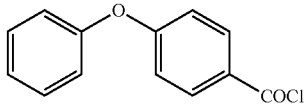 [SMILES: O=C(Cl)c1ccc(Oc2ccccc2)cc1]

A stirred solution of 4-phenoxybenzoic acid (160 g, 1.0 eq) in 500 mL sulfurous dichloride was refluxed at 90° C. overnight. Sulfurous dichloride was removed and the product was obtained as an oil, which was used for the next step without further purification (173 g, 99%). $^1$H NMR (400 MHz, CDCl$_3$) δ 8.07-8.09 (m, 2H), 7.41-7.45 (m, 2H), 7.23-7.27 (m, 1H), 7.08-7.11 (m, 2H), 7.00-7.02 (m, 2H).

Step D:
2-(hydroxy(4-phenoxyphenyl)methylene)malononitrile

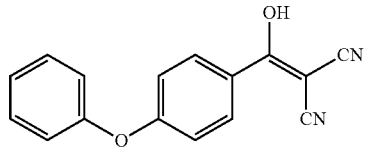 [SMILES: N#CC(C#N)=C(O)c1ccc(Oc2ccccc2)cc1]

To a stirred solution of malononitrile (123.4 g, 2.5 eq) in 1500 mL dry THF at 0° C. was added NaH (100 g, 60%, 4.0 eq). After addition was completed, the reaction mixture was let warm up to room temperature and stirred at that temperature for 1 hour, and then cooled to 0° C. 4-Phenoxybenzoyl chloride (173 g, 1.0 eq) in 500 mL dry THF was added to the reaction mixture slowly. After addition was completed, the reaction mixture was stirred at that temperature for 1 hour. Water was added to quench the reaction very slowly. After completed, 500 mL saturated NH$_4$Cl solvent was added to mixture. The mixture was extracted with EtOAc. The organic extract was washed with water and brine, dried with anhydrous Na$_2$SO$_4$, evaporated the organic solvent to give the crude product as a red oil, which was stirred in mixture of petrol and EtOAc violently to give gray white solid and recrystallized in 1,4-dioxane to get pure product as a whit solid (180 g, 98%). $^1$H NMR (400 MHz, DMSO) δ 7.60-7.64 (m, 2H), 7.40-7.44 (m, 2H), 7.16-7.20 (m, 1H), 7.05-7.07 (m, 2H), 6.92-6.96 (m, 2H).

Step E:
2-(methoxy(4-phenoxyphenyl)methylene)malononitrile

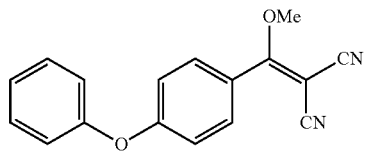 [SMILES: COC(=C(C#N)C#N)c1ccc(Oc2ccccc2)cc1]

To a stirred solution of 2-(hydroxy(4-phenoxyphenyl) methylene)malononitrile (500 g, 1.0 eq) in 2000 mL solvent of dioxane at r.t. was added NaHCO$_3$ (480 g, 3.0 eq) and dimethyl sulfate (360 g, 271 mL, 1.5 eq). After addition was completed, the reaction mixture was heated to 80° C., and stirred at that temperature for 3 h. The organic solvent was removed, and water was added. The mixture was extracted with EtOAc. The organic extract was washed with water and brine, dried with anhydrous Na$_2$SO$_4$, and evaporated the organic solvent to give the crude product which was recrystallized in hexane/EtOAc (1:1) to give the pure product as a gray yellow solid (420 g, 88%). $^1$H NMR (400 MHz, CDCl$_3$) δ 7.48-7.51 (m, 2H), 7.41-7.45 (m, 2H), 7.25-7.27 (m, 1H), 7.07-7.11 (m, 4H), 3.99 (s, 3H).

Step F: 5-amino-3-(4-phenoxyphenyl)-1H-pyrazole-4-carbonitrile

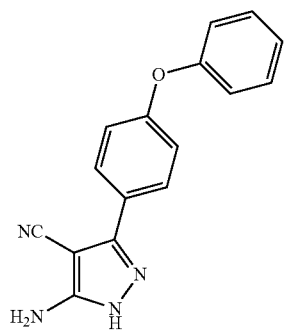 [SMILES: N#Cc1c(-c2ccc(Oc3ccccc3)cc2)n[nH]c1N]

To a stirred solution of 2-(methoxy(4-phenoxyphenyl) methylene)malononitrile (78.5 g, 1.0 eq) in 400 mL EtOH at r.t. was added hydrazine hydrate (50 mL, 85%, 3.0 eq). After addition was completed, the reaction was refluxed at 90° C. for 2 h. The mixture was concentrated to crude product and recrystallized in hexane to give pure product as a white solid (72.4 g, 88%). $^1$H NMR (400 MHz, DMSO) δ 7.78-7.81 (m, 2H), 7.40-7.44 (m, 2H), 7.16-7.20 (m, 1H), 7.06-7.11 (m, 4H), 6.26 (brs, 2H).

Step G: Tert-butyl 3-(5-amino-4-cyano-3-(4-phenoxyphenyl)-1H-pyrazol-1-yl)-piperidine-1-carboxylate

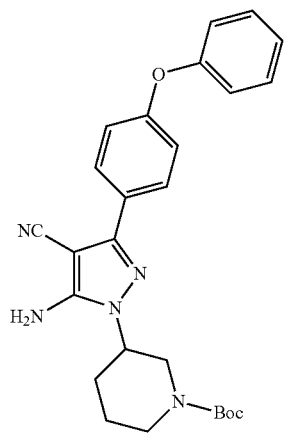 [SMILES: CC(C)(C)OC(=O)N1CCCC(n2nc(-c3ccc(Oc4ccccc4)cc3)c(C#N)c2N)C1]

Tert-butyl 3-(tosyloxy)piperidine-1-carboxylate

To a stirred solution of tert-butyl 3-hydroxypiperidine-1-carboxylate (50 g, 1.0 eq), TsCl (4-methylbenzene-1-sulfonyl chloride, 52 g, 1.1 eq) and DMAP (4-dimethylamiopryidine, 2.5 g) in 500 mL CH$_2$Cl$_2$ at 0° C. was added Et$_3$N (51 g, 2.0 eq). After addition was completed, the reaction mixture was let warm to r.t. and stirred at that temperature overnight. The organic layer was washed with water and brine, dried with anhydrous Na$_2$SO$_4$, and purified by flash chromatography to give the product as a white solid (72 g, 88%). $^1$H NMR (400 MHz, CDCl$_3$) δ 7.80 (d, J=8.0 Hz, 2H), 7.34 (d, J=8.0 Hz, 2H), 4.46 (brs, 1H), 3.54-3.58 (m, 1H), 3.31-3.40 (m, 3H), 2.45 (s, 3H), 1.80-1.88 (m, 1H), 1.65-1.79 (m, 2H), 1.47-1.52 (m, 1H), 1.43 (s, 9H).

To a stirred solution of 5-amino-3-(4-phenoxyphenyl)-1H-pyrazole-4-carbonitrile (2.55 g, 1.0 eq) and tert-butyl 3-(tosyloxy)piperidine-1-carboxylate (3.93 g, 1.2 eq) in 30 mL dry DMF at r.t. was added Cs$_2$CO$_3$ (6.01 g, 2.0 eq). After addition was completed, the reaction mixture was heated to 80° C. and stirred at that temperature for 50 h. Water was added and the mixture was extracted with EtOAc. The organic extract was washed with water and brine, dried with anhydrous Na$_2$SO$_4$, and purified by flash chromatography to give compound 7 as a white solid (0.67 g, 16%). $^1$H NMR (400 MHz, CDCl$_3$) δ 7.87 (d, J=8.8 Hz, 2H), 7.35 (d, J=8.4 Hz, 2H), 7.13 (t, J=7.6 Hz, 1H), 7.03-7.06 (m, 4H), 4.42 (s, 2H), 4.16-4.25 (m, 1H), 4.04-4.16 (m, 1H), 3.80-3.91 (m, 1H), 3.03-3.21 (m, 1H), 2.81 (t, J=12.4 Hz, 1H), 2.17-2.31 (m, 1H), 2.07-2.17 (m, 1H), 1.83-1.91 (m, 1H), 1.54-1.64 (m, 1H), 1.48 (s, 9H).

Step H: Tert-butyl 3-(5-(tert-butoxycarbonylamino)-4-cyano-3-(4-phenoxyphenyl)-1H-pyrazol-1-yl)piperidine-1-carboxylate

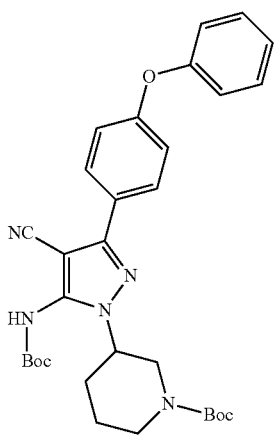 [SMILES: CC(C)(C)OC(=O)Nc1c(C#N)c(-c2ccc(Oc3ccccc3)cc2)nn1C1CCCN(C(=O)OC(C)(C)C)C1]

To a stirred solution of tert-butyl 3-(5-amino-4-cyano-3-(4-phenoxyphenyl)-1H-pyrazol-1-yl)piperidine-1-carboxylate (183 mg, 1.0 eq), Et$_3$N (81 mg, 2.0 eq) and DMAP (20 mg) in 30 mL dry THF at 0° C. was added (Boc)$_2$O (105 mg, 1.2 eq). After addition was completed, the reaction mixture was let warm to r.t. and stirred at that temperature overnight. Water was added. The organic layer was separated, washed with water and brine, dried with anhydrous Na$_2$SO$_4$, and purified by flash chromatography to give the product as a white solid (213 mg, 95%). $^1$H NMR (400 MHz, CDCl$_3$) δ 7.90 (d, J=8.8 Hz, 2H), 7.36 (t, J=8.4 Hz, 2H), 7.14 (t, J=7.6 Hz, 1H), 7.04-7.07 (m, 4H), 6.25-6.60 (brs, 1H), 4.24 (d, J=12.8 Hz, 1H), 4.09-4.15 (m, 2H), 3.21-3.28 (m, 1H), 2.74-2.86 (m, 1H), 2.11-2.20 (m, 2H), 1.86-1.89 (m, 1H), 1.54 (s, 9H), 1.45-1.49 (m, 10H).

Step I: Tert-butyl 3-(5-(tert-butoxycarbonyl(methyl)amino)-4-cyano-3-(4-phenoxyphenyl)-1H-pyrazol-1-yl)piperidine-1-carboxylate

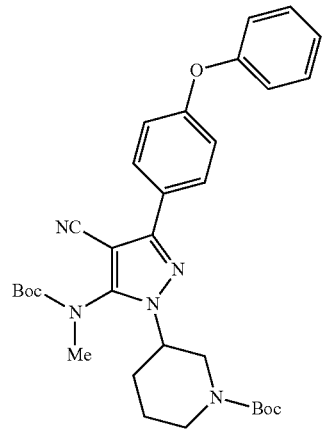 [SMILES: CN(C(=O)OC(C)(C)C)c1c(C#N)c(-c2ccc(Oc3ccccc3)cc2)nn1C1CCCN(C(=O)OC(C)(C)C)C1]

To a stirred solution of tert-butyl 3-(5-(tert-butoxycarbonylamino)-4-cyano-3-(4-phenoxyphenyl)-1H-pyrazol-1-yl)piperidine-1-carboxylate (84 mg, 1.0 eq) in 2 mL dry DMF at 0° C. was added NaH (7.2 mg, 1.2 eq). The mixture was let warm up to room temperature and stirred at r.t. for 20 min. CH$_3$I (22 mg, 1.0 eq) was added slowly at room temperature. After addition was completed, the reaction mixture was heated to 60° C. and stirred at that temperature for 1 h. Water was added, and the mixture was extracted with CH$_2$Cl$_2$. The organic extract was washed with water and brine, dried with anhydrous Na$_2$SO$_4$, and purified by flash chromatography to give the product as a white solid (60 mg, 65%). $^1$H NMR (400 MHz, CDCl$_3$) δ 7.93 (d, J=8.0 Hz, 2H), 7.37 (t, J=8.0 Hz, 2H), 7.14 (t, J=7.6 Hz, 1H), 7.07 (d, J=8.8 Hz, 2H), 7.05 (d, J=8.8 Hz, 2H), 4.09-4.14 (m, 2H), 3.90-4.07 (m, 1H), 3.19-3.31 (m, 4H), 2.69-2.87 (m, 1H), 1.82-2.29 (m, 3H), 1.55-1.65 (m, 1H), 1.46 (s, 9H).

Step J: Tert-butyl 3-(5-(tert-butoxycarbonyl(methyl)amino)-4-carbamoyl-3-(4-phenoxyphenyl)-1H-pyrazol-1-yl)piperidine-1-carboxylate

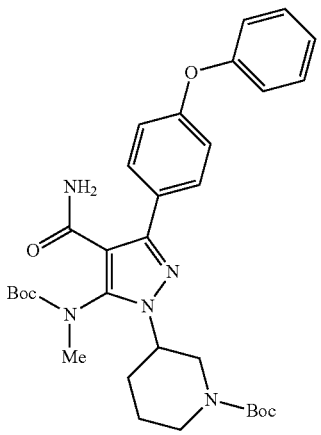 [SMILES: CN(C(=O)OC(C)(C)C)c1c(C(N)=O)c(-c2ccc(Oc3ccccc3)cc2)nn1C1CCCN(C(=O)OC(C)(C)C)C1]

To a stirred solution of tert-butyl 3-(5-(tert-butoxycarbonyl(methyl)amino)-4-cyano-3-(4-phenoxyphenyl)-1H-pyrazol-1-yl)piperidine-1-carboxylate (60 mg, 1.0 eq) and $K_2CO_3$ (44 mg, 3.0 eq) in 4 mL DMSO at r.t. was added $H_2O_2$ (4 mL, 30%) very slowly. After addition was completed, the reaction mixture was heated to 60° C. and stirred at that temperature for 1 h. Water was added and the mixture was extracted with $CH_2Cl_2$. The organic extract was washed with water and brine, dried with anhydrous $Na_2SO_4$, and purified by flash chromatography to give the product as a white solid (11 mg). $^1$H NMR (400 MHz, CDCl$_3$) δ 7.63 (d, J=8.4 Hz, 2H), 7.38 (t, J=7.6 Hz, 2H), 7.15 (t, J=7.6 Hz, 1H), 7.05-7.08 (m, 4H), 5.52 (s, 2H), 3.95-4.40 (m, 3H), 3.15-3.33 (m, 4H), 2.65-2.84 (m, 1H), 2.13-2.25 (m, 1H), 1.96-2.07 (m, 1H), 1.86 (d, J=13.6 Hz, 1H), 1.60-1.66 (m, 1H), 1.48 (s, 9H), 1.46 (s, 9H).

Step K: 1-(1-acryloylpiperidin-3-yl)-5-(methylamino)-3-(4-phenoxy-phenyl)-1H-pyrazole-4-carboxamide

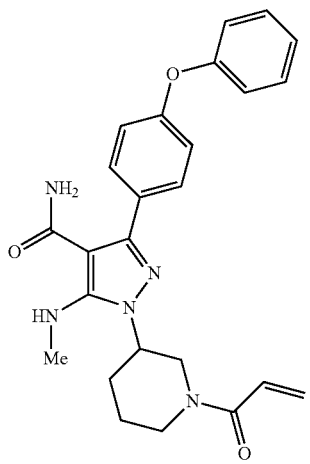 [SMILES: C=CC(=O)N1CCCC(n2nc(-c3ccc(Oc4ccccc4)cc3)c(C(N)=O)c2NC)C1]

To a stirred solution of tert-butyl 3-(5-(tert-butoxycarbonyl(methyl)amino)-4-carbamoyl-3-(4-phenoxyphenyl)-1H-pyrazol-1-yl)piperidine-1-carboxylate (11 mg, 1.0 eq) in 20 mL 1,4-dioxane at r.t. was added 4N HCl in 1,4-dioxane (1 mL). After addition was completed, the reaction was stirred at r.t. overnight. Concentrated to dryness to give the crude product, no further purification needed. This crude product was dissolved in 5 mL $CH_2Cl_2$ and DIEA (10 mg, 5.0 eq) was added 0° C., After addition was completed, acryloyl chloride (4 mg, 1.0 eq) was added slowly. After addition was completed, the reaction mixture was stirred at 0° C. for 5 min. Water was added and the mixture was extracted with $CH_2Cl_2$. The organic extract was washed with water and brine, dried with anhydrous $Na_2SO_4$, and purified by flash chromatography to give the product as a white solid (8 mg). $^1$H NMR (400 MHz, CDCl$_3$) δ 7.49 (d, J=8.4 Hz, 2H), 7.37 (t, J=8.0 Hz, 2H), 7.16 (t, J=7.6 Hz, 1H), 7.07 (d, J=8.4 Hz, 2H), 7.05 (d, J=8.4 Hz, 2H), 6.55-6.65 (m, 2H), 6.28-6.35 (m, 1H), 5.71-5.74 (m, 1H), 5.13-5.43 (brs, 2H), 4.92 and 4.67 (d, J=11.6 Hz, 1H), 3.99-4.24 (m, 2H), 3.64 and 3.20 (t, J=12.0 Hz and J=11.6 Hz, 1H), 3.08 and 2.69 (t, J=12.4 and J=10.8 Hz, 1H), 3.03 and 2.95 (d, J=1.2 Hz and J=1.2 Hz 1H), 2.28-2.43 (m, 1H), 2.12-2.25 (m, 1H), 1.94 (d, J=13.6 Hz, 1H), 1.55-1.66 (m, 1H). m/z=446[M+1]$^+$.

Example 2

(R)-1-(1-acryloylpiperidin-3-yl)-5-(methylamino)-3-(4-phenoxyphenyl)-1H-pyrazole-4-carboxamide

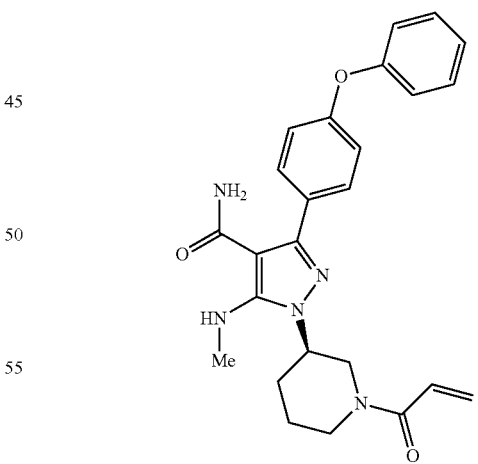

The synthesis of Example 2 was accomplished using a procedure analogous to that described in Example 1 with (S)-tert-butyl 3-(tosyloxy)piperidine-1-carboxylate. m/z=446[M+1]$^+$.

Example 3

1-(1-acryloylpyrrolidin-3-yl)-5-(methylamino)-3-(4-phenoxyphenyl)-1H-pyrazole-4-carboxamide

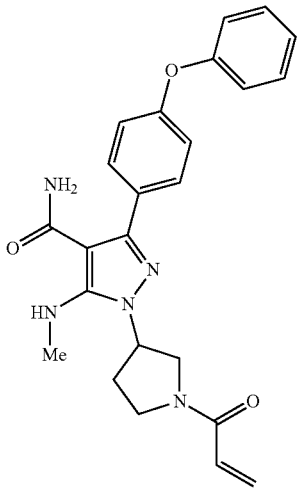 [SMILES: C=CC(=O)N1CCC(n2nc(-c3ccc(Oc4ccccc4)cc3)c(C(N)=O)c2NC)C1]

The synthesis of Example 3 was accomplished using a procedure analogous to that described in Example 1 with tert-butyl 3-(tosyloxy)pyrrolidine-1-carboxylate. $^1$H NMR (400 MHz, CDCl$_3$) δ 7.46 (d, J=8.4 Hz, 2H), 7.38 (t, J=8.4 Hz, 2H), 7.15 (t, J=7.6 Hz, 1H), 7.06 (d, J=8.4 Hz, 2H), 7.01 (d, J=8.4 Hz, 2H), 6.38-6.51 (m, 3H), 5.65-5.71 (m, 1H), 5.36-5.42 (brs, 2H), 4.98 and 5.02 (d, J=11.2 Hz, 1H), 3.94-4.28 (m, 2H), 3.54 and 3.25 (t, J=11.2 Hz and J=11.6 Hz, 1H), 3.18 and 2.59 (t, J=12.4 and J=10.8 Hz, 1H), 3.06 and 2.85 (d, J=1.2 Hz and J=1.2 Hz, 1H), 1.85 (d, J=11.6 Hz, 1H), 1.45-1.67 (m, 1H). m/z=432[M+1]$^+$.

Example 4

1-(2-(N-methylacrylamido)ethyl)-5-(methylamino)-3-(4-phenoxyphenyl)-1H-pyrazole-4-carboxamide

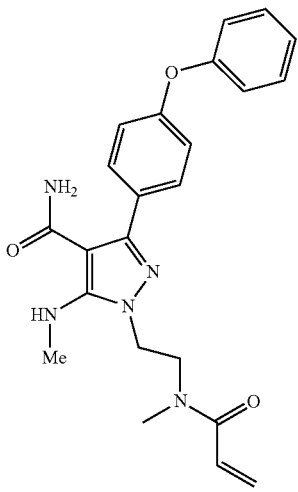 [SMILES: C=CC(=O)N(C)CCn1nc(-c2ccc(Oc3ccccc3)cc2)c(C(N)=O)c1NC]

The synthesis of Example 4 was accomplished using a procedure analogous to that described in Example 1 with tert-butyl 2-chloroethyl(methyl)carbamate. m/z=420[M+1]$^+$.

Example 5

1-(2-acrylamidoethyl)-5-(methylamino)-3-(4-phenoxyphenyl)-1H-pyrazole-4-carboxamide

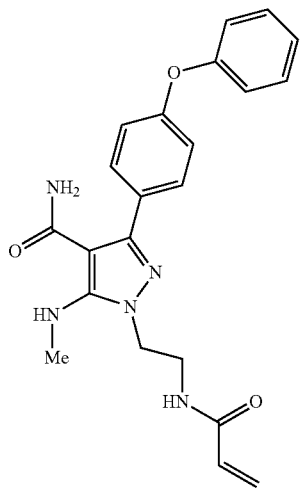 [SMILES: C=CC(=O)NCCn1nc(-c2ccc(Oc3ccccc3)cc2)c(C(N)=O)c1NC]

The synthesis of Example 5 was accomplished using a procedure analogous to that described in Example 1 with tert-butyl 2-chloroethylcarbamate. m/z=406[M+1]$^+$.

Example 6

1-(1-acryloylpiperidin-3-yl)-5-(ethylamino)-3-(4-phenoxyphenyl)-1H-pyrazole-4-carboxamide

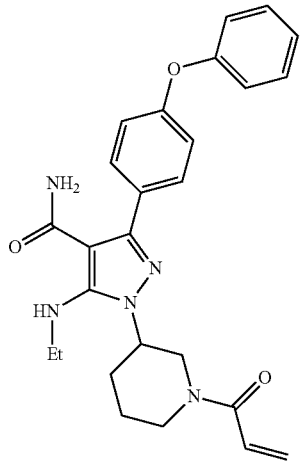 [SMILES: C=CC(=O)N1CCCC(n2nc(-c3ccc(Oc4ccccc4)cc3)c(C(N)=O)c2NCC)C1]

The synthesis of Example 6 was accomplished using a procedure analogous to that described in Example 1 with EtI. $^1$H NMR (400 MHz, CDCl$_3$) δ 7.50 (d, J=8.4 Hz, 2H), 7.39 (t, J=8.0 Hz, 2H), 7.18 (t, J=7.6 Hz, 1H), 7.08 (d, J=8.4 Hz, 2H), 7.04 (d, J=8.4 Hz, 2H), 6.56-6.69 (m, 2H), 6.24-

6.39 (m, 1H), 5.70-5.78 (m, 1H), 5.10-5.44 (brs, 2H), 4.88 and 4.59 (d, J=11.6 Hz, 1H), 3.97-4.22 (m, 2H), 3.62 and 3.21 (t, J=12.0 Hz and J=11.6 Hz, 1H), 3.45 (q, J=8.2 Hz, 2H), 3.05 and 2.65 (t, J=12.4 and J=10.8 Hz, 1H), 3.03 and 2.95 (d, J=1.2 Hz and J=1.2 Hz 1H), 2.26-2.46 (m, 1H), 2.10-2.28 (m, 1H), 1.92 (d, J=13.6 Hz, 1H), 1.54-1.68 (m, 1H). m/z=460[M+1]$^+$.

Example 7

1-(1-acryloylpiperidin-3-yl)-5-(isopropylamino)-3-(4-phenoxyphenyl)-1H-pyrazole-4-carboxamide

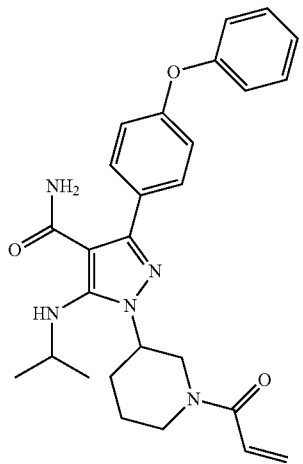 [SMILES: C=CC(=O)N1CCCC(n2nc(-c3ccc(Oc4ccccc4)cc3)c(C(N)=O)c2NC(C)C)C1]

The synthesis of Example 7 was accomplished using a procedure analogous to that described in Example 1 with 2-bromopropane. m/z=474[M+1]$^+$.

Example 8

1-(1-acryloylpiperidin-3-yl)-5-(cyclopropylamino)-3-(4-phenoxyphenyl)-1H-pyrazole-4-carboxamide

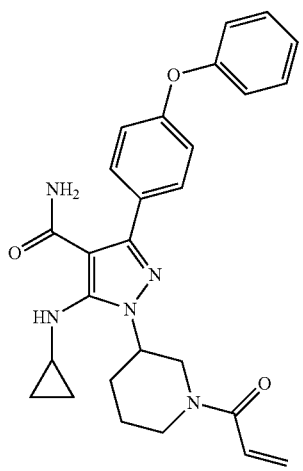 [SMILES: C=CC(=O)N1CCCC(n2nc(-c3ccc(Oc4ccccc4)cc3)c(C(N)=O)c2NC2CC2)C1]

The synthesis of Example 8 was accomplished using a procedure analogous to that described in Example 1 with cyclopropyl 4-methylbenzenesulfonate. m/z=472[M+1]$^+$.

Example 9

1-(1-acryloylpiperidin-3-yl)-5-(2-methoxyethylamino)-3-(4-phenoxyphenyl)-1H-pyrazole-4-carboxamide

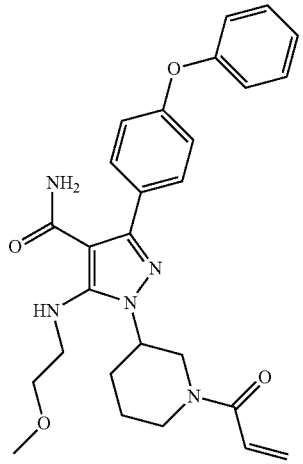 [SMILES: C=CC(=O)N1CCCC(n2nc(-c3ccc(Oc4ccccc4)cc3)c(C(N)=O)c2NCCOC)C1]

The synthesis of Example 9 was accomplished using a procedure analogous to that described in Example 1 with 1-bromo-2-methoxyethane. $^1$H NMR (400 MHz, CDCl$_3$) δ 7.50 (d, J=8.4 Hz, 2H), 7.39 (t, J=8.0 Hz, 2H), 7.18 (t, J=7.6 Hz, 1H), 7.08 (d, J=8.4 Hz, 2H), 7.04 (d, J=8.4 Hz, 2H), 6.52-6.67 (m, 2H), 6.38-6.46 (m, 1H), 6.29-6.39 (m, 1H), 6.06-6.16 (m, 1H), 5.80-5.88 (m, 1H), 5.68-5.76 (m, 2H), 4.60-4.90 (m, 1H), 4.36-4.46 (m, 4H), 4.01-4.50 (m, 2H), 3.28-3.61 (m, 5H), 2.62-2.78 (m, 6H). m/z=490[M+1]$^+$.

Example 10

1-(1-acryloylpiperidin-3-yl)-5-(2-aminoethylamino)-3-(4-phenoxyphenyl)-1H-pyrazole-4-carboxamide

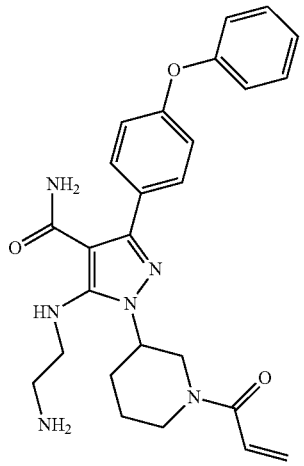 [SMILES: C=CC(=O)N1CCCC(n2nc(-c3ccc(Oc4ccccc4)cc3)c(C(N)=O)c2NCCN)C1]

The synthesis of Example 10 was accomplished using a procedure analogous to that described in Example 1 with tert-butyl 2-chloroethylcarbamate. m/z=475[M+1]$^+$.

Example 11

1-(1-acryloylpiperidin-3-yl)-5-(2-(methylamino)ethylamino)-3-(4-phenoxy-phenyl)-1H-pyrazole-4-carboxamide

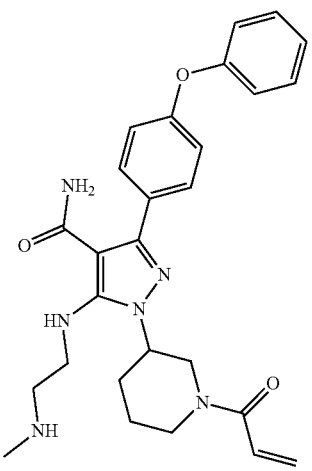

The synthesis of Example 11 was accomplished using a procedure analogous to that described in Example 1 with tert-butyl 2-chloroethyl(methyl)carbamate. m/z=489[M+1]$^+$.

Example 12

1-(1-acryloylpiperidin-3-yl)-5-(2-(dimethylamino)ethylamino)-3-(4-phenoxy-phenyl)-1H-pyrazole-4-carboxamide

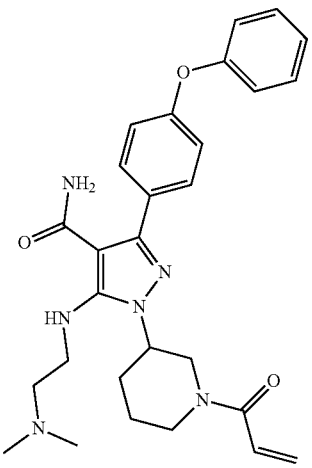 [SMILES: C=CC(=O)N1CCCC(n2nc(-c3ccc(Oc4ccccc4)cc3)c(C(N)=O)c2NCCN(C)C)C1]

The synthesis of Example 12 was accomplished using a procedure analogous to that described in Example 1 with 2-chloro-N,N-dimethylethanamine. m/z=503[M+1]$^+$.

Example 13

1-(1-acryloylpiperidin-3-yl)-5-(2-morpholinoethylamino)-3-(4-phenoxy-phenyl)-1H-pyrazole-4-carboxamide

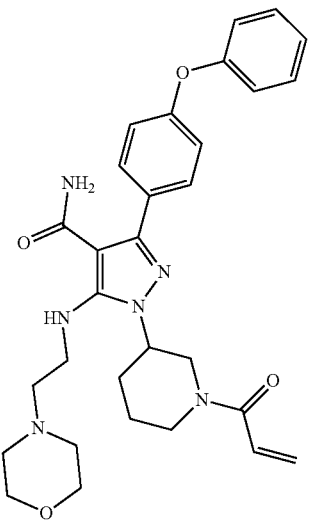 [SMILES: C=CC(=O)N1CCCC(n2nc(-c3ccc(Oc4ccccc4)cc3)c(C(N)=O)c2NCCN2CCOCC2)C1]

The synthesis of Example 13 was accomplished using a procedure analogous to that described in Example 1 with 4-(2-chloroethyl)morpholine. m/z=545[M+1]$^+$.

Example 14

1-(1-acryloylpiperidin-3-yl)-3-(4-phenoxyphenyl)-5-(2-(piperazin-1-yl)ethylamino)-1H-pyrazole-4-carboxamide

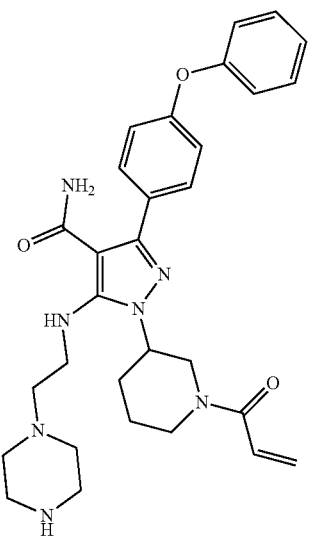 [SMILES: C=CC(=O)N1CCCC(n2nc(-c3ccc(Oc4ccccc4)cc3)c(C(N)=O)c2NCCN2CCNCC2)C1]

The synthesis of Example 14 was accomplished using a procedure analogous to that described in Example 1 with tert-butyl 4-(2-chloroethyl)piperazine-1-carboxylate. m/z=544[M+1]$^+$.

Example 15

1-(1-acryloylpiperidin-3-yl)-5-(2-(4-methylpiperazin-1-yl)ethylamino)-3-(4-phenoxy-phenyl)-1H-pyrazole-4-carboxamide

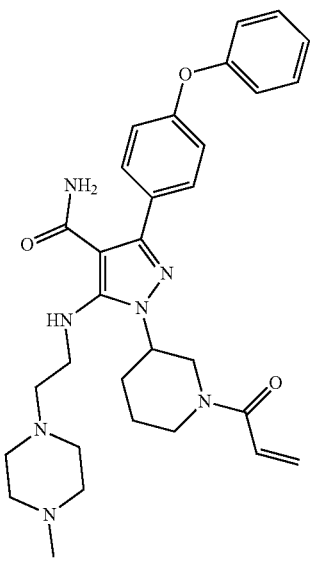 [SMILES: C=CC(=O)N1CCCC(n2nc(-c3ccc(Oc4ccccc4)cc3)c(C(N)=O)c2NCCN2CCN(C)CC2)C1]

The synthesis of Example 15 was accomplished using a procedure analogous to that described in Example 1 with 1-(2-chloroethyl)-4-methylpiperazine. m/z=558[M+1]⁺.

Example 16

1-(1-acryloylpiperidin-3-yl)-5-(2,3-dihydroxypropylamino)-3-(4-phenoxy-phenyl)-1H-pyrazole-4-carboxamide

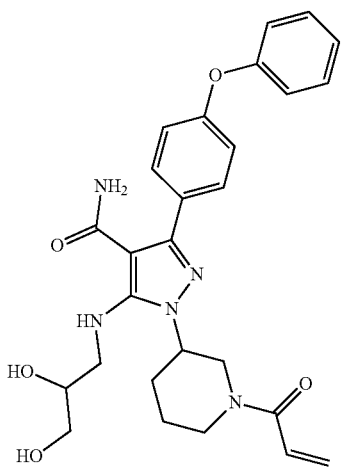 [SMILES: C=CC(=O)N1CCCC(n2nc(-c3ccc(Oc4ccccc4)cc3)c(C(N)=O)c2NCC(O)CO)C1]

The synthesis of Example 16 was accomplished using a procedure analogous to that described in Example 1 with 3-bromoprop-1-ene. m/z=506[M+1]⁺.

Example 17

5-acetamido-1-(1-acryloylpiperidin-3-yl)-3-(4-phenoxyphenyl)-1H-pyrazole-4-carboxamide

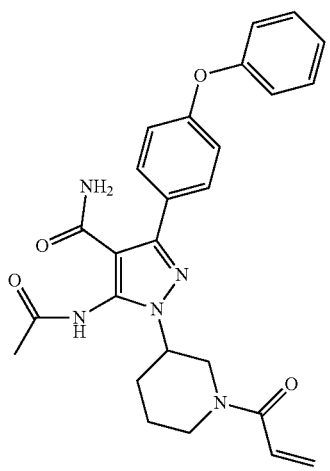 [SMILES: C=CC(=O)N1CCCC(n2nc(-c3ccc(Oc4ccccc4)cc3)c(C(N)=O)c2NC(C)=O)C1]

The synthesis of Example 17 was accomplished using a procedure analogous to that described in Example 1 with acetyl chloride. m/z=474[M+1]⁺.

Example 18

(R)-1-(1-acryloylpiperidin-3-yl)-5-amino-3-(4-phenoxyphenyl)-1H-pyrazole-4-carboxamide

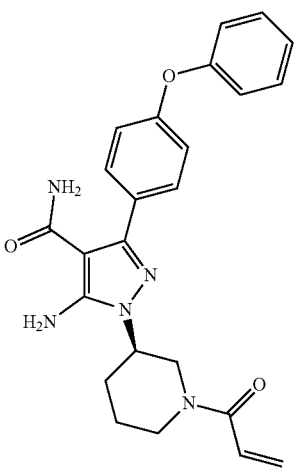 [SMILES: C=CC(=O)N1CCC[C@@H](n2nc(-c3ccc(Oc4ccccc4)cc3)c(C(N)=O)c2N)C1]

Scheme 2
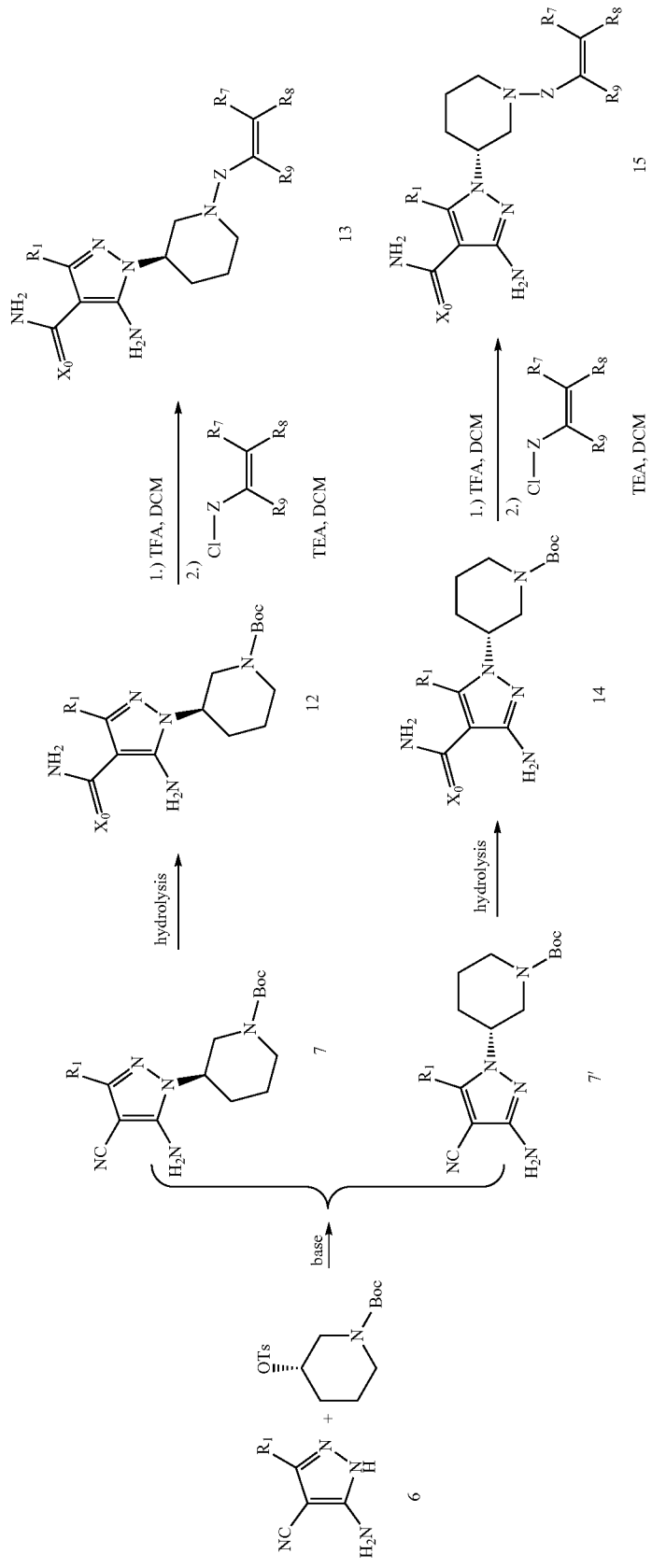

Step A: (R)-tert-butyl 3-(5-amino-4-cyano-3-(4-phenoxyphenyl)-1H-pyrazol-1-yl)piperidine-1-carboxylate

Step B: (R)-tert-butyl 3-(5-amino-4-carbamoyl-3-(4-phenoxyphenyl)-1H-pyrazol-1-yl)piperidine-1-carboxylate

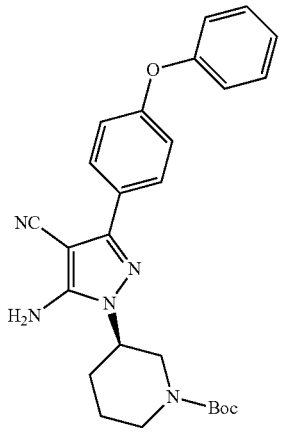 [SMILES: CC(C)(C)OC(=O)N1CCC[C@@H](n2nc(-c3ccc(Oc4ccccc4)cc3)c(C#N)c2N)C1]

(S)-tert-butyl 3-(tosyloxy)piperidine-1-carboxylate

To a stirred solution of (S)-tert-butyl 3-hydroxypiperidine-1-carboxylate (50 g, 1.0 eq), TsCl (4-methylbenzene-1-sulfonyl chloride, 52 g, 1.1 eq) and DMAP (4-dimethylamiopryidine, 2.5 g) in 500 mL $CH_2Cl_2$ at 0° C. was added $Et_3N$ (51 g, 2.0 eq). After addition was completed, the reaction mixture was warmed to r.t. and stirred at that temperature for 40 hours. The organic layer was washed with water and brine, dried with anhydrous $Na_2SO_4$, and purified by flash chromatography to give the product as a white solid (80 g, 91%). $^1H$ NMR (400 MHz, $CDCl_3$) δ 7.80 (d, J=8.0 Hz, 2H), 7.34 (d, J=8.0 Hz, 2H), 4.46 (brs, 1H), 3.54-3.58 (m, 1H), 3.31-3.40 (m, 3H), 2.45 (s, 3H), 1.80-1.88 (m, 1H), 1.65-1.79 (m, 2H), 1.47-1.52 (m, 1H), 1.43 (s, 9H).

To a stirred solution of 5-amino-3-(4-phenoxyphenyl)-1H-pyrazole-4-carbonitrile (20 g, 1.0 eq) and $Cs_2CO_3$ (70.7 g, 3.0 eq) in 300 mL dry DMF at 60° C. was added (S)-tert-butyl 3-(tosyloxy)piperidine-1-carboxylate (31 g, 1.2 eq) slowly. After addition was completed, the reaction mixture was stirred at 60° C. for 40 hours. Water was added and the mixture was extracted with EtOAc. The organic extract was washed with water and brine, dried with anhydrous $Na_2SO_4$, and purified by flash chromatography to give compound 7 as a white solid (8.8 g, 27%). $^1H$ NMR (400 MHz, $CDCl_3$) δ 7.85-7.88 (m, 2H), 7.33-7.37 (m, 2H), 7.09-7.14 (m, 1H), 7.03-7.06 (m, 4H), 4.52 (brs, 2H), 4.19-4.29 (m, 1H), 4.01-4.18 (m, 1H), 3.80-3.89 (m, 1H), 3.02-3.19 (m, 1H), 2.81 (t, J=12.8 Hz, 1H), 2.20-2.31 (m, 1H), 2.07-2.18 (m, 1H), 1.83-1.92 (m, 1H), 1.76-1.81 (m, 1H), 1.44 (s, 9H).

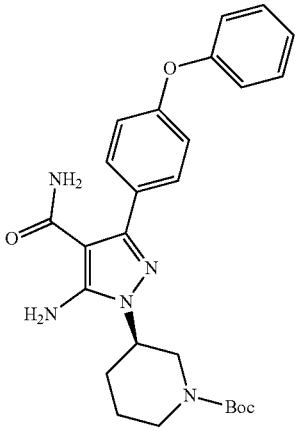 [SMILES: CC(C)(C)OC(=O)N1CCC[C@@H](n2nc(-c3ccc(Oc4ccccc4)cc3)c(C(N)=O)c2N)C1]

To a stirred solution of (R)-tert-butyl 3-(5-amino-4-cyano-3-(4-phenoxyphenyl)-1H-pyrazol-1-yl)piperidine-1-carboxylate (8.7 g, 1.0 eq) and $K_2CO_3$ (7.9 g, 3.0 eq) in 200 mL DMSO at 60° C. was added $H_2O_2$ (43 g, 30%, 20 eq) very slowly. After addition was completed, the reaction mixture was stirred at that temperature for 2 h. Water was added and the mixture was extracted with EtOAc. The organic extract was washed with water and brine, dried with anhydrous $Na_2SO_4$, and purified by flash chromatography to give the product as a white solid (7.5 g, 83%). $^1H$ NMR (400 MHz, $CDCl_3$) δ 7.48-7.52 (m, 2H), 7.35-7.39 (m, 2H), 7.13-7.17 (m, 1H), 7.04-7.08 (m, 4H), 5.54 (s, 2H), 5.19 (brs, 2H), 4.19-4.28 (m, 1H), 4.07-4.15 (m, 1H), 3.81-3.90 (m, 1H), 3.03-3.21 (m, 1H), 2.75 (t, J=11.6 Hz, 1H), 2.09-2.29 (m, 2H), 1.81-1.92 (m, 1H), 1.51-1.68 (m, 1H), 1.45 (s, 9H).

Step C: (R)-5-amino-3-(4-phenoxyphenyl)-1-(piperidin-3-yl)-1H-pyrazole-4-carboxamide Hydrochloride

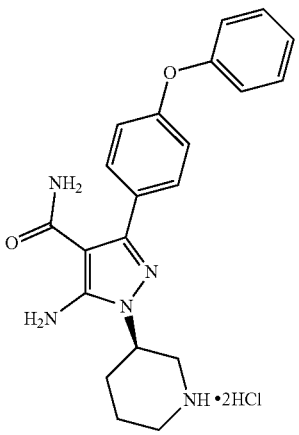 [SMILES: NC(=O)c1c(-c2ccc(Oc3ccccc3)cc2)nn([C@@H]2CCCNC2)c1N]

A stirred solution of (R)-tert-butyl 3-(5-amino-4-carbamoyl-3-(4-phenoxy-phenyl)-1H-pyrazol-1-yl)piperidine-1-carboxylate (8 g, 1.0 eq) in 700 mL ether/MeOH (5/2) at r.t.

was bubbled with HCl (g) for 5 h. The white solid was collected by filtration and dried to give the product as a white solid (6.8 g, 90%). $^1$H NMR (400 MHz, DMSO) δ 9.03 (s, 2H), 7.45-7.49 (m, 2H), 7.33-7.41 (m, 2H), 7.14 (t, J=7.2 Hz, 1H), 7.00-7.06 (m, 4H), 4.46 (s, 2H), 3.60 (brs, 2H), 3.11-3.59 (m, 4H), 2.80-2.98 (m, 1H), 1.71-2.02 (m, 4H). m/z=378[M+1]$^+$.

Step D: (R)-1-(1-acryloylpiperidin-3-yl)-5-amino-3-(4-phenoxyphenyl)-1H-pyrazole-4-carboxamide

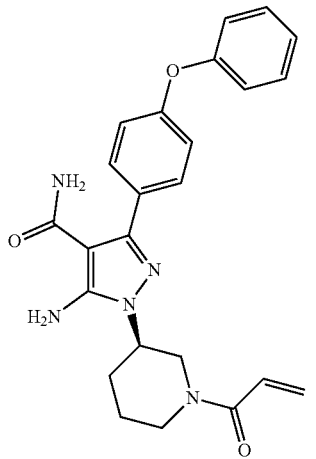 [SMILES: C=CC(=O)N1CCC[C@@H](n2nc(-c3ccc(Oc4ccccc4)cc3)c(C(N)=O)c2N)C1]

To a stirred solution of (R)-5-amino-3-(4-phenoxyphenyl)-1-(piperidin-3-yl)-1H-pyrazole-4-carboxamide (3.8 g, 1.0 eq) and DIEA (4.4 g, 4.0 eq) in 100 mL CH$_2$Cl$_2$ at −15° C. was added acryloyl chloride (802 mg, 1.05 eq) slowly. After addition was completed, the reaction was stirred at 0° C. for 5 min. Water was added and the mixture was extracted with CH$_2$Cl$_2$. The organic extract was washed with water and brine, dried with anhydrous Na$_2$SO$_4$, and purified by flash chromatography to give the product as a white solid (3.5 g, 96%). $^1$H NMR (400 MHz, CDCl$_3$) δ 7.49-7.52 (m, 2H), 7.35-7.39 (m, 2H), 7.14-7.18 (m, 1H), 7.04-7.09 (m, 4H), 6.58-6.62 (m, 1H), 6.35 (d, J=16.4 Hz, 1H), 5.70-5.77 (m, 2.5H), 5.48 (s, 0.5H), 5.20 (brs, 2H), 4.82 (d, J=12.8 Hz, 0.5H), 4.61-4.68 (m, 0.5H), 4.11-4.19 (m, 0.5H), 4.01 (d, J=12.8 Hz, 0.5H), 3.82-3.94 (m, 1H), 3.55-3.68 (m, 0.5H), 3.00-3.19 (m, 1H), 2.64-2.78 (m, 0.5H), 2.30-2.42 (m, 1H), 2.14-2.22 (m, 1H), 1.91-2.01 (m, 1H), 1.60-1.69 (m, 1H). m/z=432[M+1]$^+$.

Example 19

(R)-1-(1-acryloylpiperidin-3-yl)-3-amino-5-(4-phenoxyphenyl)-1H-pyrazole-4-carboxamide

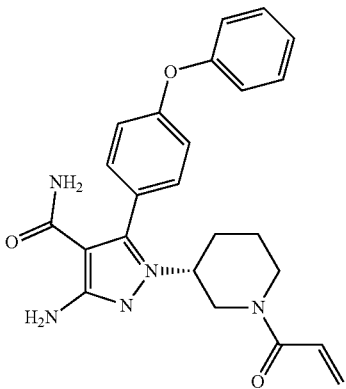

Scheme 3
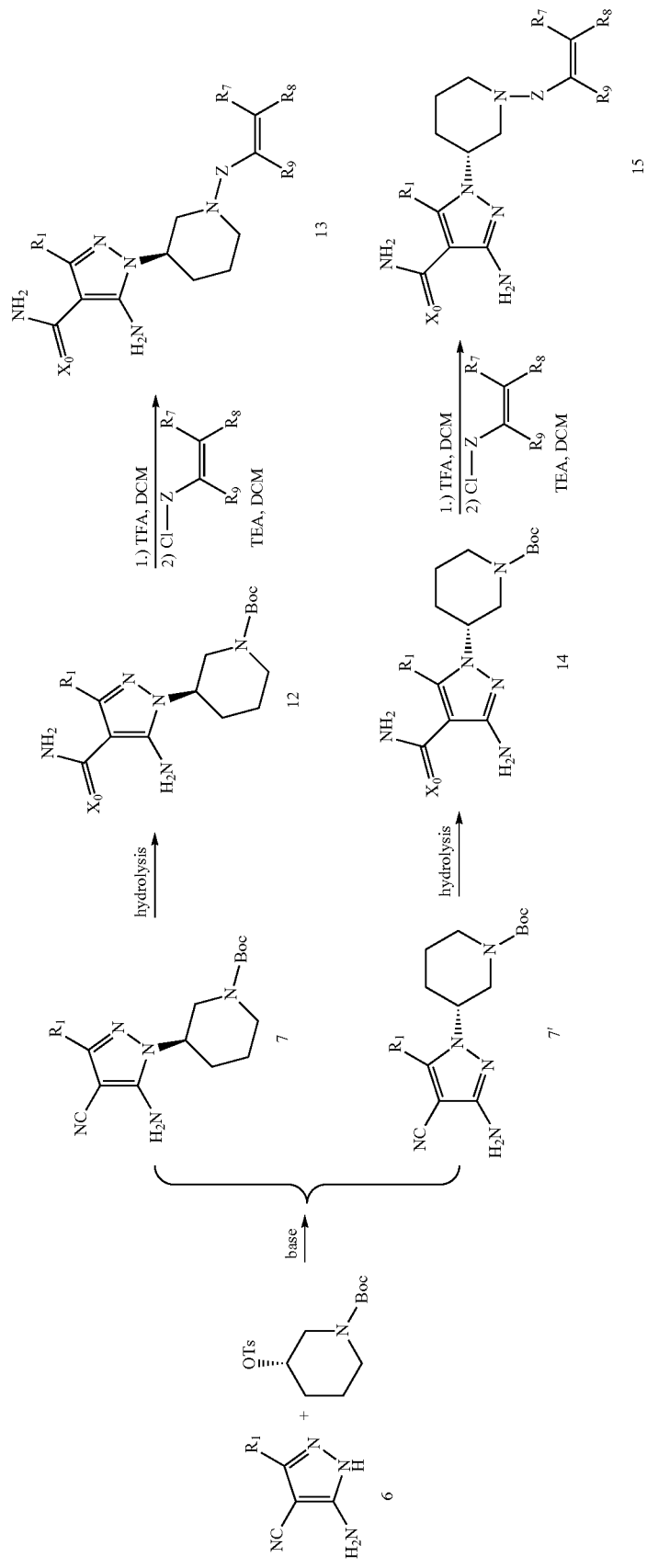

Step A: (R)-tert-butyl 3-(3-amino-4-cyano-5-(4-phenoxyphenyl)-1H-pyrazol-1-yl)piperidine-1-carboxylate

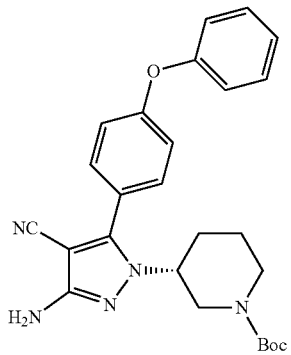 [SMILES: CC(C)(C)OC(=O)N1CCC[C@@H](n2nc(N)c(C#N)c2-c2ccc(Oc3ccccc3)cc2)C1]

To a stirred solution of 5-amino-3-(4-phenoxyphenyl)-1H-pyrazole-4-carbonitrile (0.5 g, 1.0 eq) and (S)-tert-butyl 3-(tosyloxy)piperidine-1-carboxylate (0.77 g, 1.2 eq) in 30 mL dry DMF at r.t. was added $Cs_2CO_3$ (1.18 g, 2.0 eq). After addition was completed, the reaction mixture was heated to 80° C. and stirred at that temperature for 5 h. Water was added and the mixture was extracted with EtOAc. The organic extract was washed with water and brine, dried with anhydrous $Na_2SO_4$, and purified by flash chromatography to give compound 7' as a light yellow solid (0.06 g, 8%). $^1$H NMR (400 MHz, $CDCl_3$) δ 7.39-7.42 (m, 4H), 7.18-7.22 (m, 1H), 7.09-7.12 (m, 4H), 3.97-4.10 (m, 5H), 3.17 (t, J=12.4 Hz, 1H), 2.69 (t, J=12.4 Hz, 1H), 2.14-2.18 (m, 1H), 1.90-1.98 (m, 1H), 1.72-1.81 (m, 1H), 1.51-1.59 (m, 1H), 1.41 (s, 9H).

Step B: (R)-tert-butyl 3-(3-amino-4-carbamoyl-5-(4-phenoxyphenyl)-1H-pyrazol-1-yl)piperidine-1-carboxylate

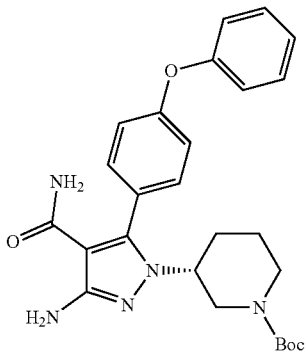 [SMILES: CC(C)(C)OC(=O)N1CCC[C@@H](n2nc(N)c(C(N)=O)c2-c2ccc(Oc3ccccc3)cc2)C1]

To a stirred solution of (R)-tert-butyl 3-(3-amino-4-cyano-5-(4-phenoxyphenyl)-1H-pyrazol-1-yl)piperidine-1-carboxylate (50 mg, 1.0 eq) and $K_2CO_3$ (45 mg, 3.0 eq) in 5 mL DMSO at r.t. was added $H_2O_2$ (2 mL). After addition was completed, the reaction was heated to 60° C. and stirred at that temperature for 5 h. Water was added and the mixture was extracted with $CH_2Cl_2$. The organic extract was washed with water and brine, dried with anhydrous $Na_2SO_4$, and purified by flash chromatography to give the product as a white solid (50 mg, 96%). $^1$H NMR (400 MHz, $CDCl_3$) δ 7.40-7.44 (m, 2H), 7.31-7.35 (m, 2H), 7.21-7.25 (m, 1H), 7.10-7.14 (m, 4H), 5.07 (s, 2H), 4.95 (s, 2H), 3.96-4.15 (m, 2H), 3.95-3.68 (m, 1H), 3.16 (t, J=12.4 Hz, 1H), 2.66 (t, J=12.4 Hz, 1H), 2.05-2.22 (m, 1H), 1.85-1.92 (m, 1H), 1.70-1.79 (m, 1H), 1.50-1.55 (m, 1H), 1.42 (s, 9H).

Step C: (R)-3-amino-5-(4-phenoxyphenyl)-1-(piperidin-3-yl)-1H-pyrazole-4-carboxamide

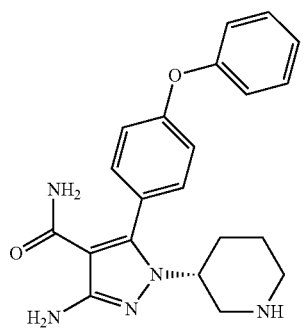 [SMILES: NC(=O)c1c(N)nn([C@@H]2CCCNC2)c1-c1ccc(Oc2ccccc2)cc1]

To a stirred solution of (R)-tert-butyl 3-(3-amino-4-carbamoyl-5-(4-phenoxyphenyl)-1H-pyrazol-1-yl)piperidine-1-carboxylate (50 mg, 1.0 eq) in 20 mL $CH_2Cl_2$ at r.t. was added TFA (Trifluoroaceticacid, 1 mL). After addition was completed, the reaction mixture was stirred at r.t. for 2 h. Water was added and the mixture was extracted with $CH_2Cl_2$. The organic extract was washed with water and brine, dried with anhydrous $Na_2SO_4$, and purified by flash chromatography to give the product as a white solid (20 mg, 51%). $^1$H NMR (400 MHz, $CDCl_3$) δ 7.41-7.45 (m, 2H), 7.29-7.32 (m, 2H), 7.21-7.25 (m, 1H), 7.10-7.14 (m, 4H), 5.10 (s, 2H), 4.95 (brs, 2H), 3.79-3.88 (m, 1H), 3.15-3.26 (m, 1H), 3.04-3.12 (m, 1H), 2.90-3.01 (m, 1H), 2.70-2.81 (m, 1H), 1.61-2.02 (m, 4H). m/z=378[M+1]$^+$.

Step D: (R)-1-(1-acryloylpiperidin-3-yl)-3-amino-5-(4-phenoxyphenyl)-1H-pyrazole-4-carboxamide

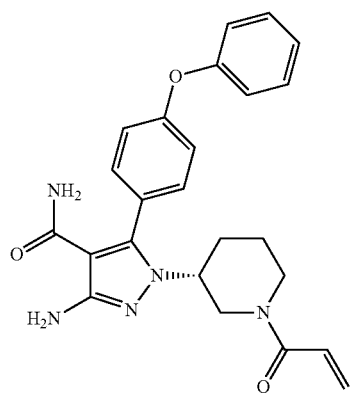 [SMILES: C=CC(=O)N1CCC[C@@H](n2nc(N)c(C(N)=O)c2-c2ccc(Oc3ccccc3)cc2)C1]

To a stirred solution of (R)-3-amino-5-(4-phenoxyphenyl)-1-(piperidin-3-yl)-1H-pyrazole-4-carboxamide (10 mg, 1.0 eq) and $Et_3N$ (11 mg, 4.0 eq) in 10 mL $CH_2Cl_2$ at 0° C. was added acryloyl chloride (2.5 mg, 1.05 eq) slowly. After addition was completed, the reaction was stirred at 0° C. for 5 min. Water was added and extracted with $CH_2Cl_2$, washed with water and brine, dried with anhydrous Na$_2$SO$_4$, and purified by flash chromatography to give the product as a white solid (3 mg, 26%). $^1$H NMR (400 MHz, CDCl$_3$) δ 7.20-7.46 (m, 5H), 7.10-7.19 (m, 4H), 6.45-6.59 (m, 0.5H), 6.10-6.38 (m, 1.5H), 5.56-5.70 (m, 1H), 5.09 (s, 2H), 5.02 (s, 2H), 4.70 (d, J=12.4 Hz, 0.5H), 4.62 (d, J=12.4 Hz, 0.5H), 3.81-3.98 (m, 1H), 3.59-3.75 (m, 1H), 3.42-3.57 (m, 0.5H), 3.00-3.19 (m, 1H), 2.58-2.68 (m, 0.5H), 2.19-2.31 (m, 1H), 1.90-2.01 (m, 1H), 1.80-1.89 (m, 1H), 1.60-1.65 (m, 1H). m/z=432[M+1]$^+$.

Example 20

5-amino-1-cyclohexyl-3-(4-phenoxyphenyl)-1H-pyrazole-4-carboxamide

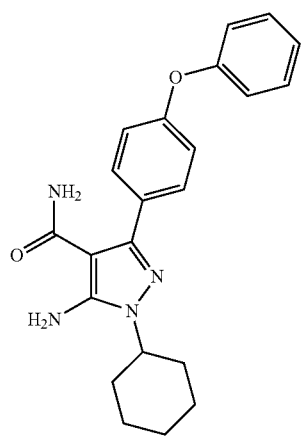 [SMILES: NC(=O)c1c(-c2ccc(Oc3ccccc3)cc2)nn(C2CCCCC2)c1N]

Scheme 4

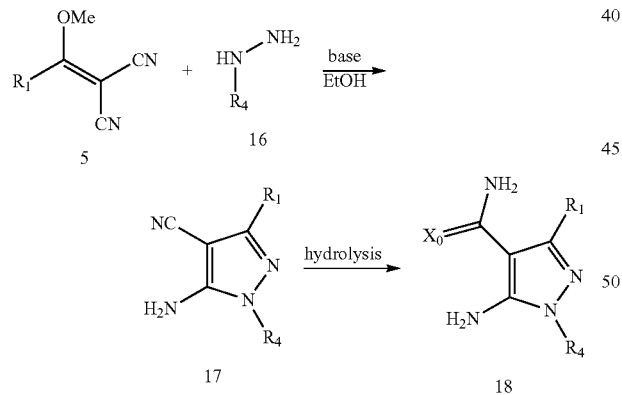

Step A: Tert-butyl 2-cyclohexylidenehydrazinecarboxylate

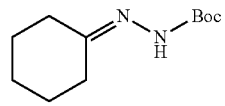

To a stirred solution of cyclohexanone (5.0 g, 1.0 eq) in 90 mL hexane was added tert-butyl hydrazinecarboxylate (8.7 g, 1.0 eq). After addition was completed, the reaction was stirred at 75° C. for 2 h. The mixture was cooled to 0° C. The solid was collected by filtration, washed with cool hexane (0° C.), and dried to give the product as a white solid (10.2 g, 95%). $^1$H NMR (400 MHz, CDCl$_3$) δ 7.47 (brs, 1H), 2.36 (t, J=6.8 Hz, 2H), 2.21 (t, J=6.8 Hz, 2H), 1.62-1.72 (m, 6H), 1.51 (s, 9H).

Step B: Tert-butyl 2-cyclohexylhydrazinecarboxylate

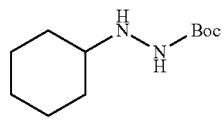 [SMILES: CC(C)(C)OC(=O)NNC1CCCCC1]

To a stirred solution of tert-butyl 2-cyclohexylidenehydrazinecarboxylate (5.6 g, 1.0 eq) in 100 mL MeOH was added Pd/C (0.6 g, 10%). After addition was completed, the reaction was stirred at 50° C. overnight under H$_2$ (10 atm) atmosphere. The mixture was filtered through a celite and the filtrate was concentrated to give the product (5.1 g, 92%) as a white solid. $^1$H NMR (400 MHz, CDCl$_3$) δ 6.05 (s, 1H), 3.89 (brs, 1H), 2.76-2.81 (m, 1H), 1.81-1.84 (m, 2H), 1.71-1.75 (m, 2H), 1.58-1.62 (m, 1H), 1.46 (s, 9H), 1.08-1.28 (5H, m).

Step C: Cyclohexylhydrazine Hydrochloride

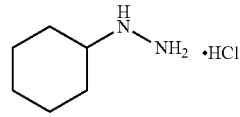

To a stirred solution of tert-butyl 2-cyclohexylhydrazinecarboxylate (2.7 g, 1.0 eq) in 40 mL ether was added HCl (5 mL, 12 N). After addition was completed, the reaction was stirred at r.t. for 3 h. The solvent was removed under reduced pressure. The residue was dissolved in 4 mL EtOH. With stirring 40 mL ether was added. The solid thus formed was collected by filtration, and dried to give the product as a white product (1.6 g, 85%). $^1$H NMR (400 MHz, CDCl$_3$) δ2.83-2.88 (m, 1H), 1.98-2.00 (m, 2H), 1.73-1.74 (m, 2H), 1.56-1.60 (m, 1H), 1.05-1.27 (m, 5H).

Step D: 5-amino-1-cyclohexyl-3-(4-phenoxyphenyl)-1H-pyrazole-4-carbonitrile

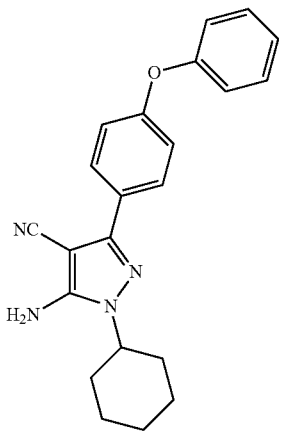 [SMILES: N#Cc1c(-c2ccc(Oc3ccccc3)cc2)nn(C2CCCCC2)c1N]

To a stirred solution of 2-(methoxy(4-phenoxyphenyl)methylene)malononitrile (225 mg, 1.0 eq) in 20 mL EtOH were added Et$_3$N (164.8 mg, 2.0 eq) and cyclohexylhydrazine hydrochloride (123 mg, 1.0 eq). After addition was completed, the reaction was stirred at 90° C. overnight. The mixture was diluted with water and extracted with EtOAc. The organic extract was washed with brine, dried and concentrated. The residue was purified with silica gel chromatography (petrol ether:EtOAc=5/1 to 3/1) to give the product (148 mg, 50%). 1HNMR (400 MHz, CDCl$_3$) δ7.89-7.91 (m, 2H), 7.34-7.38 (m, 2H), 7.12-7.15 (m, 1H), 7.04-7.07 (m, 4H), 4.22 (s, 2H), 3.79-3.83 (m, 1H), 1.95-2.00 (m, 5H), 1.74-1.78 (m, 1H), 1.28-1.44 (m, 4H). m/z=359[M+1]$^+$.

Step E: 5-amino-1-cyclohexyl-3-(4-phenoxyphenyl)-1H-pyrazole-4-carboxamide

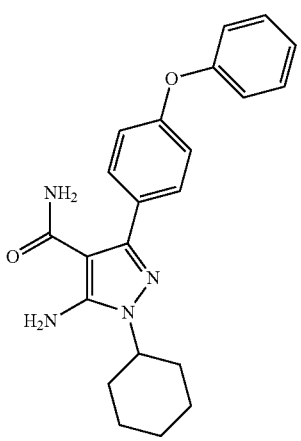 [SMILES: NC(=O)c1c(-c2ccc(Oc3ccccc3)cc2)nn(C2CCCCC2)c1N]

To a stirred solution of 5-amino-1-cyclohexyl-3-(4-phenoxyphenyl)-1H-pyrazole-4-carbonitrile (120 mg, 1.0 eq) in 10 mL DMSO was added K$_2$CO$_3$ (138 mg, 3.0 eq) and H$_2$O$_2$ (1 g). After addition was completed, the reaction was stirred at 60° C. for 1 h. The mixture was poured into water and filtrated to get a solid. The solid was dissolved in EtOAc and washed with brine, dried and concentrated. The residue was purified with silica gel chromatography (petrol ether:EtOAc=3/1 to 1/1) to give the product (91 mg, 72%) as a white solid. 1H NMR (400 MHz, CDCl$_3$) δ7.48-7.50 (m, 2H), 7.34 (t, J=7.6 Hz, 2H), 7.12 (t, J=7.2 Hz, 1H), 7.01-7.06 (m, 4H), 5.38 (s, 2H), 5.16 (brs, 2H), 3.76-3.82 (m, 1H), 1.88-2.02 (m, 5H), 1.67-1.71 (m, 1H), 1.22-1.40 (m, 4H). m/z=377[M+1]$^+$.

Example 21

5-amino-3-(4-phenoxyphenyl)-1-(piperidin-3-yl)-1H-pyrazole-4-carboxamide

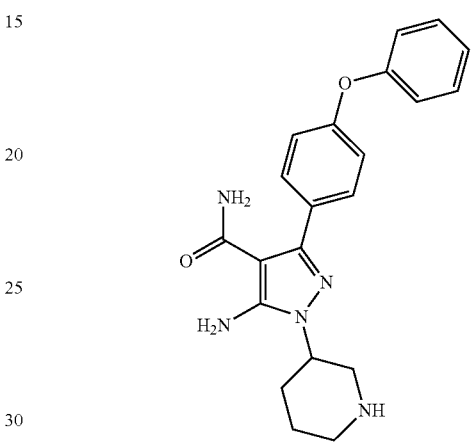

The synthesis of Example 21 was accomplished using a procedure analogous to that described in Example 20. $^1$H NMR (400 MHz, CDCl$_3$) δ 7.38-7.52 (m, 2H), 7.34-7.36 (m, 2H), 7.13-7.17 (m, 1H), 7.03-7.09 (m, 4H), 6.03 (s, 2H), 5.21 (brs, 2H), 4.01-4.07 (m, 1H), 3.20-3.22 (m, 2H), 2.90-3.01 (m, 1H), 2.74-2.84 (m, 1H), 2.12-2.26 (m, 1H), 1.95-2.08 (m, 1H), 1.80-1.90 (m, 1H), 1.60-1.65 (m, 1H). m/z=378 [M+1]$^+$.

Example 22

1-(1-acryloylpiperidin-3-yl)-5-amino-3-(4-phenoxyphenyl)-1H-pyrazole-4-carboxamide

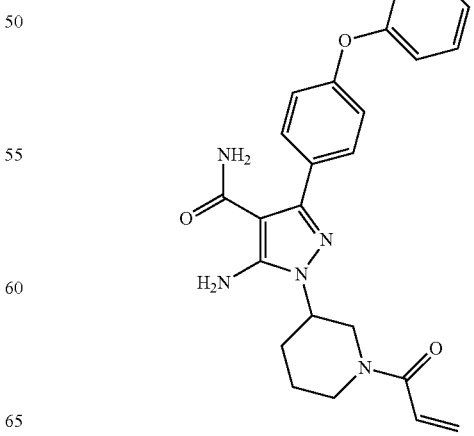

The synthesis of Example 22 was accomplished using a procedure analogous to that described in Example 20. ¹H NMR (400 MHz, CDCl₃) δ 7.48-7.54 (m, 2H), 7.32-7.40 (m, 2H), 7.10-7.19 (m, 1H), 7.01-7.09 (m, 4H), 6.52-6.68 (m, 1H), 6.34 (d, J=16.4 Hz, 1H), 5.60-5.79 (m, 2.5H), 5.57 (s, 0.5H), 5.25 (brs, 2H), 4.82 (d, J=11.6 Hz, 0.5H), 4.60-4.68 (m, 0.5H), 4.08-4.20 (m, 0.5H), 4.02 (d, J=14.0 Hz, 0.5H), 3.89-3.94 (m, 1H), 3.54-3.66 (m, 0.5H), 2.99-3.20 (m, 1H), 2.63-2.76 (m, 0.5H), 2.22-2.40 (m, 1H), 2.10-2.21 (m, 1H), 1.91-1.99 (m, 1H), 1.52-1.68 (m, 1H). m/z=432[M+1]⁺.

Example 23

(S)-1-(1-acryloylpiperidin-3-yl)-5-amino-3-(4-phenoxyphenyl)-1H-pyrazole-4-carboxamide

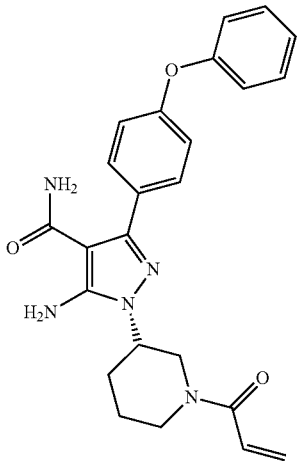

The synthesis of Example 23 was accomplished using a procedure analogous to that described in Example 18 with (R)-tert-butyl 3-(tosyloxy)piperidine-1-carboxylate. ¹H NMR (400 MHz, CDCl₃) δ 7.49-7.54 (m, 2H), 7.32-7.42 (m, 2H), 7.11-7.20 (m, 1H), 7.01-7.10 (m, 4H), 6.58-6.64 (m, 1H), 6.34 (d, J=16.4 Hz, 1H), 5.61-5.79 (m, 2.5H), 5.55 (s, 0.5H), 5.27 (brs, 2H), 4.83 (d, J=12.8 Hz, 0.5H), 4.66 (d, J=12.8 Hz, 0.5H), 4.16 (d, J=14.8 Hz, 0.5H), 4.02 (d, J=13.6 Hz, 0.5H), 3.86-3.95 (m, 1H), 3.56-3.69 (m, 0.5H), 2.98-3.18 (m, 1H), 2.62-2.77 (m, 0.5H), 2.28-2.40 (m, 1H), 2.12-2.23 (m, 1H), 1.90-2.00 (m, 1H), 1.70-1.80 (m, 1H). m/z=432[M+1]⁺.

Example 24

1-(1-acryloylpiperidin-4-yl)-5-amino-3-(4-phenoxyphenyl)-1H-pyrazole-4-carboxamide

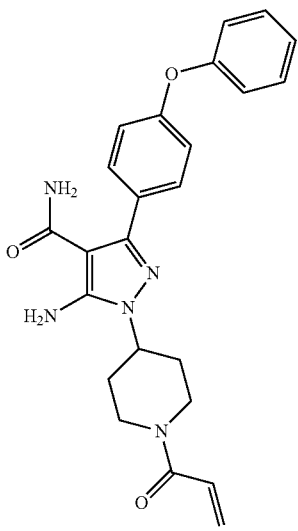 [SMILES: C=CC(=O)N1CCC(n2nc(-c3ccc(Oc4ccccc4)cc3)c(C(N)=O)c2N)CC1]

The synthesis of Example 24 was accomplished using a procedure analogous to that described in Example 18 with tert-butyl 4-(tosyloxy)piperidine-1-carboxylate. ¹H NMR (400 MHz, CDCl₃) δ 7.48-7.54 (m, 2H), 7.34-7.39 (m, 2H), 7.13-7.18 (m, 1H), 7.03-7.08 (m, 4H), 6.54-6.61 (m, 1H), 6.57 (d, J=14.8 Hz, 1H), 5.69 (d, J=8.8 Hz, 1H), 5.46 (s, 2H), 5.22 (brs, 2H), 4.71-4.82 (m, 1H), 4.07-4.22 (m, 2H), 3.19-3.24 (m, 1H), 2.80-2.91 (m, 1H), 2.10-2.31 (m, 2H), 1.99-2.07 (m, 2H). m/z=432[M+1]⁺.

Example 25

1-(1-acryloylpyrrolidin-3-yl)-5-amino-3-(4-phenoxyphenyl)-1H-pyrazole-4-carboxamide

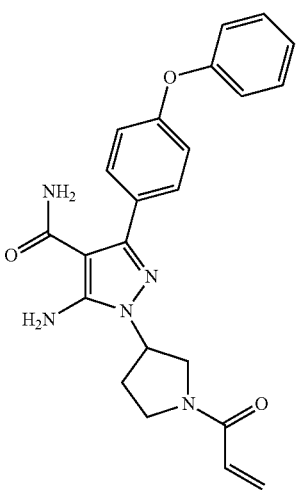 [SMILES: C=CC(=O)N1CCC(n2nc(-c3ccc(Oc4ccccc4)cc3)c(C(N)=O)c2N)C1]

The synthesis of Example 25 was accomplished using a procedure analogous to that described in Example 18 with tert-butyl 3-(tosyloxy)pyrrolidine-1-carboxylate. ¹H NMR (400 MHz, CDCl₃) δ 7.42-7.50 (m, 2H), 7.31-7.41 (m, 2H), 7.10-7.19 (m, 1H), 7.02-7.09 (m, 4H), 6.38-6.48 (m, 2H), 5.64-5.70 (m, 1H), 5.50-5.60 (m, 2H), 5.26 (brs, 2H), 4.60-4.76 (m, 1H), 3.90-4.08 (m, 2H), 3.60-3.71 (m, 1H), 2.68-2.76 (m, 1H), 2.48-2.54 (m, 1H), 2.29-2.42 (m, 1H). m/z=418[M+1]⁺.

(R)-isomer: ¹H NMR (400 MHz, CDCl₃) δ 7.47-7.52 (m, 2H), 7.35-7.39 (m, 2H), 7.16 (t, J=7.6 Hz, 1H), 7.05-7.09 (m, 4H), 6.38-6.51 (m, 2H), 5.68-5.73 (m, 1H), 5.40-5.52 (m, 2H), 5.27 (brs, 2H), 4.60-4.75 (m, 1H), 3.91-4.09 (m, 2H), 3.60-3.76 (m, 1H), 2.69-2.79 (m, 1H), 2.50-2.61 (m, 1H), 2.29-2.48 (m, 1H). m/z=418[M+1]⁺.

(S)-isomer: ¹H NMR (400 MHz, CDCl₃) δ 7.39-7.52 (m, 2H), 7.37 (t, J=7.6 Hz, 2H), 7.16 (t, J=7.2 Hz, 1H), 7.04-7.09 (m, 4H), 6.39-6.50 (m, 2H), 5.67-5.72 (m, 1H), 5.44-5.56 (m, 2H), 5.30 (brs, 2H), 4.61-4.74 (m, 1H), 3.88-4.10 (m, 2H), 3.60-3.77 (m, 1H), 2.69-2.78 (m, 1H), 2.49-2.60 (m, 1H), 2.29-2.49 (m, 1H). m/z=418[M+1]⁺.

Example 26

5-amino-3-(4-phenoxyphenyl)-1-(1-propioloylpiperidin-3-yl)-1H-pyrazole-4-carboxamide

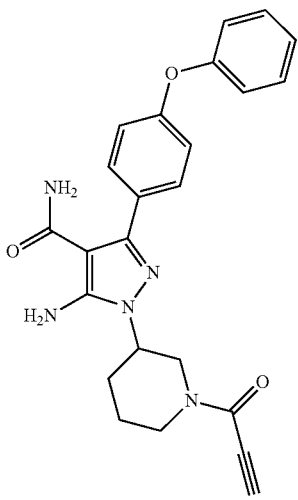 [SMILES: C#CC(=O)N1CCCC(n2nc(-c3ccc(Oc4ccccc4)cc3)c(C(N)=O)c2N)C1]

The synthesis of Example 26 was accomplished using a procedure analogous to that described in Example 18 with propioloyl chloride. $^1$H NMR (400 MHz, CDCl$_3$) δ7.45-7.53 (m, 2H), 7.32-7.40 (m, 2H), 7.15 (t, J=7.6 Hz, 1H), 7.04-7.09 (m, 4H), 5.53 (s, 2H), 5.30 (brs, 2H), 4.74 and 4.42 (d, J=13.2 Hz, 1H), 4.56 (d, J=13.2 Hz, 1H), 3.82-3.96 (m, 1H), 3.63 and 2.71 (t, J=13.2 Hz, 1H), 3.10-3.20 (m, 1H), 2.21-2.40 (m, 2H), 2.13-2.20 (m, 1H), 1.91-2.06 (m, 2H). m/z=430[M+1]$^+$.

Example 27

5-amino-3-(4-phenoxyphenyl)-1-(1-(vinylsulfonyl)piperidin-3-yl)-1H-pyrazole-4-carboxamide

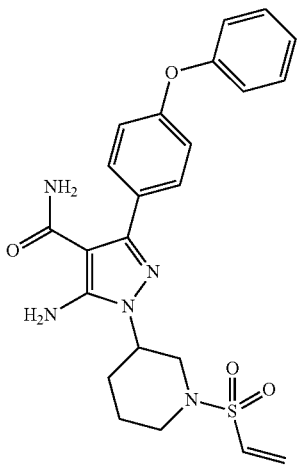 [SMILES: C=CS(=O)(=O)N1CCCC(n2nc(-c3ccc(Oc4ccccc4)cc3)c(C(N)=O)c2N)C1]

The synthesis of Example 27 was accomplished using a procedure analogous to that described in Example 18 with propioloyl chloride. $^1$H NMR (400 MHz, CDCl$_3$) δ7.48 (t, J=8.4 Hz, 2H), 7.37 (t, J=8.0 Hz, 2H), 7.16 (t, J=7.2 Hz, 1H), 7.03-7.09 (m, 4H), 6.39-6.48 (m, 1H), 6.26 (d, J=16.8 Hz, 1H), 6.03 (d, J=10.0 Hz, 1H), 6.02 (s, 2H), 5.20 (brs, 2H), 4.02-4.11 (m, 1H), 3.90 (d, J=12.0 Hz, 1H), 3.79 (d, J=12.0 Hz, 1H), 3.06 (t, J=11.2 Hz, 1H), 2.58-2.68 (m, 1H), 2.11-2.20 (m, 2H), 1.89-2.04 (m, 1H), 1.74-1.88 (m, 1H). m/z=468[M+1]$^+$.

(R)-isomer: $^1$H NMR (400 MHz, CDCl$_3$) δ7.49 (t, J=8.4 Hz, 2H), 7.37 (t, J=8.4 Hz, 2H), 7.16 (t, J=7.2 Hz, 1H), 7.03-7.09 (m, 4H), 6.40-6.46 (m, 1H), 6.26 (d, J=16.4 Hz, 1H), 6.03 (d, J=9.6 Hz, 1H), 5.57 (s, 2H), 5.21 (brs, 2H), 4.03-4.11 (m, 1H), 3.90 (d, J=11.6 Hz, 1H), 3.80 (d, J=11.6 Hz, 1H), 3.06 (t, J=11.2 Hz, 1H), 2.59-2.67 (m, 1H), 2.12-2.18 (m, 2H), 1.90-2.06 (m, 1H), 1.75-1.89 (m, 1H). m/z=468[M+1]$^+$.

Example 28

5-amino-1-(1-(2-chloroacetyl)piperidin-3-yl)-3-(4-phenoxyphenyl)-1H-pyrazole-4-carboxamide

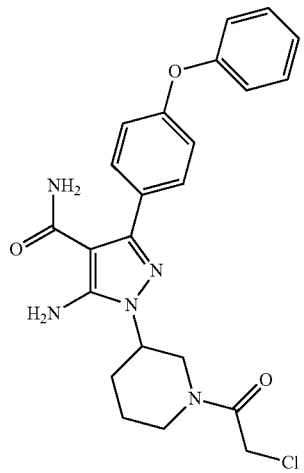 [SMILES: NC(=O)c1c(-c2ccc(Oc3ccccc3)cc2)nn(C2CCCN(C(=O)CCl)C2)c1N]

The synthesis of Example 28 was accomplished using a procedure analogous to that described in Example 18 with 2-chloroacetyl chloride. $^1$H NMR (400 MHz, CDCl$_3$) δ7.43-7.51 (m, 2H), 7.36-7.41 (m, 2H), 7.16 (t, J=5.6 Hz, 1H), 7.01-7.11 (m, 4H), 5.57 (s, 2H), 4.76 (brs, 2H), 4.75 and 4.54 (d, J=11.6 Hz, 1H), 4.18 (t, J=11.6 Hz, 1H), 3.97-4.10 (m, 2H), 3.84-3.92 (m, 1H), 3.60 and 2.72 (t, J=12.8 Hz, 1H), 3.02-3.21 (m, 1H), 2.21-2.40 (m, 2H), 2.13-2.20 (m, 1H), 1.91-2.06 (m, 2H). m/z=454[M+1]$^+$.

Example 29

(E)-5-amino-1-(1-(4-(dimethylamino)but-2-enoyl)piperidin-3-yl)-3-(4-phenoxyphenyl)-1H-pyrazole-4-carboxamide

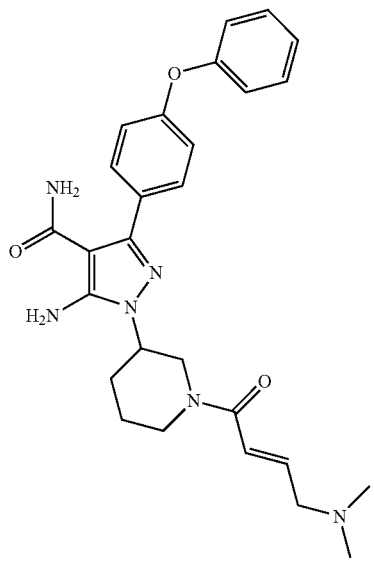 [SMILES: CN(C)C/C=C/C(=O)N1CCCC(n2nc(-c3ccc(Oc4ccccc4)cc3)c(C(N)=O)c2N)C1]

The synthesis of Example 29 was accomplished using a procedure analogous to that described in Example 18 with (E)-4-(dimethylamino)but-2-enoyl chloride. $^1$H NMR (400 MHz, CDCl$_3$) δ7.41-7.52 (m, 2H), 7.30-7.40 (m, 2H), 7.15 (t, J=7.2 Hz, 1H), 6.98-7.11 (m, 4H), 6.80-6.94 (m, 1H), 6.48 (d, J=14.8 Hz, 1H), 5.65 (s, 2H), 5.26 (brs, 2H), 4.82 and 4.04 (d, J=12.0 Hz, 1H), 4.62 and 4.19 (d, J=12.0 Hz, 1H), 3.83-4.00 (m, 1H), 3.08-3.20 (m, 4H), 2.29 (s, 6H), 2.11-2.28 (m, 1H), 1.90-2.02 (m, 1H), 1.50-1.68 (m, 2H). m/z=489[M+1]$^+$.

Example 30

5-amino-1-(2-(N-methylacrylamido)ethyl)-3-(4-phenoxyphenyl)-1H-pyrazole-4-carboxamide

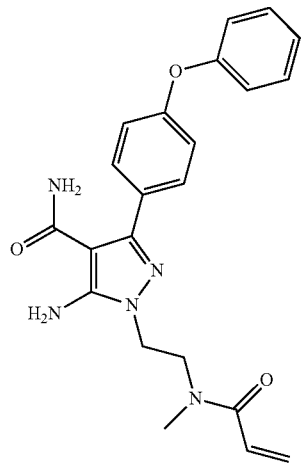 [SMILES: C=CC(=O)N(C)CCn1nc(-c2ccc(Oc3ccccc3)cc2)c(C(N)=O)c1N]

The synthesis of Example 30 was accomplished using a procedure analogous to that described in Example 18 with tert-butyl 2-chloroethyl(methyl)carbamate. $^1$H NMR (CDCl$_3$) δ7.50 (d, J=8.8 Hz, 2H), 7.37 (t, J=7.6 Hz, 2H), 7.15 (t, J=7.6 Hz, 1H), 7.08 (d, J=8.4 Hz, 2H), 7.05 (d, J=8.0 Hz, 2H), 6.56 (dd, J=16.8 Hz, 10.4 Hz, 1H), 6.39 (dd, J=16.8 Hz, 1.6 Hz, 1H), 5.96 (s, 2H), 5.76 (dd, J=16.8 Hz, 2.0 Hz, 1H), 5.20-5.29 (brs, 2H), 4.21 (t, J=6.8 Hz, 2H), 3.75 (t, J=6.8 Hz, 2H), 3.03 (s, 3H). m/z=406[M+1]$^+$.

Example 31

1-(2-acrylamidoethyl)-5-amino-3-(4-phenoxyphenyl)-1H-pyrazole-4-carboxamide

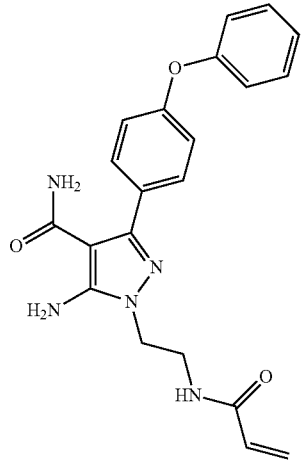 [SMILES: C=CC(=O)NCCn1nc(-c2ccc(Oc3ccccc3)cc2)c(C(N)=O)c1N]

The synthesis of Example 31 was accomplished using a procedure analogous to that described in Example 18 with tert-butyl 2-chloroethylcarbamate. $^1$H NMR (CDCl$_3$) δ 7.54 (d, J=8.4 Hz, 2H), 7.40 (t, J=8.4 Hz, 2H), 7.19 (t, J=7.2 Hz, 1H), 7.11 (d, J=8.4 Hz, 2H), 7.09 (d, J=8.4 Hz, 2H), 6.34 (d, J=16.8 Hz, 1H), 6.08-6.20 (m, 2H), 5.82 (s, 2H), 5.73 (dd, J=10.4 Hz, 1.2 Hz, 1H), 5.10-5.33 (brs, 2H), 4.15 (t, J=6.0 Hz, 2H), 3.73 (q, J=6.0 Hz, 2H). m/z=392[M+1]$^+$.

Example 32

5-amino-1-(2-(N-methylpropiolamido)ethyl)-3-(4-phenoxyphenyl)-1H-pyrazole-4-carboxamide

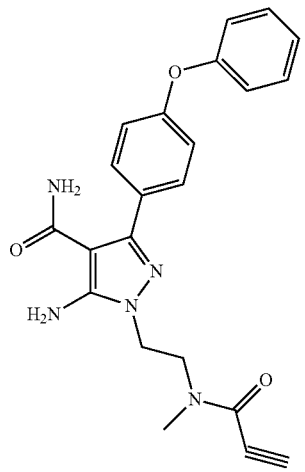 [SMILES: C#CC(=O)N(C)CCn1nc(-c2ccc(Oc3ccccc3)cc2)c(C(N)=O)c1N]

The synthesis of Example 32 was accomplished using a procedure analogous to that described in Example 18 with tert-butyl 2-chloroethyl(methyl)carbamate and propioloyl chloride. 1H NMR δ 7.50 (d, J=8.8 Hz, 2H), 7.37 (t, J=7.6 Hz, 2H), 7.15 (t, J=7.6 Hz, 1H), 7.08 (d, J=8.4 Hz, 2H), 7.05 (d, J=8.8 Hz, 2H), 5.80 (s, 2H), 5.23-5.28 (brs, 2H), 4.17 (t, J=6.8 Hz, 2H), 3.75 (t, J=6.8 Hz, 2H), 3.13 (s, 3H), 2.98 (s, 1H). m/z=404[M+1]$^+$.

Example 33

5-amino-1-(2-(N-methylvinylsulfonamido)ethyl)-3-(4-phenoxyphenyl)-1H-pyrazole-4-carboxamide

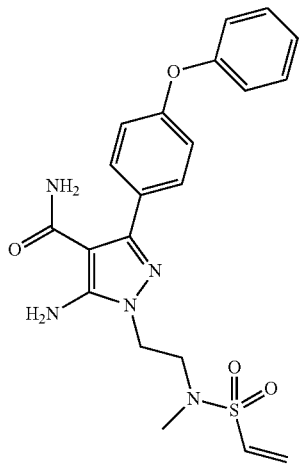 [SMILES: C=CS(=O)(=O)N(C)CCn1nc(-c2ccc(Oc3ccccc3)cc2)c(C(N)=O)c1N]

The synthesis of Example 33 was accomplished using a procedure analogous to that described in Example 18 with tert-butyl 2-chloroethyl(methyl)carbamate and ethenesulfonyl chloride. 1H NMR δ 7.50 (d, J=8.8 Hz, 2H), 7.37 (t, J=8.0 Hz, 2H), 7.15 (t, J=7.6 Hz, 1H), 7.08 (d, J=8.8 Hz, 2H), 7.04 (d, J=7.6 Hz, 2H), 6.44 (dd, J=16.4 Hz, 10.0 Hz, 1H), 6.28 (d, J=16.8 Hz, 1H), 6.05 (d, J=9.6 Hz, 1H), 5.75 (s, 2H), 5.16-5.34 (brs, 2H), 4.19 (t, J=6.0 Hz, 2H), 3.47 (t, J=6.0 Hz, 2H), 2.75 (s, 3H). m/z=442[M+1]$^+$.

Example 34

5-amino-1-(2-(2-chloro-N-methylacetamido)ethyl)-3-(4-phenoxyphenyl)-1H-pyrazole-4-carboxamide

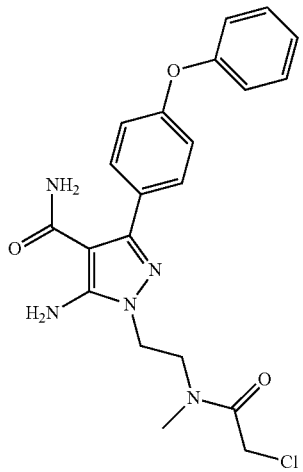 [SMILES: CN(CCn1nc(-c2ccc(Oc3ccccc3)cc2)c(C(N)=O)c1N)C(=O)CCl]

The synthesis of Example 34 was accomplished using a procedure analogous to that described in Example 18 with tert-butyl 2-chloroethyl(methyl)carbamate and 2-chloroacetyl chloride. $^1$H NMR δ 7.49 (d, J=8.4 Hz, 2H), 7.38 (t, J=8.0 Hz, 2H), 7.15 (t, J=7.6 Hz, 1H), 7.07 (d, J=8.4 Hz, 2H), 7.04 (d, J=7.6 Hz, 2H), 5.82 (s, 2H), 5.38 (s, 2H), 4.18 (t, J=6.4 Hz, 2H), 4.09 (s, 2H), 3.73 (t, J=6.4 Hz, 2H), 2.97 (s, 3H). m/z=428[M+1]$^+$.

Example 35

(E)-5-amino-1-(2-(4-(dimethylamino)-N-methylbut-2-enamido)ethyl)-3-(4-phenoxyphenyl)-1H-pyrazole-4-carboxamide

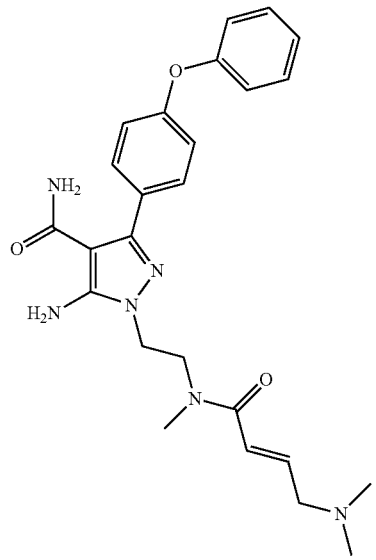 [SMILES: CN(C)C/C=C/C(=O)N(C)CCn1nc(-c2ccc(Oc3ccccc3)cc2)c(C(N)=O)c1N]

The synthesis of Example 35 was accomplished using a procedure analogous to that described in Example 18 with tert-butyl 2-chloroethyl(methyl)carbamate and (E)-4-(dimethylamino)but-2-enoyl chloride. $^1$H NMR δ 7.43-7.52 (m, 2H), 7.31-7.41 (m, 2H), 7.15 (t, J=7.2 Hz, 1H), 7.01-7.11 (m, 4H), 6.88-6.96 (m, 1H), 6.47 (d, J=15.6 Hz, 1H), 5.96 (s, 2H), 5.24 (brs, 2H), 4.19 (t, J=6.8 Hz, 2H), 3.73 (t, J=6.8 Hz, 2H), 3.21 (d, J=5.6 Hz, 2H), 3.02 (s, 3H), 2.35 (s, 6H). m/z=463[M+1]$^+$.

Example 36

1-(1-acryloylpiperidin-3-yl)-5-amino-3-(4-phenoxyphenyl)-1H-pyrazole-4-carboximidamide

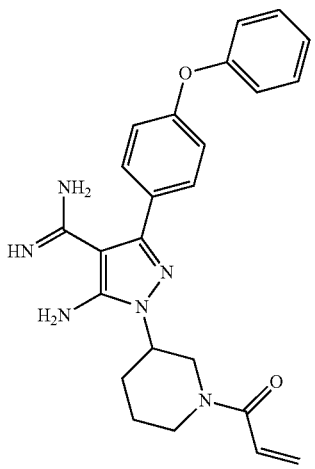 [SMILES: C=CC(=O)N1CCCC(n2nc(-c3ccc(Oc4ccccc4)cc3)c(C(=N)N)c2N)C1]

The synthesis of Example 36 was accomplished using a procedure analogous to that described in Example 18. m/z=431[M+1]⁺.

Example 37

1-(1-acryloylpiperidin-3-yl)-5-amino-3-(4-phenoxyphenyl)-1H-pyrazole-4-carbothioamide

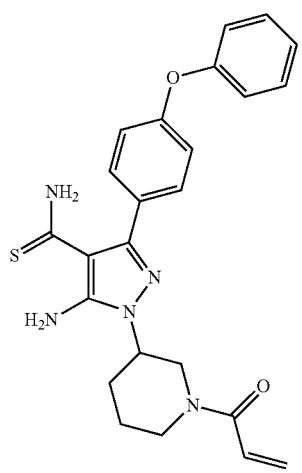 [SMILES: C=CC(=O)N1CCCC(n2nc(-c3ccc(Oc4ccccc4)cc3)c(C(N)=S)c2N)C1]

The synthesis of Example 37 was accomplished using a procedure analogous to that described in Example 18 with O,O-diethyl dithiophosphate. m/z=448[M+1]⁺.

Example 38

1-(1-acryloylpiperidin-3-yl)-2-amino-4-(4-phenoxyphenyl)-1H-pyrrole-3-carboxamide

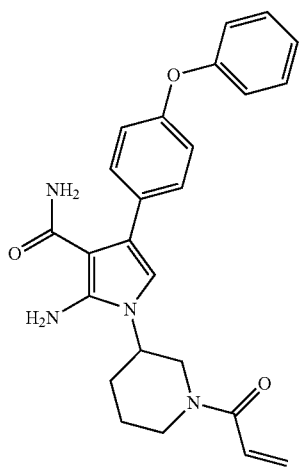 [SMILES: C=CC(=O)N1CCCC(n2cc(-c3ccc(Oc4ccccc4)cc3)c(C(N)=O)c2N)C1]

Scheme 5

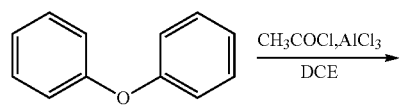

-continued

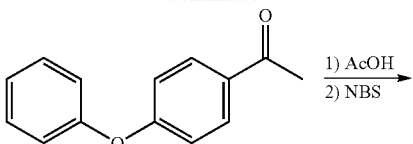

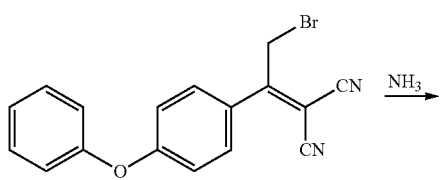

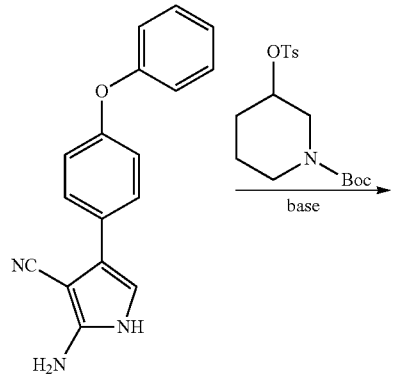

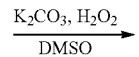

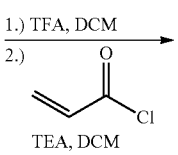

131
-continued
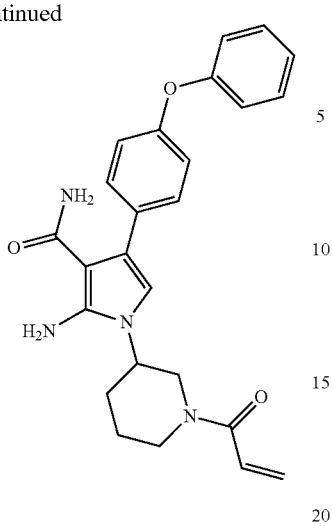
The synthesis of Example 38 was according to Scheme 5. m/z=431[M+1]⁺.
Example 39
4-(1-acryloylpiperidin-3-yl)-3-amino-1-(4-phenoxyphenyl)-1H-pyrrole-2-carboxamide
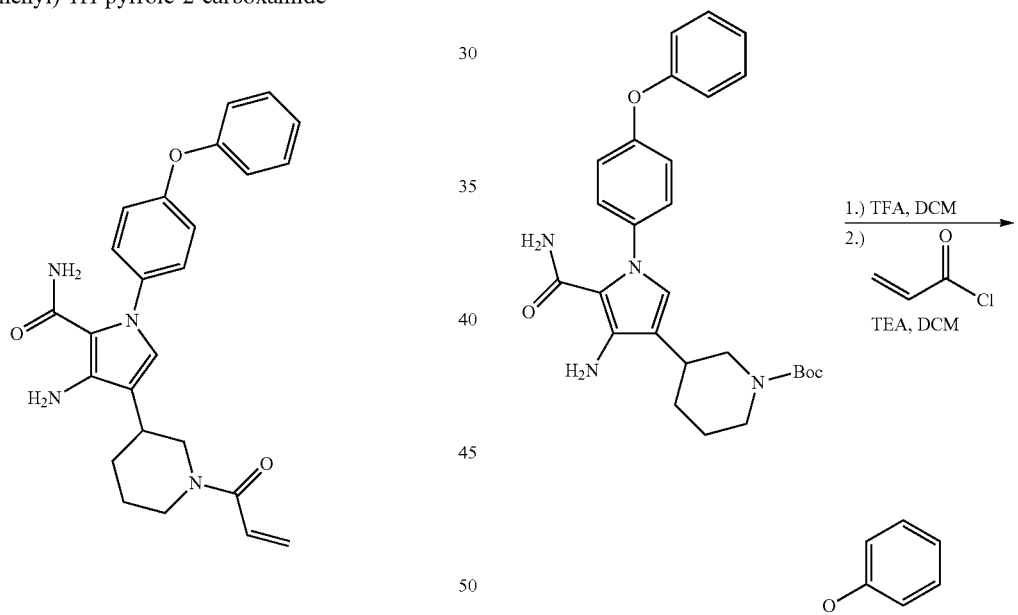
Scheme 6
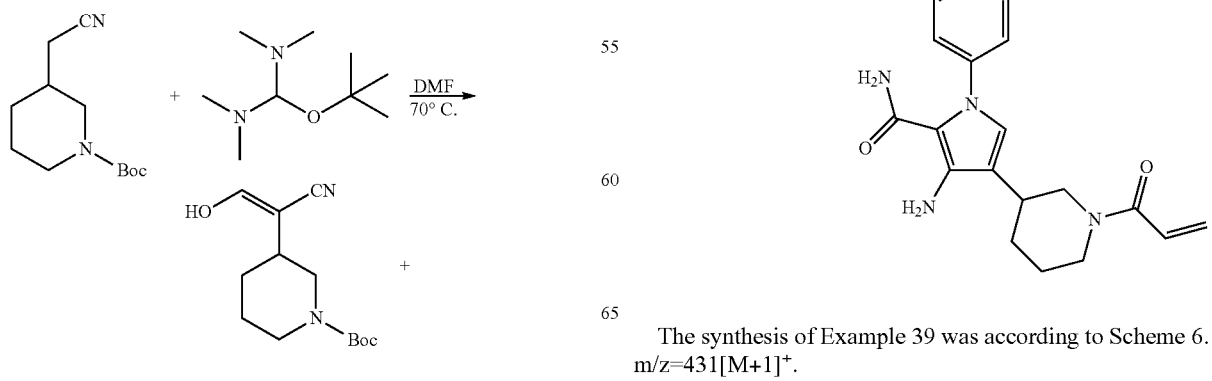
132
-continued
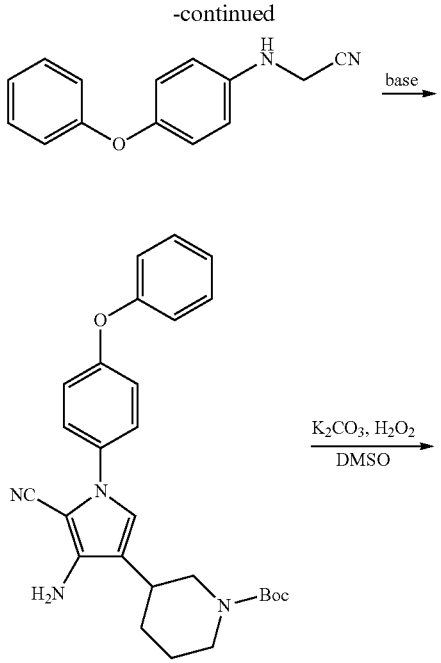
The synthesis of Example 39 was according to Scheme 6. m/z=431[M+1]⁺.

Example 40

1-(1-acryloylpiperidin-3-yl)-5-amino-N-methyl-3-(4-phenoxyphenyl)-1H-pyrazole-4-carboxamide

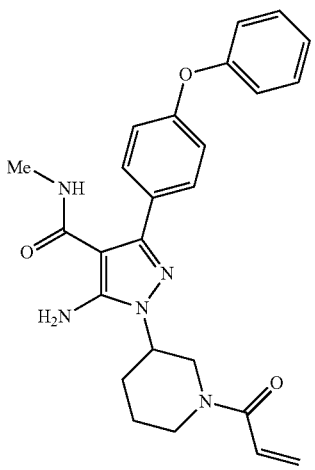 [SMILES: C=CC(=O)N1CCCC(n2nc(-c3ccc(Oc4ccccc4)cc3)c(C(=O)NC)c2N)C1]

The synthesis of Example 40 was accomplished using a procedure analogous to that described in Example 18. m/z=446[M+1]+.

Example 41

(R)-1-(1-acryloylpyrrolidin-3-yl)-5-amino-3-(4-(3,5-difluorophenoxyl)phenyl)-1H-pyrazole-4-carboxamide

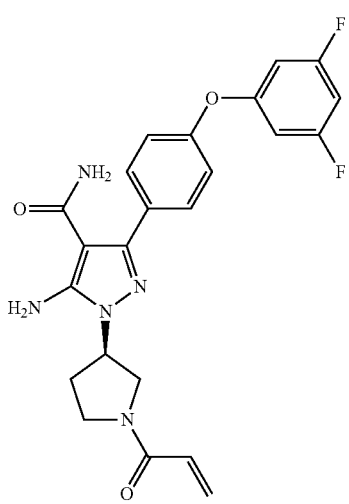 [SMILES: C=CC(=O)N1CC[C@@H](n2nc(-c3ccc(Oc4cc(F)cc(F)c4)cc3)c(C(N)=O)c2N)C1]

The synthesis of Example 41 was accomplished using a procedure analogous to that described in Example 25. $^1$H NMR (300 MHz, CDCl$_3$) δ7.56 (dd, J=8.6, 2.8 Hz, 2H), 7.13 (dd, J=8.6, 3.0 Hz, 2H), 6.53-6.61 (m, 3H), 6.37-6.47 (m, 2H), 5.67-5.74 (m, 1H), 5.58-5.61 (d, 2H), 5.25 (brs, 2H), 4.66-4.77 (m, 1H), 3.92-4.07 (m, 3H), 3.64-3.74 (m, 1H), 2.35-2.75 (m, 2H). m/z=454[M+1]+. m/z=454[M+1]+.

Example 42

(R)-1-(1-acryloylpyrrolidin-3-yl)-5-amino-3-(4-(3-methoxyphenoxyl)phenyl)-1H-pyrazole-4-carboxamide

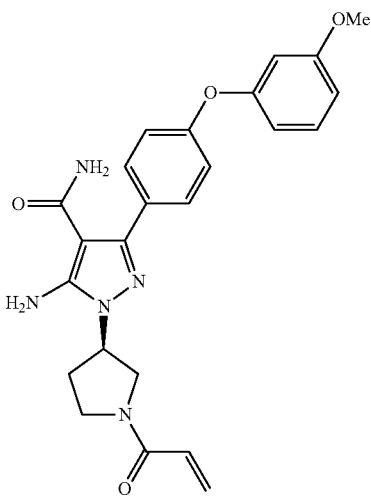 [SMILES: C=CC(=O)N1CC[C@@H](n2nc(-c3ccc(Oc4cccc(OC)c4)cc3)c(C(N)=O)c2N)C1]

The synthesis of Example 42 was accomplished using a procedure analogous to that described in Example 25. $^1$H NMR (300 MHz, CDCl$_3$) δ 7.49 (dd, J=8.7, 2.6 Hz, 2H), 7.26 (dd, J=9.4, 7.1 Hz, 1H), 7.08 (dd, J=8.5, 3.0 Hz, 2H), 6.71 (d, J=9.4 Hz, 1H), 6.63 (d, J=7.1 Hz, 1H), 6.61 (s, 1H), 6.36-6.46 (m, 2H), 5.67-5.73 (m, 1H), 5.56-5.60 (d, 2H), 5.26 (brs, 2H), 4.65-4.76 (m, 1H), 3.87-4.06 (m, 3H), 3.79 (s, 3H), 3.63-3.76 (m, 1H), 2.35-2.75 (m, 2H). m/z=448[M+1]+.

Example 43

(R)-1-(1-acryloylpyrrolidin-3-yl)-5-amino-3-(4-(4-chlorophenoxyl)phenyl)-1H-pyrazole-4-carboxamide

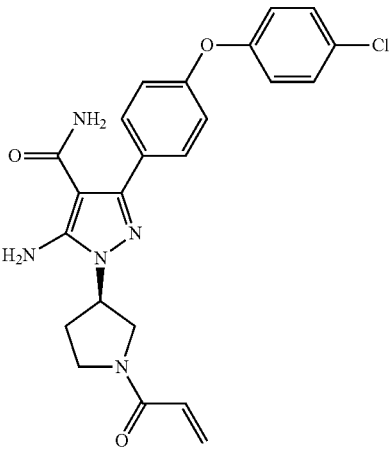 [SMILES: C=CC(=O)N1CC[C@@H](n2nc(-c3ccc(Oc4ccc(Cl)cc4)cc3)c(C(N)=O)c2N)C1]

The synthesis of Example 43 was accomplished using a procedure analogous to that described in Example 25. $^1$H NMR (300 MHz, CDCl$_3$) δ 7.50 (dd, J=8.6, 2.3 Hz, 2H), 7.32 (d, J=8.9 Hz, 2H), 7.06 (dd, J=8.6, 2.8 Hz, 2H), 6.99 (d, J=8.9 Hz, 2H), 6.38-6.46 (m, 2H), 5.67-5.73 (m, 1H), 5.55-5.58 (d, 2H), 5.26 (brs, 2H), 4.65-4.73 (m, 1H), 3.91-4.06 (m, 3H), 3.60-3.73 (m, 1H), 2.34-2.74 (m, 2H). m/z=452[M+1]⁺.

Example 44

(R)-1-(1-acryloylpyrrolidin-3-yl)-5-amino-3-(4-(3-(trifluoromethyl)phenoxy)phenyl)-1H-pyrazole-4-carboxamide

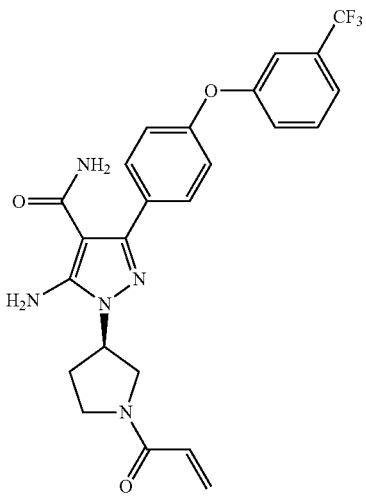 [SMILES: C=CC(=O)N1CC[C@@H](n2nc(-c3ccc(Oc4cccc(C(F)(F)F)c4)cc3)c(C(N)=O)c2N)C1]

The synthesis of Example 44 was accomplished using a procedure analogous to that described in Example 25. ¹H NMR (300 MHz, CDCl₃) δ7.62-7.73 (m, 2H), 7.58-7.62 (m, 1H), 7.48-7.50 (m, 1H), 7.28-7.31 (m, 1H), 7.19-7.24 (m, 1H), 7.02-7.14 (m, 2H), 6.32-6.48 (m, 2H), 5.71-5.77 (m, 1H), 5.56-5.63 (d, 2H), 5.25 (brs, 2H), 4.60-4.75 (m, 1H), 3.98-4.09 (m, 3H), 3.56-3.74 (m, 1H), 2.31-2.74 (m, 2H). m/z=486[M+1]⁺.

Example 45

(R)-1-(1-acryloylpyrrolidin-3-yl)-5-amino-3-(4-(2-chlorophenoxyl)phenyl)-1H-pyrazole-4-carboxamide

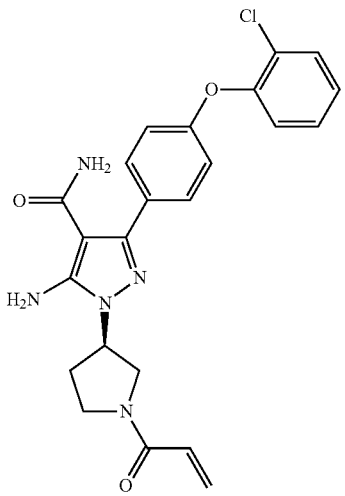 [SMILES: C=CC(=O)N1CC[C@@H](n2nc(-c3ccc(Oc4ccccc4Cl)cc3)c(C(N)=O)c2N)C1]

The synthesis of Example 45 was accomplished using a procedure analogous to that described in Example 25. ¹H NMR (300 MHz, CDCl₃) δ7.47-7.50 (m, 3H), 7.24-7.30 (m, 1H), 6.91-7.18 (m, 4H), 6.38-6.46 (m, 2H), 5.67-5.73 (m, 1H), 5.48-5.51 (d, 2H), 5.25 (brs, 2H), 4.63-4.70 (m, 1H), 3.91-4.07 (m, 3H), 3.64-3.73 (m, 1H), 2.36-2.74 (m, 2H). m/z=452[M+1]⁺.

Example 46

(R)-1-(1-acryloylpyrrolidin-3-yl)-5-amino-3-(4-(4-methoxyphenoxyl)phenyl)-1H-pyrazole-4-carboxamide

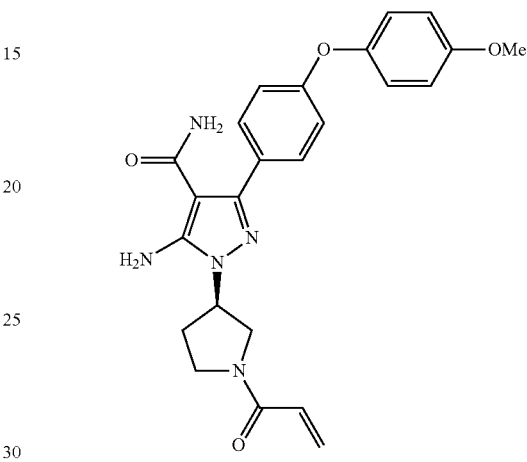

The synthesis of Example 46 was accomplished using a procedure analogous to that described in Example 25. ¹H NMR (300 MHz, CDCl₃) δ7.43-7.47 (m, 2H), 6.98-7.03 (m, 4H), 6.89-6.94 (m, 2H), 6.36-6.46 (m, 2H), 5.67-5.73 (m, 1H), 5.49-5.53 (d, 2H), 5.23 (brs, 2H), 4.63-4.74 (m, 1H), 3.89-4.07 (m, 3H), 3.82 (s, 3H), 3.63-3.75 (m, 1H), 2.32-2.75 (m, 2H). m/z=448[M+1]⁺.

Example 47

(R)-1-(1-acryloylpyrrolidin-3-yl)-5-amino-3-(4-(2-methyl-5-nitrophenoxy)phenyl)-1H-pyrazole-4-carboxamide

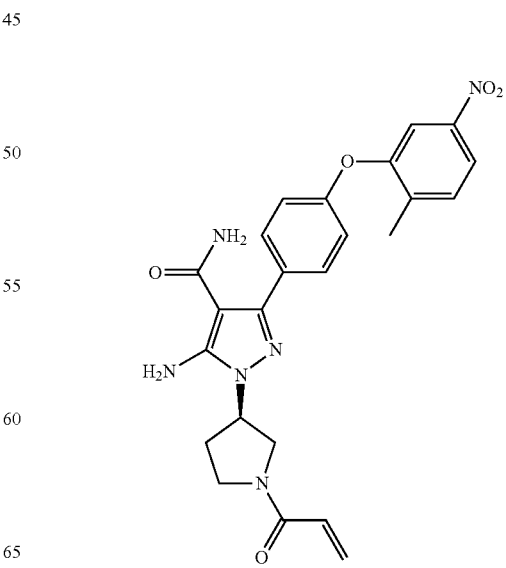

The synthesis of Example 47 was accomplished using a procedure analogous to that described in Example 25. $^1$H NMR (300 MHz, CDCl$_3$) δ 7.96 (d, J=7.1 Hz, 1H), 7.76 (s, 1H), 7.55 (d, J=8.6 Hz, 2H), 7.43 (d, J=8.2 Hz, 1H), 7.04 (d, J=8.6 Hz, 2H), 6.39-6.44 (m, 2H), 5.69-5.75 (m, 1H), 5.49-5.52 (d, 2H), 5.24 (brs, 2H), 4.65-4.76 (m, 1H), 3.88-4.06 (m, 3H), 3.65-3.75 (m, 1H), 2.39 (s, 3H), 2.35-2.75 (m, 2H). m/z=477[M+1]$^+$.

Example 48

(R)-1-(1-acryloylpyrrolidin-3-yl)-5-amino-3-(4-(4-methyl-3-nitrophenoxy)phenyl)-1H-pyrazole-4-carboxamide

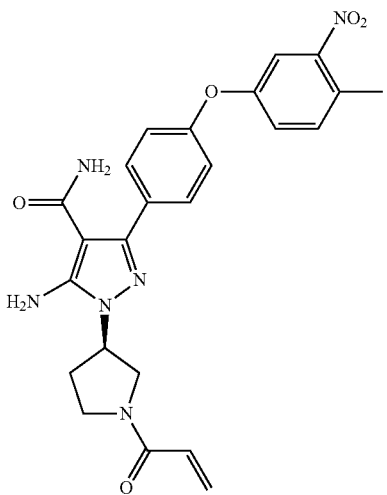 [SMILES: C=CC(=O)N1CC[C@@H](n2nc(-c3ccc(Oc4ccc(C)c([N+](=O)[O-])c4)cc3)c(C(N)=O)c2N)C1]

The synthesis of Example 48 was accomplished using a procedure analogous to that described in Example 25. $^1$H NMR (300 MHz, CDCl$_3$) δ 7.65 (d, J=2.5 Hz, 1H), 7.55 (dd, J=8.8, 3.0 Hz, 2H), 7.33 (d, J=8.4 Hz, 1H), 7.21 (dd, J=8.3, 2.6 Hz, 1H), 7.10 (dd, J=8.7, 3.0 Hz, 2H), 6.37-6.44 (m, 2H), 5.68-5.73 (m, 1H), 5.50-5.54 (d, 2H), 5.23 (brs, 2H), 4.64-4.72 (m, 1H), 3.87-4.11 (m, 3H), 3.65-3.76 (m, 1H), 2.58 (s, 3H), 2.33-2.75 (m, 2H). m/z=477[M+1]$^+$.

Example 49

(R)-1-(1-acryloylpyrrolidin-3-yl)-5-amino-3-(3-methyl-4-(3-nitrophenoxy)phenyl)-1H-pyrazole-4-carboxamide

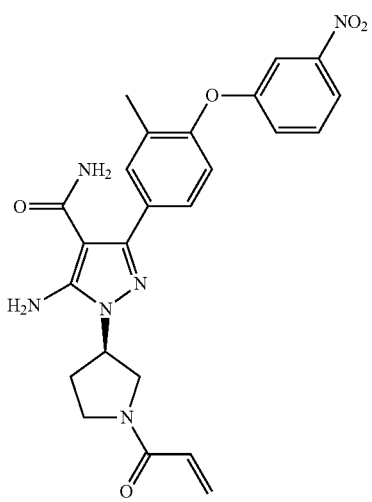 [SMILES: C=CC(=O)N1CC[C@@H](n2nc(-c3ccc(Oc4cccc([N+](=O)[O-])c4)c(C)c3)c(C(N)=O)c2N)C1]

The synthesis of Example 49 was accomplished using a procedure analogous to that described in Example 25. $^1$H NMR (300 MHz, CDCl$_3$) δ 7.93-7.96 (m, 1H), 7.75-7.76 (m, 1H), 7.47-7.52 (m, 2H), 7.38-7.41 (m, 1H), 7.26-7.30 (m, 1H), 7.00-7.04 (m, 1H), 6.37-6.48 (m, 2H), 5.68-5.74 (m, 1H), 5.54-5.57 (d, 2H), 5.27 (brs, 2H), 4.66-4.74 (m, 1H), 3.93-4.08 (m, 3H), 3.65-3.74 (m, 1H), 2.40-2.77 (m, 2H), 2.27 (s, 3H). m/z=477[M+1]$^+$.

Example 50

(R)-1-(1-acryloylpyrrolidin-3-yl)-5-amino-3-(3-methyl-4-phenoxyphenyl)-1H-pyrazole-4-carboxamide

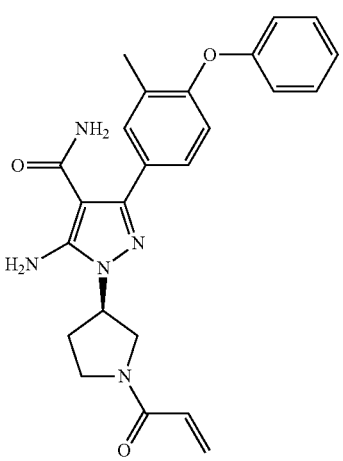 [SMILES: C=CC(=O)N1CC[C@@H](n2nc(-c3ccc(Oc4ccccc4)c(C)c3)c(C(N)=O)c2N)C1]

The synthesis of Example 50 was accomplished using a procedure analogous to that described in Example 25. $^1$H NMR (400 MHz, CDCl$_3$) δ. m/z=432[M+1]$^+$.

Biological Activity

Generation of IC$_{50}$ Data

Btk In Vitro Inhibitory Activity:

The Btk IC$_{50}$s of the compounds disclosed herein were determined in both a kinase enzymatic assay and in a cellular functional assay of BCR-induced calcium flux as described below.

Btk kinase activity was determined using a Homogeneous Time-Resolved Fluorescence (HTRF) methodology (Cisbio). Measurements were performed in a reaction volume of 10 μL using 384-well (OptiPlate-384, purchased from Perkin Elmer) assay plates. Compounds were 3-fold serially diluted with 100% DMSO from 1 mM (11 concentrations), then 4 μL of the compounds of each concentration were transferred to 96 μL of the reaction buffer (50 mM HEPES, pH7.4, 10 mM MgCl$_2$, 1 mM EGTA, 0.01% Tween-20, 0.005% BAS, 2 mM DTT), Then 2.5 μL of the mixture was added to a 384-well plate (OptiPlate-384, purchased from PerkinElmer), followed by addition of 5 μL of BTK kinase (purchased from Millipore). The mixture was centrifuged and incubated for 5 min. Then 2.5 μL of (ATP (ATP at K$_m$)+TK peptide) (HTRF® KinEASE™-TK, purchased from Cisbio) was added to the reaction system and the reaction was initiated (the total reaction volume was 10 μL). The assay plate was incubated at 23° C. in an incubator for 120 min, then the reaction was quenched by addition of 5 μL of Eu3+ cryptate-labeled anti-phosphotyrosine antibody (purchased from Cisbio) and 5 μL of Streptavidin-XL-665

(HTRF® KinEASE™-TK, purchased from Cisbio), respectively, and the mixture was allowed to incubate for one hour. The HTRF signal was measured on a multimode plate reader (Envision, purchased from Perkin Elmer) with an excitation wavelength ($\lambda_{Ex}$) of 320 nm and detection wavelengths ($\lambda_{Ex}$) of 615 and 665 nm. Activity was determined by the ratio of the fluorescence at 665 nm to that at 615 nm. For each compound, enzyme activity was measured at various concentrations of compound, and $IC_{50}$s were obtained by GraFit Software 6.0 (Erithacus Software).

Calcium flux fluorescence-based assays were performed using Fluo-4 Direct™ Calcium Assay Kits (purchased from Invitrogen) in a FlexStation III (purchased from Molecular Devices) according to manufacturer instructions. In brief, actively growing Romas cells in RPM1-1640 medium (purchased from Invitrogen) supplemented with 10% FBS (purchased from Hyclone) were washed and re-plated in low serum medium at approximately $1\times10^5$ cells per 45 µL per well in a 96-well plate (purchased from Corning), then added 45 µL of dye (purchased from Invitrogen) and incubated at 37 degree for 1 hour. Compounds to be assayed were dissolved and 3-fold serially diluted in DMSO and then diluted by 100 times in low serum medium. Then 10 µL of the diluted mixture were added to the above 96-well plate (final DMSO concentration was 0.1%) and incubated at 37 degree in 5% $CO_2$ incubator for 0.5 hour. The compound-treated cells were stimulated with a goat anti-human IgM antibody (10 µg/ml; purchased from SouthernBiotech) and read in the FlexStation III using a $\lambda_{Ex}$=494 nM and $\lambda_{Ex}$=516 nM for 90 seconds. The relative fluorescence unit (RFU) and the $IC_{50}$ were recorded and analyzed using a GraphPad Prism 5 (GraphPad Software).

Biological Data for Select Compounds

Select compounds prepared as described above were assayed according to the biological procedures described herein. The results are given in the table below:

| Example No. | Structure | Btk $IC_{50}$ (nM) | Ramos Cell Ca Flux $IC_{50}$ (nM) |
|---|---|---|---|
| 1 | 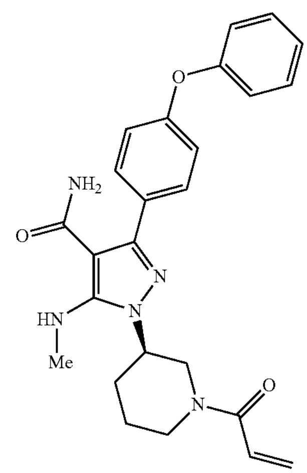 [SMILES: C=CC(=O)N1CCC[C@@H](n2nc(-c3ccc(Oc4ccccc4)cc3)c(C(N)=O)c2NC)C1] | <100 | <100 |
| 2 | 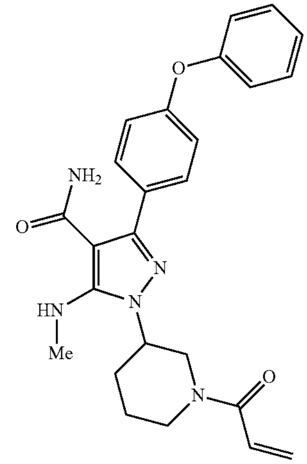 [SMILES: C=CC(=O)N1CCCC(n2nc(-c3ccc(Oc4ccccc4)cc3)c(C(N)=O)c2NC)C1] | <100 | <100 |

-continued

| Example No. | Structure | Btk IC$_{50}$ (nM) | Ramos Cell Ca Flux IC$_{50}$ (nM) |
|---|---|---|---|
| 6 | 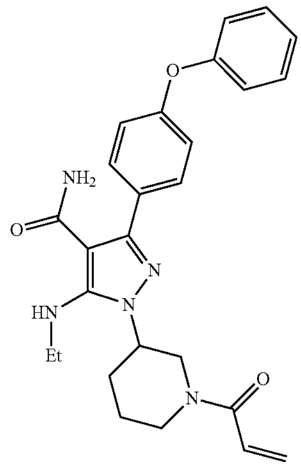 [SMILES: C=CC(=O)N1CCCC(n2nc(-c3ccc(Oc4ccccc4)cc3)c(C(N)=O)c2NCC)C1] | <100 | <100 |
| 13 | 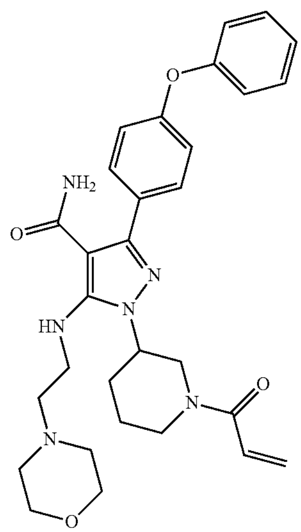 [SMILES: C=CC(=O)N1CCCC(n2nc(-c3ccc(Oc4ccccc4)cc3)c(C(N)=O)c2NCCN2CCOCC2)C1] | <100 | <100 |
| 15 | 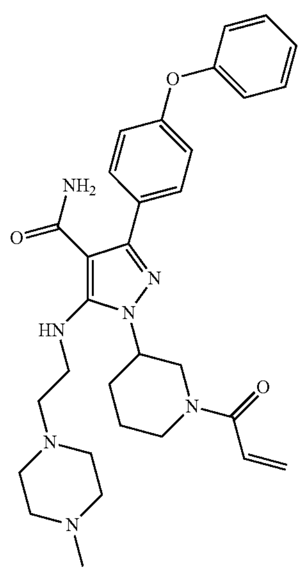 [SMILES: C=CC(=O)N1CCCC(n2nc(-c3ccc(Oc4ccccc4)cc3)c(C(N)=O)c2NCCN2CCN(C)CC2)C1] | <100 | <100 |

-continued
| Example No. | Structure | Btk IC$_{50}$ (nM) | Ramos Cell Ca Flux IC$_{50}$ (nM) |
| --- | --- | --- | --- |
| 18 | 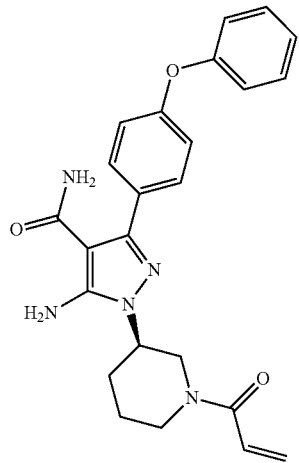 [SMILES: C=CC(=O)N1CCC[C@@H](n2nc(-c3ccc(Oc4ccccc4)cc3)c(C(N)=O)c2N)C1] | <100 | <100 |
| 20 | 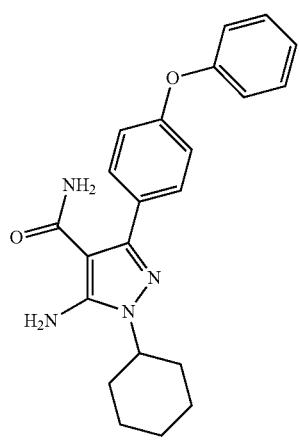 [SMILES: NC(=O)c1c(-c2ccc(Oc3ccccc3)cc2)nn(C2CCCCC2)c1N] | <100 | <100 |
| 22 | 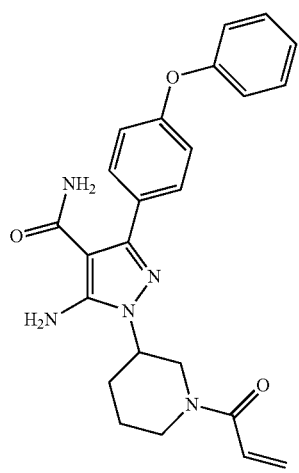 | <100 | <100 |

-continued

| Example No. | Structure | Btk IC$_{50}$ (nM) | Ramos Cell Ca Flux IC$_{50}$ (nM) |
|---|---|---|---|
| 23 | 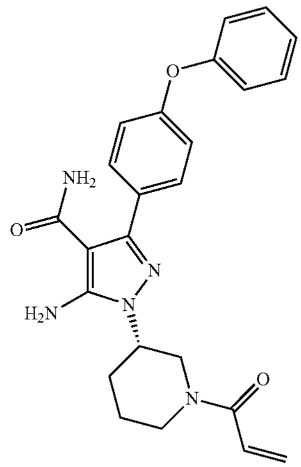 [SMILES: C=CC(=O)N1CCCC(n2nc(-c3ccc(Oc4ccccc4)cc3)c(C(N)=O)c2N)C1] | <100 | <100 |
| 24 | 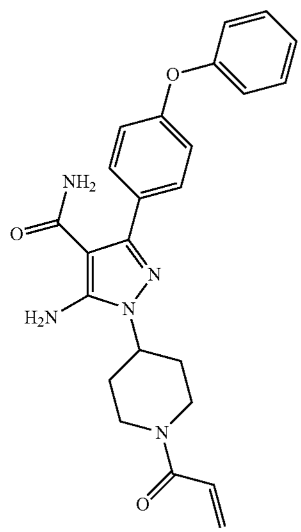 [SMILES: C=CC(=O)N1CCC(n2nc(-c3ccc(Oc4ccccc4)cc3)c(C(N)=O)c2N)CC1] | <100 | <100 |
| 25 | 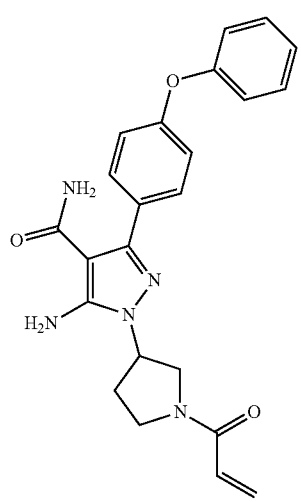 [SMILES: C=CC(=O)N1CCC(n2nc(-c3ccc(Oc4ccccc4)cc3)c(C(N)=O)c2N)C1] | <100 | <100 |

-continued
| Example No. | Structure | Btk IC$_{50}$ (nM) | Ramos Cell Ca Flux IC$_{50}$ (nM) |
|---|---|---|---|
| 25 (R-isomer) | 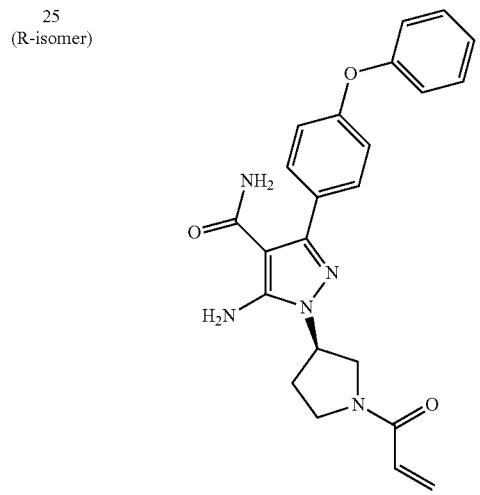 | <100 | <100 |
| 25 (S-isomer) | 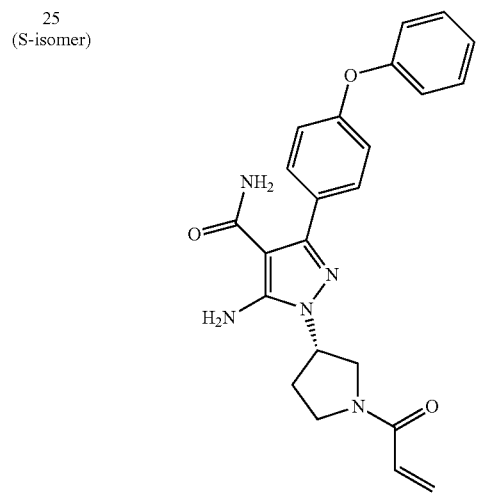 | <100 | <100 |
| 26 | 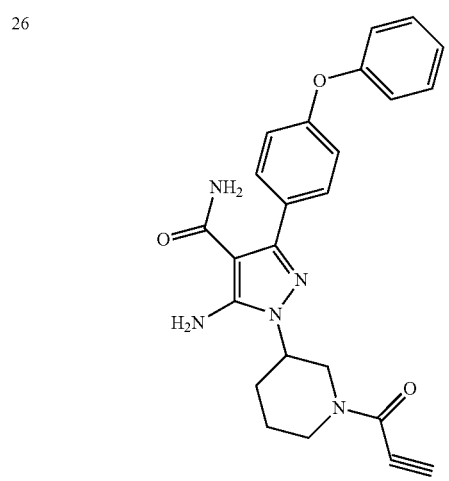 | <100 | <100 |

| Example No. | Structure | Btk IC$_{50}$ (nM) | Ramos Cell Ca Flux IC$_{50}$ (nM) |
|---|---|---|---|
| 27 | 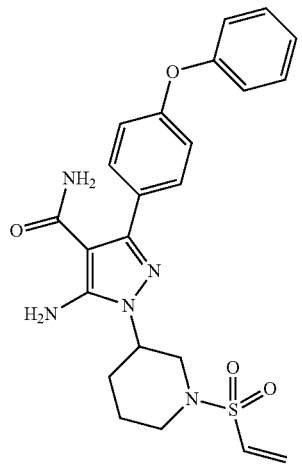 [SMILES: C=CS(=O)(=O)N1CCCC(n2nc(-c3ccc(Oc4ccccc4)cc3)c(C(N)=O)c2N)C1] | <100 | <100 |
| 27 (R-isomer) | 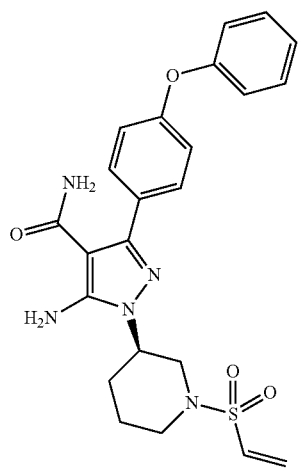 [SMILES: C=CS(=O)(=O)N1CCC[C@@H](n2nc(-c3ccc(Oc4ccccc4)cc3)c(C(N)=O)c2N)C1] | <100 | <100 |
| 28 | 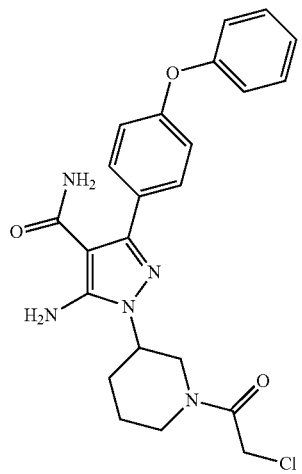 [SMILES: NC(=O)c1c(-c2ccc(Oc3ccccc3)cc2)nn(C2CCCN(C(=O)CCl)C2)c1N] | <100 | <100 |

-continued

| Example No. | Structure | Btk IC$_{50}$ (nM) | Ramos Cell Ca Flux IC$_{50}$ (nM) |
|---|---|---|---|
| 29 | 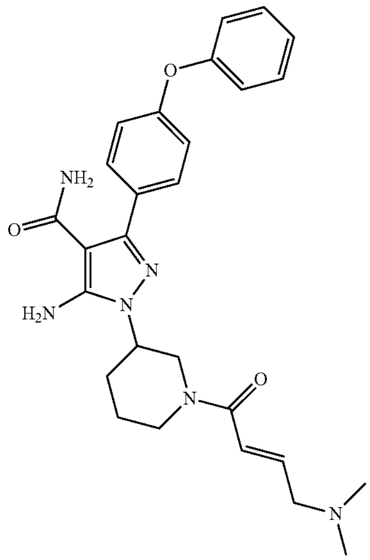 [SMILES: CN(C)C/C=C/C(=O)N1CCCC(n2nc(-c3ccc(Oc4ccccc4)cc3)c(C(N)=O)c2N)C1] | <100 | <100 |
| 30 | 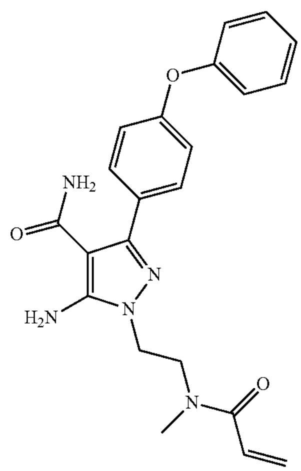 [SMILES: C=CC(=O)N(C)CCn1nc(-c2ccc(Oc3ccccc3)cc2)c(C(N)=O)c1N] | <100 | <100 |
| 31 | 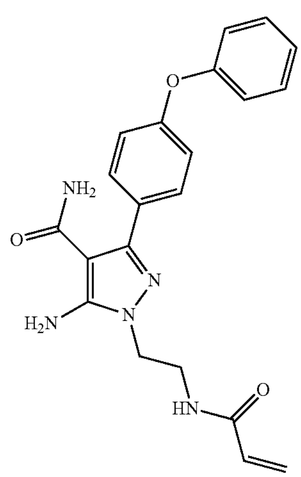 [SMILES: C=CC(=O)NCCn1nc(-c2ccc(Oc3ccccc3)cc2)c(C(N)=O)c1N] | <100 | <100 |

-continued
| Example No. | Structure | Btk IC$_{50}$ (nM) | Ramos Cell Ca Flux IC$_{50}$ (nM) |
|---|---|---|---|
| 32 | 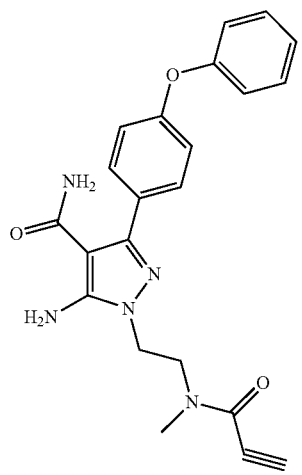 [SMILES: C#CC(=O)N(C)CCn1nc(-c2ccc(Oc3ccccc3)cc2)c(C(N)=O)c1N] | <100 | <100 |
| 33 | 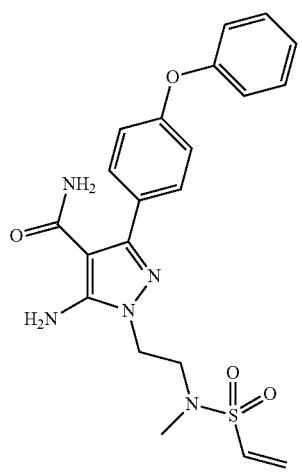 [SMILES: C=CS(=O)(=O)N(C)CCn1nc(-c2ccc(Oc3ccccc3)cc2)c(C(N)=O)c1N] | <100 | <100 |
| 34 | 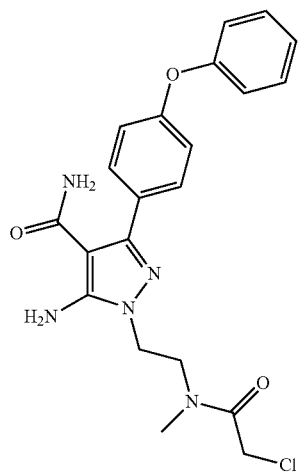 [SMILES: CN(CCn1nc(-c2ccc(Oc3ccccc3)cc2)c(C(N)=O)c1N)C(=O)CCl] | <100 | <100 |

-continued
| Example No. | Structure | Btk IC$_{50}$ (nM) | Ramos Cell Ca Flux IC$_{50}$ (nM) |
| --- | --- | --- | --- |
| 35 | 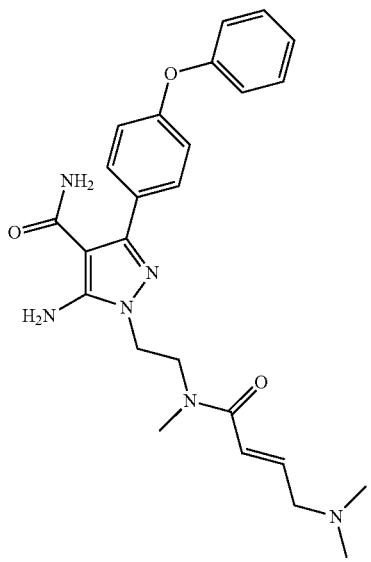 [SMILES: CN(C)C/C=C/C(=O)N(C)CCn1nc(-c2ccc(Oc3ccccc3)cc2)c(C(N)=O)c1N] | <100 | <100 |
| 37 | 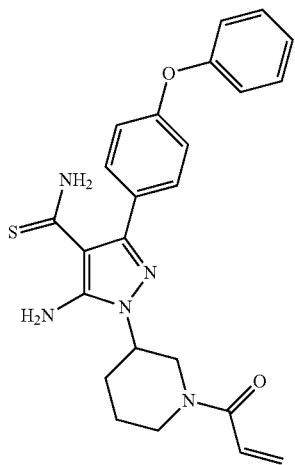 [SMILES: C=CC(=O)N1CCCC(n2nc(-c3ccc(Oc4ccccc4)cc3)c(C(N)=S)c2N)C1] | <100 | <100 |
| 41 | 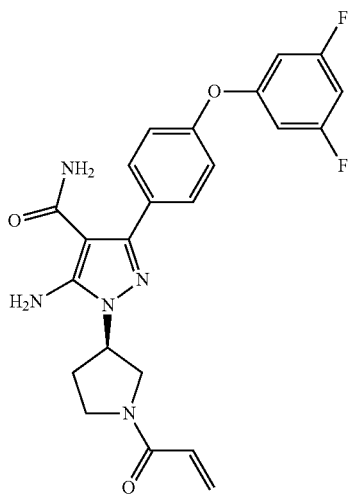 [SMILES: C=CC(=O)N1CC[C@@H](n2nc(-c3ccc(Oc4cc(F)cc(F)c4)cc3)c(C(N)=O)c2N)C1] | <100 | <100 |

-continued
| Example No. | Structure | Btk IC$_{50}$ (nM) | Ramos Cell Ca Flux IC$_{50}$ (nM) |
|---|---|---|---|
| 42 | 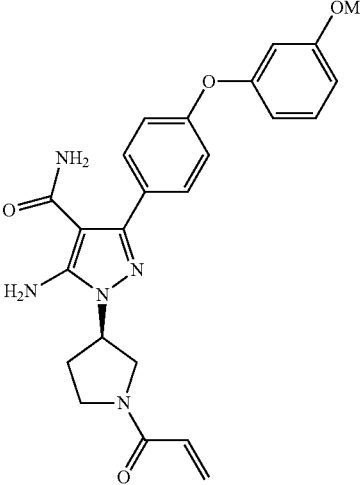 | <100 | <100 |
| 43 | 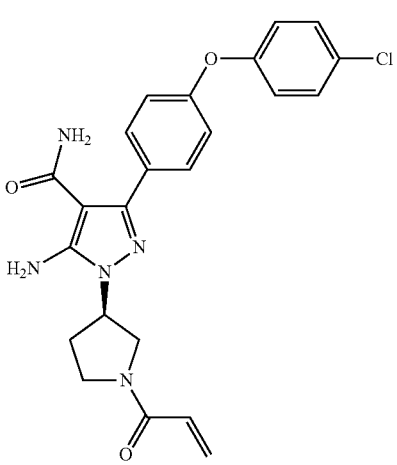 [SMILES: C=CC(=O)N1CC[C@@H](n2nc(-c3ccc(Oc4ccc(Cl)cc4)cc3)c(C(N)=O)c2N)C1] | <100 | <100 |
| 44 | 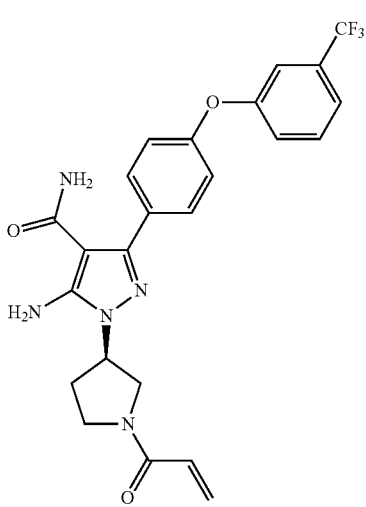 [SMILES: C=CC(=O)N1CC[C@@H](n2nc(-c3ccc(Oc4cccc(C(F)(F)F)c4)cc3)c(C(N)=O)c2N)C1] | <100 | <100 |

-continued
| Example No. | Structure | Btk IC$_{50}$ (nM) | Ramos Cell Ca Flux IC$_{50}$ (nM) |
|---|---|---|---|
| 45 | 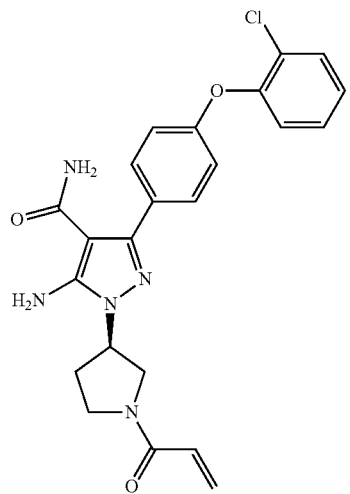 [SMILES: C=CC(=O)N1CC[C@@H](n2nc(-c3ccc(Oc4ccccc4Cl)cc3)c(C(N)=O)c2N)C1] | <100 | <100 |
| 46 | 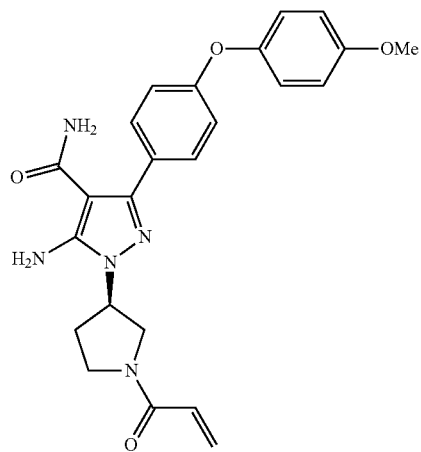 [SMILES: C=CC(=O)N1CC[C@@H](n2nc(-c3ccc(Oc4ccc(OC)cc4)cc3)c(C(N)=O)c2N)C1] | <100 | <100 |
| 47 | 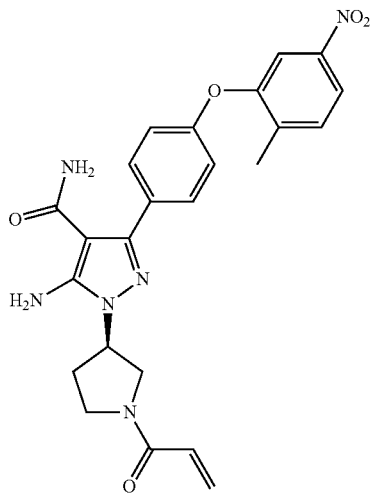 [SMILES: C=CC(=O)N1CC[C@@H](n2nc(-c3ccc(Oc4cc([N+](=O)[O-])ccc4C)cc3)c(C(N)=O)c2N)C1] | <100 | <100 |

| Example No. | Structure | Btk IC$_{50}$ (nM) | Ramos Cell Ca Flux IC$_{50}$ (nM) |
|---|---|---|---|
| 48 | 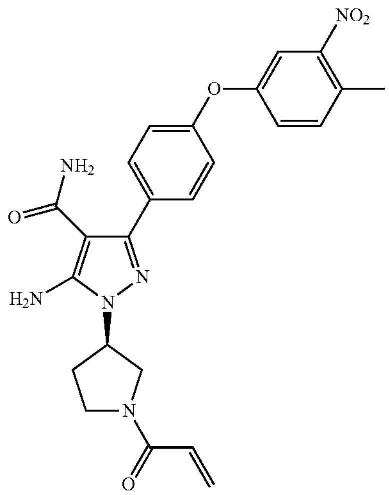 [SMILES: C=CC(=O)N1CC[C@@H](n2nc(-c3ccc(Oc4ccc(C)c([N+](=O)[O-])c4)cc3)c(C(N)=O)c2N)C1] | <100 | <100 |
| 49 | 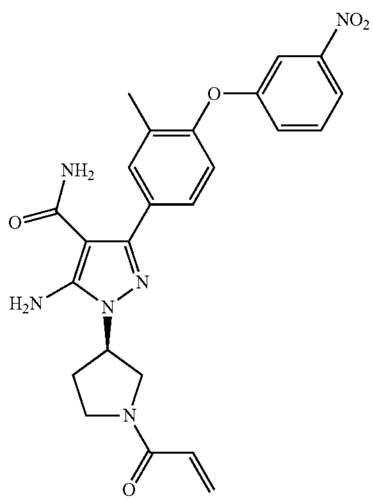 [SMILES: C=CC(=O)N1CC[C@@H](n2nc(-c3ccc(Oc4cccc([N+](=O)[O-])c4)c(C)c3)c(C(N)=O)c2N)C1] | <100 | <100 |

What is claimed is:

1. A compound represented by Formula (IV),

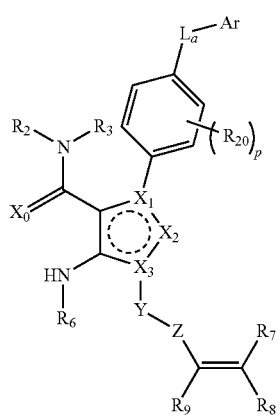

Formula (IV)

or a therapeutically acceptable salt, solvate, polymorph, ester, tautomer, or prodrug thereof, wherein:

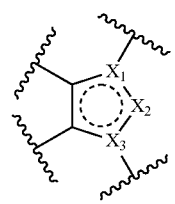

is an aromatic ring;

$L_a$ is selected from the group consisting of a bond, O, S, and NH;

$X_0$ is selected from the group consisting of O, NH and S;

$X_1$ and $X_3$ are independently selected from the group consisting of C and N;

$X_2$ is N;

$R_2$ and $R_3$ are independently selected from the group consisting of H and $C_{1-4}$ alkyl;

$R_{20}$ is independently selected from the group consisting of H, and optionally substituted lower alkyl;

Ar is selected from the group consisting of optionally substituted aryl and optionally substituted heteroaryl;

Y is selected from the group consisting of

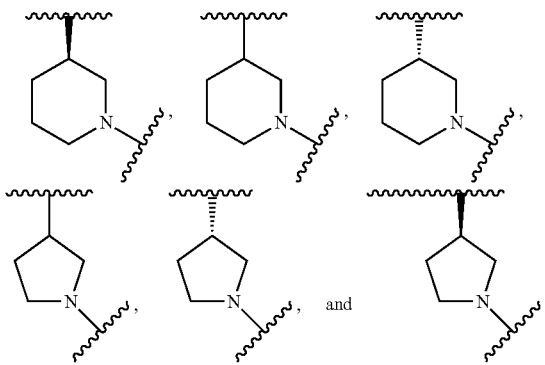

Z is selected from the group consisting of C(=O), C(=S), and S(=O)$_r$, OS(=O)$_r$, wherein r is 1 or 2;

$R_6$ is selected from the group consisting of H and —C$_{1-8}$ alkyl;

$R_7$ is selected from the group consisting of H, and optionally substituted C$_{1-4}$alkyl;

$R_8$ is selected from the group consisting of H, and optionally substituted C$_{1-4}$ alkyl, with the proviso that when Y is

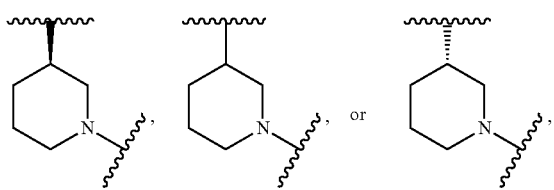 [SMILES: *[C@@H]1CCCN(*)C1 ; *C1CCCN(*)C1 ; *[C@H]1CCCN(*)C1]

$R_8$ is not H;

$R_9$ is selected from the group consisting of H, and optionally substituted C$_{1-4}$ alkyl; or $R_8$ and $R_9$ may join to form a bond; and p is 0, 1, 2, 3, or 4.

2. A compound according to claim 1 and represented by Formula (V),

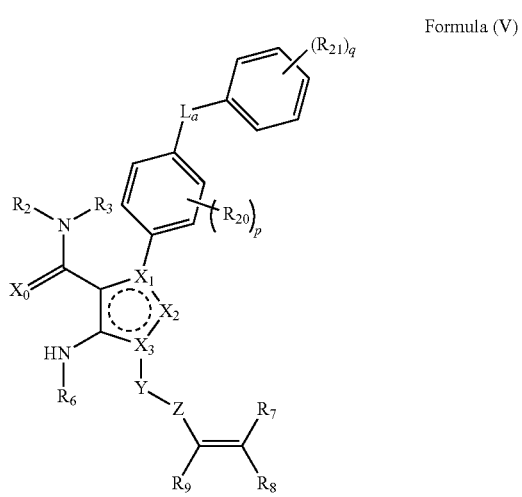

Formula (V)

or a therapeutically acceptable salt, solvate, polymorph, ester, tautomer, or prodrug thereof, wherein:

$R_{21}$ is selected from the group consisting of H, NO$_2$, OMe, OH, NH$_2$, CF$_3$, halogen, optionally substituted lower alkyl, optionally substituted lower heteroalkyl, optionally substituted lower cycloalkyl, and optionally substituted lower heterocycloalkyl; and q is 0, 1, 2, 3, 4, or 5.

3. A compound according to claim 1, or a therapeutically acceptable salt, solvate, polymorph, ester, tautomer, or prodrug thereof, wherein $X_1$ is C, $X_3$ is N; or $X_1$ is N, and $X_3$ is C.

4. A compound according to claim 1, or a therapeutically acceptable salt, solvate, polymorph, ester, tautomer, or prodrug thereof, wherein $R_7$ is H.

5. A compound according to claim 1, or a therapeutically acceptable salt, solvate, polymorph, ester, tautomer, or prodrug thereof, wherein Z is C(=O), S(=O)$_2$, or S(=O).

6. A compound according to claim 1, or a therapeutically acceptable salt, solvate, polymorph, ester, tautomer, or prodrug thereof, wherein Ar is phenyl.

7. A compound according to claim 2, or a therapeutically acceptable salt, solvate, polymorph, ester, tautomer, or prodrug thereof, wherein $R_{21}$ is independently selected from the group consisting of H, NO$_2$, OMe, CF$_3$, halogen, optionally substituted C$_{1-4}$ alkyl, and C$_{1-4}$ heteroalkyl.

8. A compound, represented by any of the following formula:

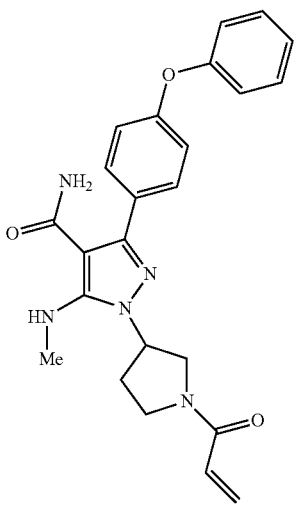 [SMILES: C=CC(=O)N1CCC(n2nc(-c3ccc(Oc4ccccc4)cc3)c(C(N)=O)c2NC)C1]

165
-continued
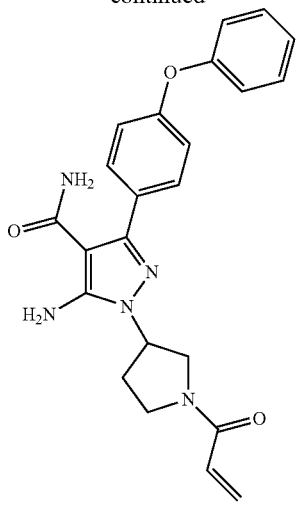
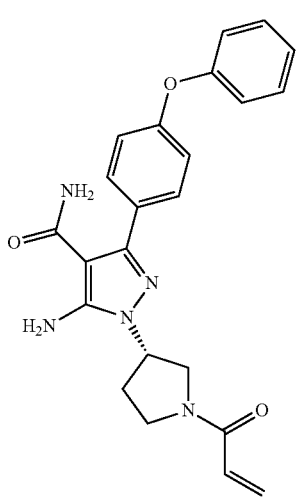
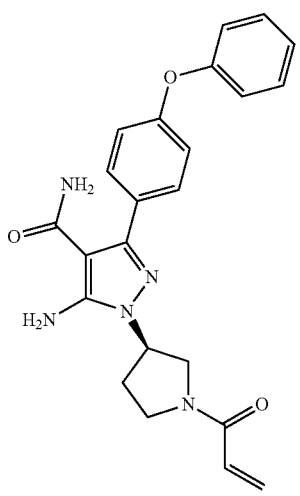
166
-continued
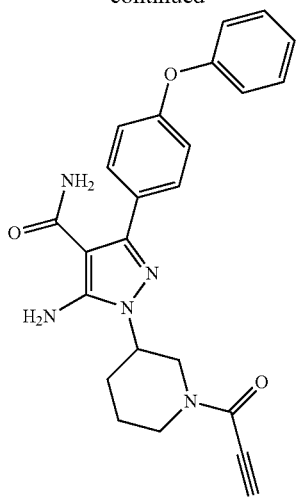
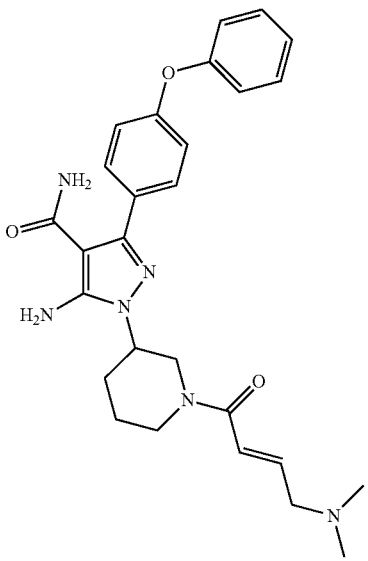 [SMILES: CN(C)C/C=C/C(=O)N1CCCC(n2nc(-c3ccc(Oc4ccccc4)cc3)c(C(N)=O)c2N)C1]
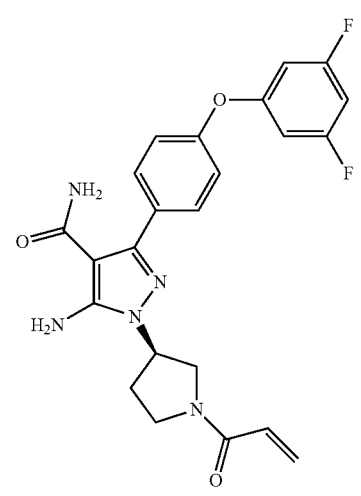 [SMILES: C=CC(=O)N1CC[C@@H](n2nc(-c3ccc(Oc4cc(F)cc(F)c4)cc3)c(C(N)=O)c2N)C1]

167
-continued
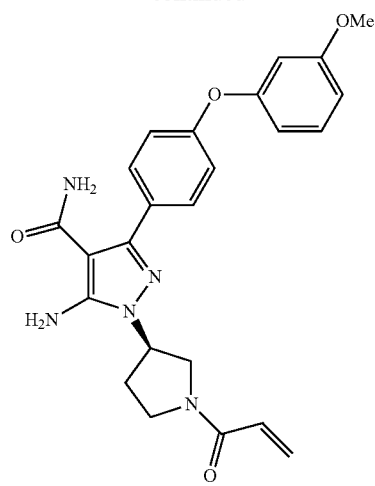
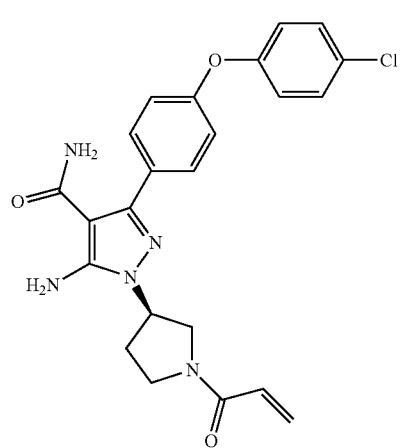
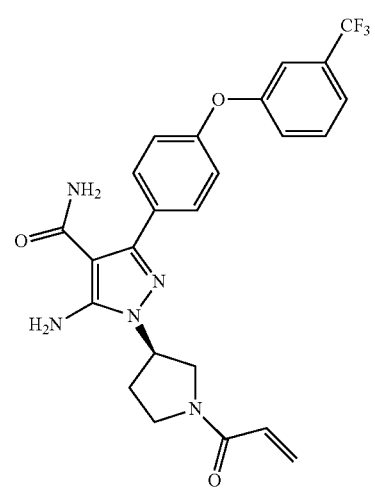
168
-continued
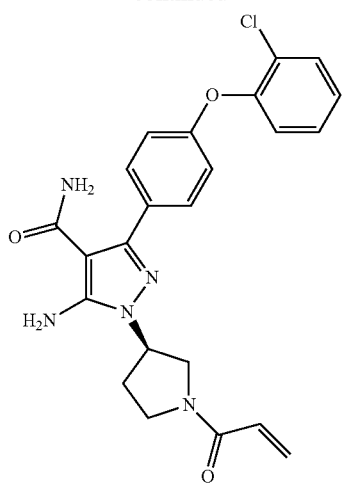
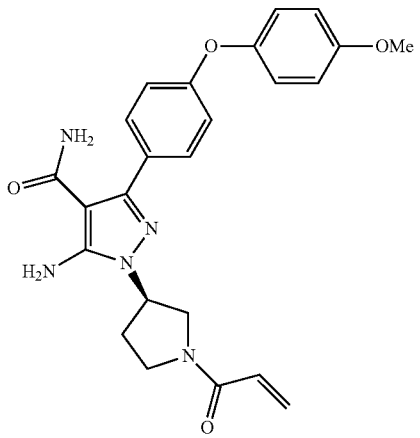
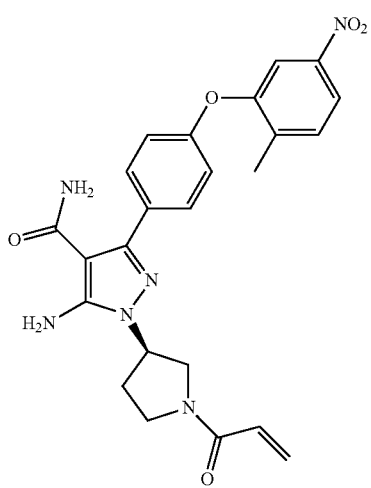

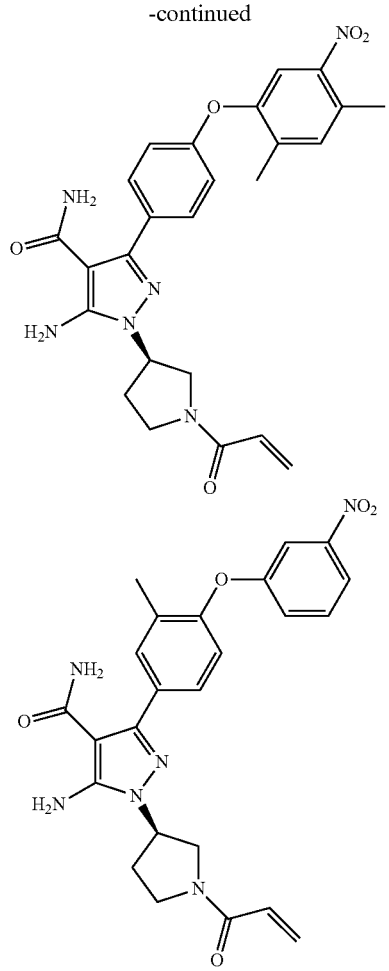
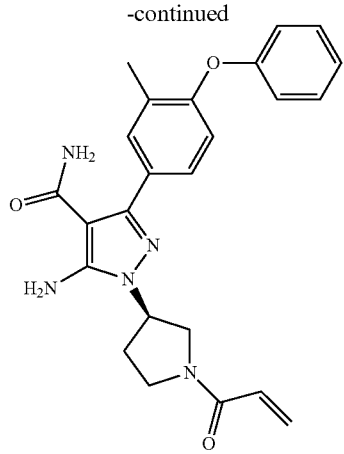
or a therapeutically acceptable salt, solvate, polymorph, ester, tautomer, or prodrug thereof.
9. A pharmaceutical composition comprising at least one compound according to claim 1, or a therapeutically acceptable salt, solvate, polymorph, ester, tautomer, or prodrug thereof, and a pharmaceutically acceptable carrier.
* * * * *